(12) United States Patent
Memelink et al.

(10) Patent No.: US 7,393,946 B1
(45) Date of Patent: Jul. 1, 2008

(54) METHOD OF MODULATING METABOLITE BIOSYNTHESIS IN RECOMBINANT CELLS

(75) Inventors: Johan Memelink, Leiden (NL); Cornelia Theodora Elisabeth Van der Fits, Hoogmade (NL); Franciscus Leonardus Hendrikus Menke, Schiedam (NL); Jan Willem Kijne, Leiden (NL)

(73) Assignee: Rijksuniversiteit Leiden, Leiden (NL)

( * ) Notice: Subject to any disclaimer, the term of this patent is extended or adjusted under 35 U.S.C. 154(b) by 0 days.

(21) Appl. No.: 09/890,782

(22) PCT Filed: Feb. 7, 2000

(86) PCT No.: PCT/NL00/00075

§ 371 (c)(1),
(2), (4) Date: May 10, 2002

(87) PCT Pub. No.: WO00/46383

PCT Pub. Date: Aug. 10, 2000

Related U.S. Application Data

(60) Provisional application No. 60/119,388, filed on Feb. 10, 1999.

(30) Foreign Application Priority Data

Feb. 5, 1999 (DK) .............................. 1999 00158

(51) Int. Cl.
C12N 15/82 (2006.01)
C12N 15/29 (2006.01)

(52) U.S. Cl. .................................... 536/23.6; 435/320.1

(58) Field of Classification Search ................. 435/419, 435/468; 536/23.6; 800/278
See application file for complete search history.

(56) References Cited

U.S. PATENT DOCUMENTS 6,653,533 B1 * 11/2003 Martin et al. ............... 800/301

FOREIGN PATENT DOCUMENTS

| JP | 09-224672 | 9/1997 |
| JP | 2000-060558 | 2/2000 |
| JP | 2000-116260 | 4/2000 |
| WO | WO 98/07942 | 2/1998 |
| WO | WO 98/09521 | 3/1998 |
| WO | WO 99/37794 | 7/1999 |
| WO | WO 99/38977 | 8/1999 |
| WO | WO 00/09712 | 2/2000 |

OTHER PUBLICATIONS

Okamuro et al. The AP2 domain of APETALA2 defines a large new family of DNA binding proteins in *Arabidopsis*. Proc Natl Acad Sci U S A. Jun. 24, 1997;94(13):7076-81.*
Krizek B.A. Aintegumenta utilizes a mode of DNA recognition distinct from that used by proteins containing a single AP2 domain. Nucleic Acids Res. Apr. 1, 2003;31(7):1859-68.*
Van der Fits L. et al. ORCA3, a jasmonate-responsive transcriptional regulator of plant primary and secondary metabolism. Science. Jul. 14, 2000;289(5477):295-7.*
Memelink J. et al. ORCAnization of jasmonate-responsive gene expression in alkaloid metabolism. Trends Plant Sci. May 2001;6(5):212-9. Review.*
Liu Q. et al. Two transcription factors, DREB1 and DREB2, with an EREBP/AP2 DNA binding domain separate two cellular signal transduction pathways in drought- and low-temperature-responsive gene expression . . . Plant Cell. Aug. 1998;10(8):1391 406.*
Riechmann J.L. et al. The AP2/EREBP family of plant transcription factors. Biol Chem. Jun. 1998;379(6):633-46. Review.*
M. Ohme-Takagi, *Nicotiana tabacum* mRNA for ERF1, complete CDS, EMBL Accession No. D3823, May 1, 1995.*
Ohme-Takagi, TrEMBL Accession No. Q40476, Nov. 1, 1996, *Nicotiana tabacum* ERF1 amino acid sequence.*
Sequence 1, Application US/0920216B, Patent No. 6653533, Jun. 14, 1999.*
Sequence 2, Application US/09202161B, Patent No. 6653533, Jun. 14, 1999.*
Park J.M. et al. Overexpression of the tobacco Tsi1 gene encoding an EREBP/AP2-type transcription factor enhances resistance against pathogen attack and osmotic stress in tobacco. Plant Cell. May 2001;13(5):1035-46.*
McElligott M.A. et al. (Lysosomal degradation of ribonuclease A and ribonuclease S-protein microinjected into the cytosol of human fibroblasts. J Biol Chem. Oct. 1985;260(22):11986-93.*
Estelle M. Proteases and cellular regulation in plants. Curr Opin Plant Biol. Jun. 2001;4(3):254-60. Review.*
Waterhouse et al. Virus resistance and gene silencing: killing the messenger. Trends Plant Sci. Nov. 1999;4(11):452-457.*
van der Krol A.R. et al. Inhibition of flower pigmentation by antisense CHS genes: promoter and minimal sequence requiremen for the antisense effect. Plant Mol Biol. Apr. 1990;14(4):457-66.*
Sandler S.J. et al. Inhibition of gene expression in transformed plants by antisense RNA. Plant Molecular Biology, 1988, vol. 11 No. 3, pp. 301-310.*
Aerts R.J. et al. Methyl jasmonate vapor increases the developmentally controlled synthesis of alkaloids in *Catharanthus* and *Cinchona* seedings. The Plant Journal, vol. 5, Issue 5, May 1994, pp. 635-643.*
van der Fits et al. ORCA3, a jasmonate-responsive transcriptional regulator of plant primary and secondary metabolism. Science. Jul. 14, 2000;289(5477):295-7.*
Liu, Q, et al., "Two Transcription Factors, DREB1 and DREB2, With an EREBP/AP2 DNA . . . " *Plant Cell*, vol. 10, No. 8, Aug. 1998 pp. 1391-1406.

(Continued)

*Primary Examiner*—Cynthia Collins
(74) *Attorney, Agent, or Firm*—Young & Thompson

(57) ABSTRACT

A method for modulating in a cell the expression of one or more genes involved in the biosynthesis of a metabolite or a precursor for this metabolite by inserting into a cell a nucleotide sequence coding for a transcription factor comprising an AP2 DNA-binding domain, and/or by modifying the expression of a nucleotide sequence coding for such a transcription factor already present in the cell is provided. The method is useful for enhancing the biosynthesis of secondary metabolites in plants such as alkaloids including terpenoid indole alkaloids. Also provided is a method for enhancing stress tolerance in plants by the use of such transcription factors.

14 Claims, 12 Drawing Sheets

OTHER PUBLICATIONS

Figure 1:
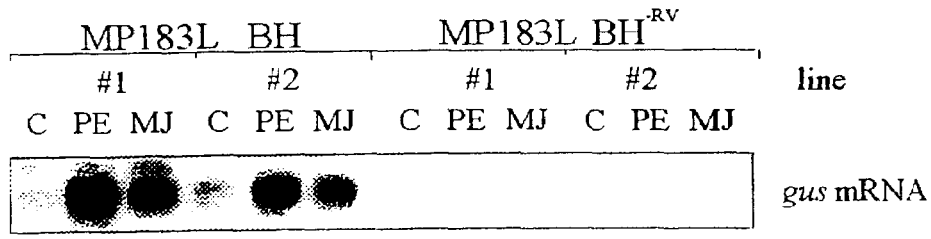

Jaglo-Ottosen, K.R. et al., "*Arabidopsis* CBF1 Overexpression Induces Dor Genes and Enhances Freezing Tolerance", *Science*, vol. 280, No. 5360, Apr. 3, 1998, pp. 104-106.

C. Canel et al., "Effects of Over-Expression of Strictosidine Synthase and Tryptophan Decarboxylase on Alkaloid . . . ", *Planta*, vol. 205, No. 3, Jul. 1998, pp. 414-419.

J.V. Shanks et al., Quantification of Metabolites in the Indole Alkaloid Pathways of *Catharanthus Roseus*: . . . , Biothechnology . . . , vol. 58, No. 2-3, Apr. 20, 1998, pp. 333-338.

D. Hallard et al., "Suspension Cultured Trnsgenic Cells of *Nicotiana tabacum* Expressing Tryptophan Decarboxylase . . . ", *Plant Cell Reports*, vol. 17, No. 1, Nov. 1997, pp. 50-54.

M. Ohme-Takagi, "*Nicotaina tabacum* mRNA for ERF1, Completer CDS", EMBL Accession No. D3823, May 1, 1995.

X. Lin et al., *Arabidopsis thaliana* Chromosme II Section 240 of 266 of the Complete Sequence. Sequence From Clones EMBL Accession No. AC002388, Aug. 4, 1997.

G. Pasquali, "*C. Roseus* STRL Gene" EMBL Accession No. Y10182, Dec. 23, 1996.

F.L.H. Menke et al., "A Novel Jasmonate- and Elicitor-Responsive Element in the Periwinkle Seondary Metabolite Biosynthetic . . . ", EMBO (European Molecular Biology Organization) vol. 18, No. 16, Aug. 16, 1999, pp. 4455-4463.

S.J. Gilmour et al., "Low Temperature Regulation of the *Arbidopsis* CBF Family of AP2 Transcriptional Activators . . . ", *Plant Journal, GB, Blackwell Scientific Publications*, vol. 16, No. 4, Nov. 1998, pp. 433-442.

E. Grotewald et al., "Engineering Secondary Metabolism in Maize Cells by Ectopic Expression of Transcription Factors", *The Plant Cell*, vol. 10, May 1998, pp. 721-740.

\* cited by examiner

*Str* - promoter - *gusA*
co-bombarded with empty vector  35S - *Orca3*

*Tdc* - promoter - *gusA*
co-bombarded with empty vector  35S - *Orca3*

**4RV - *gusA*
co-bombarded with** empty vector

35S - *Orca1*

35S - *Orca2*

35S - *Orca3*

METHOD OF MODULATING METABOLITE BIOSYNTHESIS IN RECOMBINANT CELLS

FIELD OF THE INVENTION

The present invention relates to the field of modulating the biosynthesis of metabolites in cells. More particularly, the invention relates to the cloning and expression of transcription factor genes, such as genes coding for AP2 domain class transcription factors and the use of such transcription factor for regulating the expression of genes involved in the biosynthesis of metabolites or precursors therefor. Especially the invention relates to the cloning and expression of AP2 domain class plant transcription factors and use hereof for regulating the expression of biosynthetic genes involved in the metabolite biosynthesis (i.e. of primary and/or secondary metabolites, and in particular of secondary metabolites) in plant cells.

BACKGROUND OF THE INVENTION AND PRIOR ART

Generally, two basic types of metabolites are synthesised in cells, i.e. those referred to as primary metabolites and those referred to as secondary metabolites. A primary metabolite is any intermediate in, or product of the primary metabolism in cells. The primary metabolism in cells is the sum of metabolic activities that are common to most, if not all, living cells and are necessary for basal growth and maintenance of the cells. Primary metabolism thus includes pathways for generally modifying and synthesising certain carbohydrates, proteins, fats and nucleic acids, with the compounds involved in the pathways being designated primary metabolites.

In contrast hereto, secondary metabolites usually do not possess a basal function in cell growth and maintenance. They are a group of chemically very diverse products that often have a restricted taxonomic distribution. Secondary metabolites normally exist as members of closely related chemical families, usually of a molecular weight of less than 1,500, although some bacterial toxins are considerably larger. Two examples of fungal cell secondary metabolites are penicillin and ergotamine.

Plant metabolites include a diverse array of chemically unrelated compounds such as carbohydrates and lipids (e.g. mono-, oligo- and polysaccharides, sugar alcohols, organic acids, fatty acids and lipids, acetylenes and thiophenes), nitrogen-containing compounds (e.g. amino acids, amines, glycosides, glucosinolates, purines, pyrimidines and polypeptides) of which most, but not all, generally are referred to as primary metabolites. Accordingly, some compounds such as fatty acids, sugars and steroids may e.g. be categorised both as primary metabolites and secondary metabolites (see e.g. Dewick, P. M., 1997, Medicinal Natural Products A Biosynthetic Approach, John Wiley & Sons, Chichester).

Secondary plant metabolites include e.g. alkaloid compounds (e.g. terpenoid indole alkaloids and indole alkaloids), phenolic compounds (e.g., quinones, lignans and flavonoids), terpenoid compounds (e.g. monoterpenoids, iridoids, sesquiterpenoids, diterpenoids and triterpenoids). In addition, secondary metabolites include small molecules (i.e., having a molecular weight of less than 600), such as substituted heterocyclic compounds which may be monocyclic or polycyclic, fused or bridged.

Many plant secondary metabolites have value as pharmaceuticals, food colours, flavours and fragrances. Plant pharmaceuticals include e.g.: taxol, digoxin, colchicine, codeine, morphine, quinine, shikonin, ajmalicine and vinblastine. Examples of secondary metabolites that are useful as food additives include anthocyanins, vanillin, and a wide variety of other fruit and vegetable flavours and texture modifying agents.

Plant secondary metabolites such as terpenoid indole alkaloids (TIA) represent a class of pharmaceutically useful compounds which naturally occur in many plant species.

Some plant secondary metabolites are linked to plant or plant cell defence mechanism and may e.g. confer to the plant antimicrobial activity, protection against UV light, herbivores, pathogens, insects and nematodes, and the ability to grow at low light intensity.

There are numerous examples of the application of plant secondary metabolites such as TIA's in medicine. The monomeric alkaloids serpentine and ajmalicine found in *Catharanthus roseus* are e.g. used as tranquillisers and to reduce hypertension, respectively. The dimeric alkaloids vincristine and vinblastine, also found in *C. roseus*, are potent antitumor drugs. Camptothecin, a monomeric TIA found in *Camptotheca acuminata*, also possesses anti-tumor activity. Quinine from *Cinchona officinalis* is used in malaria treatment.

However, a major problem associated with the industrial use of the above metabolites is that only very small or variable amounts of these compounds are present in plants. The recovery of useful metabolites from their natural sources is thus in many instances difficult due to the enormous amounts of source material which may be required for the isolation of utilisable quantities of the desired products. As an example, over 500 kg of *Catharanthus roseus* is needed to obtain 1 g of vincristine. Extraction is both costly and tedious, requiring large quantities of raw material and extensive use of chromatographic fractionation procedures. The low levels of these compounds in plants may also imply that many of the compounds are not detected when performing normal screening procedures, hence many unknown compounds may exist.

Biosynthesis of TIA compounds proceeds in most plants via many enzymatic steps. TIA compounds consist of an indole moiety provided by tryptamine and a terpenoid portion provided by the iridoid glucoside compound secologanin. Tryptamine is derived from primary metabolism by a single enzymatic conversion of the amino acid tryptophan, a reaction catalysed by the enzyme tryptophan decarboxylase (TDC) (EC 4.1.1.28). The biosynthesis of secologanin requires a number of enzymatic conversions of which the first step is the hydroxylation of geraniol by the enzyme geraniol 10-hydroxylase (G10H). Tryptamine and secologanin are condensed by the enzyme strictosidine synthase (STR) (EC 4.3.3.2) to form strictosidine, which is the general precursor of all terpenoid indole alkaloids found in plants. The first enzymatic conversion of strictosidine into strictosidine aglucon is catalysed by strictosidine-β-D-glucosidase (SGD) (EC 3.2.1.105). Many different enzyme activities convert strictosidine aglucon into the large variety of terpenoid indole alkaloid end products.

The best progress on molecular characterisation of the terpenoid indole alkaloid pathway has been made with *C. roseus* or Madagascar periwinkle, a member of the Apocynaceae family. *C. roseus* cells have the genetic potential to synthesise over a hundred terpenoid indole alkaloids. The biosynthesis of terpenoid indole alkaloids is strongly regulated, and depends on plant cell type and environmental conditions. Their biosynthesis is e.g. induced by fungal elicitors, jasmonates and auxin starvation. Many monomeric TIA compounds are found in all plant organs, but vindoline and vindoline-derived dimeric alkaloids are only found in chloroplast-containing plant tissues.

Until now, only a limited number of genes coding for enzymes involved in terpenoid indole alkaloid biosynthesis have been cloned, such as cDNA clones encoding STR and TDC isolated from *C. roseus*. In addition, cDNA clones from NADPH:cytochrome P450 reductase (CPR), which is essential for the G10H-catalysed reaction, and SGD have been isolated.

Gene expression studies by the present inventors have shown that the regulation of terpenoid indole alkaloid biosynthesis is controlled largely, if not uniquely, at the level of the expression of biosynthetic genes. Accordingly, analysis of the expression of the terpenoid indole alkaloid biosynthetic genes Tdc and Str1 showed that their expression is low, especially in cell cultures. It was found, that the level of gene expression is likely to be limiting for alkaloid production. Overexpression of a single biosynthetic gene (Tdc or Str1) in transgenic *C. roseus* cells resulted in significantly elevated levels of the corresponding enzyme activity. However, this did not result in elevated alkaloid levels, presumably because many other enzymes are limiting and would need to be overexpressed.

These studies have further demonstrated what is already known, that the genes are coordinately regulated depending on cell type or environmental conditions. Str1 and Tdc mRNA accumulate in suspension-cultured cells after auxin starvation or phosphate starvation, exposure to fungal elicitors or (methyl) jasmonate and their distribution in the plant is developmentally regulated with the highest levels in the roots. In leaves Tdc and Str1 are induced by a UV-B light pulse. Cpr mRNA accumulation is rapidly induced by fungal elicitor.

The observations that mRNA from genes involved in the biosynthesis of TIA compounds such as Tdc and Str1 mRNAs coordinately accumulate in response to fungal elicitors, (methyl)-jasmonate, UV light, auxin depletion, phosphate depletion, and have similar tissue-specific distributions, have led the present inventors to hypothesise that the Tdc and Str1 genes might be controlled by one or more common regulating factor(s) or substance(s). It was further hypothesised that among possible regulating factors, transcription factors could have such a regulating effect.

It is known that certain transcription factors can regulate complex cell differentiation processes in animals involving numerous target genes. A notable example is muscle differentiation, where either one of a set of myogenic bHLH transcription factors (MyoD, myogenin, Myf5, MRF4) in combination with the MADS-domain transcription factor MEF2 induces muscle cell differentiation and switches on numerous muscle-specific genes. Other examples include homeodomain transcription factors in the fruit fly that regulate cell processes resulting in the determination of segment identity.

The pathway that is most extensively studied in plant secondary metabolism at the transcriptional level, is the one leading to the formation of the anthocyanin pigments. The genes encoding flavonoid biosynthetic enzymes are controlled by a combination of two distinct transcription factor species, one of which has homology to the protein encoded by the vertebrate proto-oncogene c-Myb, and the other with the vertebrate bHLH protein encoded by the proto-oncogene c-Myc. These transcription factors bind to specific sequences in the promoters of the target genes.

The DNA-binding domain of plant MYB proteins consists of two, or for some of them, one imperfect repeat(s). The MYC proteins have a bHLH-type (basic helix-loop-helix) DNA-binding domain and recognise variants of the sequence CANNTG. About ten enzymes are involved in the biosynthesis of anthocyanins starting from phenylalanine. In maize, the entire set of genes encoding these enzymes are thought to be regulated coordinately by the Myc gene R and the Myb gene C1 in the aleurone (epidermal layer of the kernel endosperm), and by homologous genes in other parts of the plant.

Overexpression of the maize Lc gene encoding a MYC-type regulatory protein in Petunia upregulated the whole flavonoid biosynthetic pathway starting from Chs and including the earlier and later genes, resulting among others in intensely pigmented leaves. The expression of the general phenylpropanoid genes Pal and C4h was not affected by Lc overexpression, indicating that Lc only regulates structural genes in the flavonoid branch.

Introduction of the maize R and C1 MYC-type regulators in *Arabidopsis* intensified pigmentation in normally pigmented tissues and induced pigmentation in plant tissues that are normally unpigmented. In maize cell suspension, ectopic expression of C1 and R led to the accumulation of anthocyanins and a number of other related 3-hydroxy flavonoids. In addition, six anthocyanin structural genes that are targets for C1/R were expressed at high levels in the transgenic cell line.

In the plant *Arabidopsis thaliana*, it has been shown that overexpression of the transcription factor CBF-1 that belongs to the AP2 domain class transcription factors resulted in coordinate upregulation of a set of cold-regulated genes. However, there are no suggestions that transcription factors of this class may have an effect on the biosynthesis of metabolites in plant cells and other cells.

The present inventors have now discovered that transcription factors having an AP2 DNA-binding domain are highly useful as central regulators of complex metabolite pathways involving numerous target genes for such transcription factors. This discovery has opened up for providing novel effective means of generating novel metabolite compounds, significantly enhancing the yield of commercially valuable metabolite compounds and also for enhancing the tolerance of plants towards exogenous stress factors and conditions.

Besides such activation of metabolic pathways for the production of metabolites, it is also envisaged that the method of the invention may be used for such purposes as:

study of (plant) metabolism, in which the method of the invention may for instance be used to activate the metabolic pathway(s) under investigation;

study of gene expression, including but not limited to expression profiling, in that the method of the invention allows (the simultaneous) overexpression of one or more genes involved in one or more metabolic pathway(s), the expression or gene products of which may then be studied/determined;

to determine whether one or more specific (usually secondary) metabolites are formed in a plant, by enhancing the levels of said metabolites present in and/or formed by the plant (e.g. from a level below the detection limit of the assay/equipment used to a level above said limit);

lowering or removal of unwanted or toxic metabolites present in a plant or plant material;

discovery enzymes or regulators thereof involved in primary or secundary metabolism.

Further applications will become clear to the skilled person on the basis of the description given hereinbelow.

SUMMARY OF THE INVENTION

Accordingly, the invention relates in one aspect to a method of modulating in a cell the expression of one or more genes involved in the biosynthesis of a metabolite or a precursor herefor, the method comprising inserting into the cell a nucleotide sequence coding for a transcription factor other than a transcription factor having a bHLH-type or a MYB-type DNA-binding domain, the nucleotide sequence is operably linked to at least one expression regulating sequence, and/or modifying the expression of a nucleotide sequence coding for such a transcription factor already present in the cell, the transcription factor is capable of regulating the expression of at least one gene coding for a gene product involved in the biosynthesis of said metabolite or precursor, and subjecting the cell to conditions where the inserted nucleotide sequence coding for a transcription factor is expressed or the expression of the nucleotide sequence already present in the cell is modulated.

In a further aspect the invention relates to a method of modulating the stress resistance of a cell, the method comprising inserting into the cell a nucleotide sequence coding for a transcription factor, the nucleotide sequence is operably linked to at least one expression regulating sequence, and/or modifying the expression of a nucleotide sequence coding for such a transcription factor already present in the cell, the transcription factor is capable of regulating the expression of at least one gene coding for a gene product involved in the biosynthesis of said metabolite or precursor, and subjecting the cell to conditions where the inserted nucleotide sequence coding for a transcription factor is expressed or the expression of the nucleotide sequence already present in the cell is modulated, the expression of said nucleotide sequence resulting in a modified responsiveness of the cell towards exogenous stress conditions.

There is also provided a recombinant cell having, relative to its parent cell, enhanced or reduced biosynthesis of a metabolite or a precursor therefor, and/or enhanced or reduced expression of a gene product involved in metabolite production, the cell comprising a nucleotide sequence coding for a transcription factor other than a transcription factor having a bHLH-type or a MYB-type DNA-binding domain, said transcription factor is capable of regulating the expression of at least one gene coding for a gene product involved in the metabolite production, said sequence is inserted into the cell and/or its expression is modified by operably linking it to a regulating sequence with which it is not natively associated.

The invention pertains in a still further aspect to a method of producing a metabolite including a plant secondary metabolite, the method comprising providing a recombinant cell according to the invention, cultivating the cell under conditions where the nucleotide sequence coding for the transcription factor regulating the expression of at least one gene coding for a gene product involved in the metabolite production is expressed, and recovering the metabolite.

There is also provided a method of constructing a recombinant cell according to the invention, the method comprising the steps of
(i) identifying in a source cell a nucleotide sequence coding for a transcription factor other than a transcription factor having a bHLH-type or a MYB-type DNA-binding domain, said transcription factor is capable of regulating in the source cell the expression of at least one gene coding for a gene product involved in biosynthesis of a metabolite or a precursor therefor,
(ii) isolating said nucleotide sequence; and
(iii) inserting said isolated nucleotide sequence into a host cell comprising a gene coding for a gene product involved in biosynthesis of a metabolite or a precursor therefor, the insertion of said nucleotide sequence resulting in that the expression of the gene of the host cell is modulated relative to the expression level in a host cell not comprising the inserted nucleotide sequence.

In still further aspects there are provided an isolated nucleic acid molecule comprising a nucleotide sequence coding for an amino acid sequence selected from the group consisting of SEQ ID NO:4, SEQ ID NO:5 and SEQ ID NO:6, a polypeptide which includes an amino acid sequence having at least 40% homology including at least 50%, such as at least 60%, at least 70%, at least 80% and at least 90% to an amino acid sequence selected from the group consisting of SEQ ID NO:4, SEQ ID NO:5 and SEQ ID NO:6 and a polypeptide having the amino acid sequence shown in SEQ ID NO:4, SEQ ID NO:5 or SEQ ID NO:6.

In other aspects, the invention pertains to a vector comprising a nucleic acid molecule according to the invention, a host cell comprising such a vector, and a method of isolating a nucleotide sequence coding for a transcription factor not having a bHLH-type or a MYB-type DNA-binding domain, said transcription factor is capable of regulating in a cell the expression of at least one gene coding for a gene product involved in biosynthesis of a metabolite or a precursor therefor, the method comprising the steps of
(i) probing a cDNA or genomic library with a probe comprising at least a fragment of nucleic acid selected from the group consisting of SEQ ID NO:1, SEQ ID NO:2 and SEQ ID NO:3 and/or a nucleic acid coding for an amino acid sequence selected from the group consisting of SEQ ID NO:4, SEQ ID NO:5 and SEQ ID NO:6
(ii) identifying a DNA clone that hybridises with said nucleic acid; and
(iii) isolating the DNA clone identified in step (ii) wherein the nucleic acid sequence is coding for all or a part of said transcription factor The invention also relates to a method of isolating a nucleotide sequence coding for a transcription factor not having a bHLH-type or a MYB-type DNA-binding domain, said transcription factor is capable of regulating in a cell the expression of at least one gene coding for a gene product involved in biosynthesis of a metabolite or a precursor therefor, the method comprising the steps of
(i) synthesising an oligonucleotide primer set corresponding to at least a fragment of a sequence selected from the group consisting of SEQ ID NO:1, 2 and 3; and
(ii) amplifying cDNA or genomic DNA using said primer set in a polymerase chain reaction wherein the amplified nucleic acid fragment is coding for all or a part of said transcription factor to obtain a nucleotide sequence coding for a transcription factor not having a bHLH-type or a MYB-type DNA-binding domain.

The invention also pertains to an isolated nucleic acid which is a nucleotide sequence as shown in SEQ ID NO: 7 and a mutant, allele or variant hereof and the use of this isolated nucleic acid sequence for isolating a nucleotide sequence coding for a transcription factor not having a bHLH-type or a MYB-type DNA-binding domain, said transcription factor is capable of regulating in a cell the expression of at least one gene coding for a gene product involved in biosynthesis of a metabolite or a precursor therefor.

PREFERRED ASPECTS AND EMBODIMENTS OF THE INVENTION

Hereinbelow, some preferred but non-limiting aspects and embodiments of the invention will be discussed in more detail.

In a first aspect, the invention relates to a method of modulating in a cell the level(s) of one or more metabolites, said method comprising providing to the cell at least one transcription factor other than a transcription factor having a bHLH-type or a MYB-type DNA-binding domain.

In another aspect, the invention relates to a method of modulating in a cell the expression of one or more genes involved in the biosynthesis of a metabolite or a precursor herefor, said method comprising providing to the cell at least one transcription factor other than a transcription factor having a bHLH-type or a MYB-type DNA-binding domain.

Also, in yet another aspect, the invention relates to a method of modulating the stress resistance of a cell, said method comprising providing to the cell at least one transcription factor other than a transcription factor having a bHLH-type or a MYB-type DNA-binding domain.

In the above methods, at least one transcription factor is preferably provided to the cell by the expression in said cell, under the control of an expression regulating sequence operable in said cell, of at least one nucleotide sequence that encodes said at least one transcription factor. In particular, this may be achieved by the steps of:

(a) transforming the cell with a genetic construct, said construct comprising the at least one nucleotide sequence encoding the at least one transcription factor, operably linked to said expression regulating sequence;

(b) maintaining the cell under conditions such that the at least one nucleotide sequence encoding the at least one transcription factor is expressed in said cell.

Usually the expression regulating sequence used in this method will be heterologous to the cell and/or will be an expression regulating sequence with which the at least one nucleotide sequence that encodes said at least one transcription factor is not natively associated, although in its broadest sense, the invention is not limited thereto.

Generally, by providing a transcription factor to a cell in accordance with the method of the invention, the level in the cell of the one or more metabolites, including primary metabolites, secondary metabolites or precursors and/or intermediates therefor, is enhanced or reduced, e.g. relative to a cell to which said transcription factor is not provided.

Providing a transcription factor to a cell in accordance with the method may also lead to enhanced or reduced levels of enzymes or enzyme regulating factors involved in primary or secondary metabolism.

In particular, by the method of the invention, the level in the cell of the one or more metabolites may be enhanced by at least 10%, at least 25% or at least 100%, e.g. relative to a cell to which the transcription factor is not provided.

Alternatively, by the method of the invention, the level in the cell of the one or more metabolites may be reduced by at least 10%, at least 25%, at least 50%, or at least 95%, e.g. relative to a cell to which the transcription factor is not provided Also, by the method of the invention, the level of one or more metabolites may be enhanced (e.g. by the amounts indicated above), while at the same time, the level of one or more other metabolites may be reduced (e.g. by the amounts indicated above).

Also, by providing a transcription factor to a cell in accordance with the method of the invention, the expression in the cell of one or more genes involved in the biosynthesis of a metabolite or a precursor herefor is enhanced or reduced, e.g. relative to a cell to which the transcription factor is not provided.

In particular, by the method of the invention, the expression in the cell of one or more genes involved in the biosynthesis of a metabolite or a precursor herefor may be enhanced by at least 10%, at least 25% or at least 100%, relative to a cell to which the transcription factor is not provided.

Alternatively, by the method of the invention, the expression in the cell of one or more genes involved in the biosynthesis of a metabolite or a precursor herefor may be reduced by at least 10%, at least 25% or at least 50%, or at least 95%, relative to a cell to which the transcription factor is not provided.

Also, by the method of the invention, the expression in the cell of one or more genes involved in the biosynthesis of a metabolite or a precursor herefor may be enhanced (e.g. by the amounts indicated above), while at the same time, the expression in the cell of one or more other genes involved in the biosynthesis of a metabolite or a precursor herefor may be reduced (e.g. by the amounts indicated above).

The transcription factor used in the invention is preferably a factor of the "AP2/EREBP"-family. Generally, these can be defined as transcription factors that contain within their amino acid sequence one or more AP2 DNA-binding domains or -regions (hereinbelow generally referred to as "AP2 domains").

Such AP2 domains are known per se, for instance from Riechmann J. L., Meyerowitz E. M. (1998), Biological Chemistry 379: 633-646; and one or more of the AP2 domains described in this reference may be present in the transcription factors used in the invention.

In addition to—or instead of—one or more of the AP2 domains described in the Riechmann and Meyerowitz reference, the transcription factors used in the invention may also contain one or more other AP2 domains. These may be other naturally occurring AP2 domains or may be mutants, analogs, variants, parts or fragments of any naturally occurring AP2 domain, including but not limited to mutants, analogs, variants, parts or fragments of the AP2 domains described in the Reichmann and Meyerowitz reference. Such mutants, analogs, variants, parts or fragments may be derived from the amino acid sequence of a naturally occurring AP2 domain by addition, substitution, insertion and/or deletion of one or more amino acid residues in the naturally occurring sequence, e.g. as further described below.

Preferably, any such AP2 domain (including mutants, analogs, variants, parts or fragments) will have at least 35% amino acid residue identity with at least one of the AP2 domains described by Riechmann and Meyerowitz, such as at least 45%, at least 55%, at least 65%, at least 75%, at least 85%, at least 95% or at least 98% residue identity. For this purpose, the percentage of "amino acid residu identity" of a given sequence to the sequence of an AP2 domain described by Reichmann and Meyerowitz may be calculated by: "[the number of amino acid residues in the given sequence that correspond to the amino acid residue on the same position in the sequence of the AP2 domain] divided by [the total number of amino acid residues in the sequence of the AP2 domain] times 100%", in which an insertion and/or a deletion of an amino acid residue is taken as a difference at a single amino acid residue/position. All AP2 domains, including but not limited to mutants, analogs, variants, parts or fragments of naturally occurring AP2 domains, that fall within this general definition should be considered encompassed within the term "AP2 domain" as used herein.

As mentioned in the Reichmann and Meyerowitz reference, other suitable AP2 domains may be easily identified through BLAST searches due to the high degree of conservation of the sequence of the AP2 domain. After a suitable AP2 domain has been identified, (a nucleotide sequence encoding) said domain may then for instance be isolated from its natural source, optionally as part of (a nucleotide sequence encoding) a full naturally occurring transcription factor. Also, (nucleotide sequences encoding) mutants, analogs, variants, parts or fragments of such naturally occurring AP2 domains may for instance be provided starting from such naturally occurring sequences, e.g. as further described below.

Any AP2 domain(s) used in the invention will generally contain the features of the AP2 domains as summarized by Riechmann and Meyerowitz (vide page 635, right hand column), for which reference is also made to Okamuro et al, Proc. Natl. Acad. Sci. USA, 94, 7076-7081, both incorporated herein by reference. For instance, any amino acid sequence having similarity to any of the two conserved segments of the AP2 domains as defined by Riechmann and Meyerowitz— i.e. the YRG element and the RAYD element—could also be used in the invention.

Preferably, the AP2 domain(s) present in the transcription factor(s) used in the invention is/are selected from the AP2 domains of SEQ ID NO:4, SEQ ID NO:5 or SEQ ID NO:6; and/or from amino acid sequences having at least 40% homology, at least 50%, at least 60%, at least 70%, at least 80% or at least 90% homology to one of the AP2 domains of SEQ ID NO:4, SEQ ID NO:5 and SEQ ID NO:6.

As used herein, the term "homology" refers to homology at the amino acid level both in terms of amino acid identity and similarity. Similarity allows for "conservative variation", i.e. substitution of one hydrophobic residue such as isoleucine, valine, leucine or methionine with another hydrophobic residue, or the substitution of one polar residue with another polar residue, such as arginine with lysine, glutamic acid with aspartic acid, or glutamine with asparagine. In the present context, similarity is defined and determined using the present version of the BLAST program (Altschul et al, Nucleic Acids Res 25:3389-3402, 1997).

The transcription factor(s) used in the invention may contain a single AP2-domain, two AP2 domains, or even more than two AP2-domains. As such, they may for instance contain one or more of the AP2 domains described in the Riechmann and Meyerowitz reference; one or more other naturally occurring AP2 domains; one or more mutants, analogs, variants, parts or fragments of a naturally occurring AP2 domain; or any combination thereof. Combined, these transcription factors containing one or more AP2 domains will be referred to hereinbelow as "AP2 transcription factors".

Besides the one or more AP2 domains, the AP2 transcription factors used in the invention preferably also contain one or more of the other elements known per se for transcription factors, and in particular one or more of the other elements known per se for AP2 transcription factors, e.g. as described in the Reichmann and Meyerowitz reference. These include, but are not limited to, one or more transcription activation domains (usually regions of biased amino acid composition such as acidic-rich, glutamine-rich, proline-rich, and/or serine/threonine-rich regions) and—if more than one AP2 domain is present—one or more linking regions or—sequences between the AP2 domains.

The AP2 transcription factor used in the invention may be a naturally occurring AP2 transcription factor or may be a "synthetic" AP2 transcription factor, e.g. as described below.

Naturally occurring AP2 transcription factors suitable for use in the invention include, but are not limited to, the transcription factors described in the Reichmann and Meyerowitz reference or other naturally occurring AP2 transcription factors known per se. As mentioned in the Reichmann and Meyerowitz reference, such other AP2 transcription factors may be easily identified through BLAST searches due to the high degree of conservation of the sequence of the AP2 domain(s).

When a naturally occurring AP2 transcription factor is used, it may be derived from any suitable biological source, which will usually be a plant, and in particular dicotyledonous plant; and some preferred, but non-limiting sources will be mentioned hereinbelow.

Also, when a naturally occurring AP2 transcription factor is used, it may have been derived from essentially the same plant as the plant (cell) to which said transcription factor is to be provided according to the method of this invention, e.g. from a plant belonging to the same variety, species or genus. However, the invention is not limited thereto and in its broadest sense, any AP2-transcription factor or nucleotide sequence coding therefor may be used, irrespective of its origin.

Preferably, the AP2 transcription factor used is such that it causes, in the cell to which it is provided/in which it is expressed:

an enhancement of the level(s) in the cell of one or more metabolites, a reduction of the level(s) in the cell of one or more (other) metabolites; or a combination thereof, e.g. as described above and/or by the amounts indicated above; and/or an enhancement of the expression in the cell of one or more genes involved in the biosynthesis of a metabolite or a precursor herefor, a reduction of the expression in the cell of one or more genes involved in the biosynthesis of a metabolite or a precursor herefor; or a combination thereof, e.g. as described above and/or by the amounts indicated above.

As mentioned in the Riechmann and Meyerowitz reference, in nature AP2 transcription factors—i.e. with one, two or more than two AP2 domains—may for instance be involved in the environmental (light, temperature, etc.) and/or stress response(s) by a plant (cell); in the growth and/or development of a plant, and similar biological responses in or by a plant.

Thus, according to one particular embodiment, the transcription factor may be a naturally occurring transcription factor, and in particular a naturally occurring AP2 transcription factor, that is involved in the (intracellular) response of a plant (cell) to external stress, including but not limited to response(s) to a pathogen (e.g. bacteria, viruses, fungi); to physical damage including but not limited to damage caused by herbivores, insects, worms and other multicellular organisms; to lack of (sufficient) water; to lack of (sufficient) oxygen; to lack of one or more nutrients; to lack of (sufficient) light; to cold; to heat; to high level(s) of salt(s); to UV; to ozone; to xenobiotics; etc.

Usually, these will be transcription factors containing a single AP2 domain, although the invention in its broadest sense is not limited thereto. Also, mutants, analogs, variants, parts or fragments etc. (e.g. as described below) of such naturally occurring transcription factors may be used.

Generally, the response(s) of a plant to such external stress will be mediated by one or more stress-related signalling molecules including but not limited to jasmonates, ethylene, salicylates, abscisic acid, gibberelic acids, nitrogen oxide, hydrogen peroxide, reactive oxygen species, fluctuations in intracellular calcium or other ion concentrations, phospholipids, phosphoinositides, cyclic ADP-ribose.

Thus, in a more particular embodiment, the transcription factor may be a naturally occurring transcription factor, and in particular a naturally occurring AP2 transcription factor, that is involved in the (intracellular) response of a plant (cell) to a stress related signalling molecule; and more in to particular may be a naturally occurring transcription factor that is involved in the (intracellular) response of a plant (cell) to a jasmonate, to a salicylate, to ethylene, to abscisic acid, gibberelic acids, nitrogen oxide, hydrogen peroxide, reactive oxygen species, gamma-amino-butyric-acid, fluctuations in intracellular calcium or other ion concentrations, phospholipids, phosphoinositides, cyclic ADP-ribose.

Again, these will usually be transcription factors containing a single AP2 domain, although the invention in its broadest sense is not limited thereto; and again mutants, analogs, variants, parts or fragments etc. (e.g. as described below) of such naturally occurring transcription factors may also be used.

Preferably, the transcription factor is a naturally occurring transcription factor, and in particular a naturally occurring AP2 transcription factor, that is involved in the intracellular response of a plant (cell) to a jasmonate. [In this respect, it is to be understood that the term "jasmonate" does not only include jasmonate/jasmonic acid, but also precursors thereof and other jasmonate-like signalling molecules such as methyl jasmonate, 12-oxo-PDA and other lipid-derived plant signal molecules]. Again, these transcription factors will usually be AP2 transcription factors containing a single AP2 domain, although the invention in its broadest sense is not limited thereto; and again mutants, analogs, variants, parts or fragments etc. (e.g. as described below) of such naturally occurring transcription factors may also be used.

Some specific, non-limiting examples of such naturally occurring AP2 transcription factors suitable for use in the invention include ORCA1, ORCA2, ORCA3, AtERF1, AtEBP, AtCBF1, AtDREB1, AtDREB2A, AtDREB2B, TINY, NtEREBP1, 2, 3, 4, LePti4, 5, 6, ABI4.

Of these, the following transcription factors are preferred AtERF1, AtEBP, AtCBF1, AtDREB1, NtEREBP1, 2, 3, 4, LePti4, 5, 6, ORCA1, ORCA-2 and ORCA3, of which ORCA-2 and ORCA3 are most preferred.

Also, in the invention, naturally occurring transcription factors, and in particular naturally occurring AP2 transcription factors, may be used that are involved in the growth and/or development of a plant, such as the growth and/or development of the flower, of seed, etc. Usually, these will be AP2 transcription factors containing two AP2 domains, although the invention in its broadest sense is not limited thereto. Also, again mutants, analogs, variants, parts or fragments etc. (e.g. as described below) of such naturally occurring transcription factors may also be used.

Some non-limiting examples of such transcription factors involved in plant development include: APETALA2, AINTEGUMENTA, TINY.

The term "synthetic" AP2 transcription factor as used herein generally comprises any transcription factor that contains at least one AP2 domain as defined above and that does not occur in nature. These include, but are not limited to:

transcription factors that contain one or more mutants, analogs, variants, parts or fragments of a naturally occurring AP2 domain, optionally in combination with one or more naturally occurring AP2 domains;

AP2 transcription factors that contain at least two naturally occurring AP2 domains which in nature are not natively associated;

transcription factors that comprise—compared to the sequence of a naturally occurring AP2 transcription factor—one or more amino acid insertions, deletions and/or substitutions at one or more amino acid positions outside the AP2 domain(s) present therein, such as in the transcription activation domain(s) and/or in the linking regions/sequences;

transcription factors in which one or more AP2 domains are combined with one or more transcription activation domains and/or with one or more linking sequences (where appropriate) which in nature they are not natively associated; or any combination thereof.

According to one embodiment, such synthetic AP2 transcription factors may be mutants, analogs, variants, parts or fragments of the abovementioned naturally occurring AP2 transcription factors. Such mutants, analogs, variants, parts or fragments may for instance be derived from the amino acid sequence of such a naturally occurring AP2 transcription factor by addition, substitution, insertion and/or deletion of one or more amino acid residues, e.g. in the part(s) of the sequence of the transcription factor corresponding to the AP2 domain(s); in one of the other parts of the sequence of the transcription factor sequence such as the transcription activation domain(s) and/or linking sequences; or in both.

Although generally, the parts or segments of the AP2 transcription factor other than the AP2 domain(s) will usually not be critical; however, any synthetic AP2 transcription factor used in the invention may have at least 20% amino acid residue identity with at least one of the naturally occurring AP2-transcription factors, such as at least 35%, at least 45%, at least 55%, at least 65%, at least 75%, at least 85%, at least 95% or at least 98% residue identity. For this purpose, the precentage of "amino acid residue identity" of a synthetic sequence to the sequence of a naturally occurring AP2 transcription factor may be calculated by dividing "[the number of amino acid residues in the given sequence that correspond to the amino acid residu on the same position in the sequence of the AP2 transcription factor] by [the total number of amino acid residues in the sequence of the AP2 transcription factor]× 100%", in which a substitution, an insertion and/or a deletion of an amino acid residu is taken as a difference at a single amino acid position.

Any "synthetic" AP2 transcription factor, including but not limited to mutants, analogs, variants, parts or fragments of naturally occurring AP2 transcription factors, that falls within this general definition should be considered encompassed within the term "AP2 transcription factor" as used herein. However, any such synthetic AP2 transcription factor is preferably such that it causes, in the cell to which it is provided/in which it is expressed:

an enhancement of the level(s) in the cell of one or more metabolites, a reduction of the level(s) in the cell of one or more (other) metabolites; or a combination thereof, e.g. as described above and/or by the amounts indicated above; and/or an enhancement of the expression in the cell of one or more genes involved in the biosynthesis of a metabolite or a precursor herefor, a reduction of the expression in the cell of one or more genes involved in the biosynthesis of a metabolite or a precursor herefor; or a combination thereof, e.g. as described above and/or by the amounts indicated above.

In this respect, it will be clear to the skilled person that a transcription factor which can provide such enhancement and/or reduction in one (type of) plant cell may not necessarily provide the same level of (or even any) such enhancement or reduction in another (type of) plant cell, depending upon the transcription factor and plant cell used. Also, it may be that the same transcription factor may enhance or reduce different metabolites and/or genes in different plant cells, and may even enhance a metabolite or gene in one cell but reduce it in another. All this will generally be incorporated within the scope of the invention, as long as the transcription factor used is capable of providing the enhancement or reduction described above in at least the intended plant cell.

Usually, according to the invention, an AP2 transcription factor as described above will be provided to said intended plant (cell) by means expression in said plant (cell) of a nucleotide sequence encoding said AP2 transcription factor.

Preferably, such a nucleotide sequence encoding the AP2 transcription factor is provided to the plant (cell) in the form of a genetic construct, in which the sequence encoding the AP2 transcription factor is operably linked (as defined below) to a suitable promoter (e.g. as described below). Such constructs, which are a further aspect of the present invention, may be in a form suitable for transforming a plant, such as a vector or plasmid, and may contain all other elements of genetic constructs for the transformation of plants known per se, e.g. those described below.

Upon transformation of the plant (cell) with such a construct, the AP2 transcription factor may then be expressed in the plant (cell), e.g. by keeping the plant under conditions suitable for expression, which will usually depend upon the promoter used, and which may for instance include exposure of the plant (cell) to a suitable inducing factor or compound.

Upon such expression, the AP2 transcription factor may be subject to one or more post-translational modifications, e.g. those that may occur in the plant (cell) in which the AP2 transcription factor is expressed. Thus, the term "AP2 transcription factor" as used herein does not only comprise any amino acid sequence directly obtained upon expression of the nucleotide sequence encoding an AP2 transcription factor, but also all derivatives thereof obtained through one or more post-translational modifications.

For preparing the genetic constructs to be used in the invention, nucleotide sequences encoding naturally occurring AP2 transcription factors and/or AP2 domains may be derived from a suitable source, e.g. those described above for the AP2 transcription factors themselves.

Nucleotide sequences encoding "synthetic" AP2 transcription factors (as described above) for use in the invention may for instance be provided by insertion, deletion, addition or substitution of one or more codons—or even insertion, deletion, addition or substitution, and in particular substitution, of one or more bases/nucleotides—in or compared to a naturally occurring sequence of an AP2 transcription factor; by combining two or more parts of two or more different naturally occurring AP2 domains or AP2 transcription factors; and/or by combining one or more parts of one or more different naturally occurring AP2 domains or AP2 transcription factors with one or more synthetic nucleotide sequences; or any combination thereof. This may for instance be carried out starting from one or more such naturally occurring sequences (or one or more parts thereof), e.g. by using well known techniques of genetic manipulation, including but not limited to site-directed mutaganesis, introducing mutations using mismatched PCR primers, as well as cutting and ligating of nucleic acid sequences. Alternatively, such sequences or parts thereof may be prepared using well-known DNA-synthesis techniques, although this is usually not preferred.

The synthetic AP2 transcription factor encoded by said sequence may then be provided to the plant (cell) by transformation and expression—e.g. essentially as described above—again optionally followed by one or more post-translational modifications.

Suitable techniques for providing the abovementioned nucleotide sequences and genetic constructs, as well as techniques for the transformation of plants using such constructs, will be well known to the skilled person, and some examples thereof are mentioned below. Reference is also made to the standard handbooks, such as Sambrook et al, "Molecular Cloning: A Laboratory Manual" (2nd. ed.), Vols. 1-3, Cold Spring Harbor Laboratory (1989) of F. Ausubel et al, eds., "Current protocols in molecular biology", Green Publishing and Wiley Interscience, New York (1987).

One well-known technique for transformation of plants involves the use of *Agrobacterium* strains and vector systems for use therewith. Thus, one aspect of the invention comprises an *Agrobacterium* strain containing a genetic construct/vector as described herein, as well as the use thereof in transforming a plant or plant cell.

In the invention, it was found that the expression in a plant (cell) of a naturally occurring or synthetic AP2 transcription factor—e.g. using a genetic construct as described herein—may be used to regulate one or more metabolic pathways in the plant. In particular, it was found that such expression of an AP2 transcription factor may be used to regulate simultaneously several of such metabolic pathways. These include metabolic pathways leading to one or more primary metabolites, pathways leading to one or more secondary metabolites; pathways leading to and/or from one or more key intermediates of the plant metabolism and/or precursors of primary and/or secondary metabolites; or any combination thereof.

In particular, it was found that the expression in plant (cell) of an AP2 transcription factor in accordance with the invention may be used to regulate one or more metabolic pathways leading to one or more secondary metabolites, including but not limited to those mentioned hereinabove and below.

Such regulation of the metabolic pathway(s) may alter or otherwise influence the entire metabolic pathway(s)—e.g. compared to the native situation, e.g. without exposure to stress—but also one or more separate steps (e.g. enzymatic conversions) thereof, which may include enzymatic conversions belonging to the same or to different metabolic pathways.

Furthermore, such regulaton may comprise an up-regulation of one or more of such enzymatic conversions; a down-regulation of one or more of such enzymatic conversions involved in said metabolic pathway; or any combination thereof.

Also, such regulation may result in increased formation and/or intracellular level of one or more metabolites (including primary as well as secondary metabolites); to decreased formation and/or intracellular level of one or more metabolites (again including primary as well as secondary metabolites); or any combination thereof. Furthermore, such regulation may (also) result in increased formation and/or intracellular levels of one or more (key) intermediates of the plant metabolism and/or precursors for primary and/or secondary metabolites; in decreased increased formation and/or intracellular levels of one or more (key) intermediates of the plant metabolism and/or precursors for primary and/or secondary metabolites; or any combination thereof.

Generally, the number of enzymatic steps/conversions that are modulated in accordance with the invention will depend upon the biosynthetic route(s) involved. e.g. the biosynthetic route(s) leading to—or otherwise involved in the production of—the metabolite(s) the level of which is to be modulated. As such, one or more steps of any such route may be modulated, and up to all steps involved in the biosynthesis and/or the precursor pathways of the metabolite.

Similarly, also the number of genes the expression of which is modulated in accordance with the invention may depend upon the metabolic pathway involved.

According to one aspect of the invention, providing a transcription factor to a cell via the method of the invention simultaneously modulates at least two, preferably at least three, more preferably at least 5, for instance between 2 and 50, enzymatic conversions—e.g. starting from a given precursor—and up to all enzymatic steps involved in the formation of the desired metabolite; in which said conversions may be part of one or more metabolic pathways in the cell.

Similarly, according to one aspect of the invention, providing a transcription factor to a cell via the method of the invention simultaneously modulates at least two, preferably at least three, more preferably at least 5 genes encoding expression products—e.g. enzymes—involved in said metabolic pathways, and up to all genes involved in said metabolic pathway(s).

Generally, the enzymatic conversions that may be regulated in accordance with the invention include those conversions that can be regulated by the presence/expression in the cell of an AP2 transcription factor. Generally, these will be conversions that are catalysed or otherwise mediated by polypeptides or proteins (e.g. enzymes) the expression of which may be regulated, altered or otherwise influenced—and in particular be enhanced—by the presence/expression in the cell of an AP2 transcription factor. Some non-limiting examples of such conversions are mentioned below.

Often, whether the expression of such a protein or polypeptide may be influenced by an AP2 transcription factor will depend upon the genetic make up of the gene involved, and in particular also on the promoter involved—e.g. that precedes—said gene. In principle, the invention may be used to modulate, and in particular to enhance, the expression of any and all native nucleotide sequence(s) or gene(s) that is/are preceded by, operably linked to and/or under the control of an expression regulating sequence—e.g. promoter—that contains a binding region for the transcription factor provided, e.g. such that the transcription factor may modulate, and in particular enhance, the expression of said gene.

However, the invention is not limited to such promoter-mediated modulation, but generally encompasses any mechanism via which a transcription factor may modulate the gene expression and/or the metabolism. For instance, this may involve binding to the DNA—e.g. genomic DNA—at other domains or regions usually close to (the part of the DNA encoding) the gene to be modulated, including but not limited to intron sequences, mRNA leader sequences, to regions of domains upstream—i.e. 3' compared to—the gene, etc. The modulation may also involve binding of the transcription factor to the part of the DNA encoding the gene to be modulated itself.

Some non-limiting examples of such expression regulation sequences/promoters that may be regulated by the transcription factors provided to the cell by the method of the invention include the promoters of the strictosidine synthase and tryptophan decarboxylase genes, as well as any other promoter of any other gene the expression of which is modulated—e.g. increased—by (over)expression of ORCA2 and/or ORCA3, including but not limited to the promoters of the Cpr, G10h, D4h, AS and/or DXS-genes.

As such, the invention may be used to regulate the expression of all genes that in the cell are natively under the control of such an expression regulating sequence; but also of genes that are not natively associated with such an expression regulating sequence, but that have been brought under the control of such a sequence. The latter may for instance include genes or other nucleotide sequences—homologous or heterologous to the plant (cell)—that are operably linked to such an expression regulating sequence as part of a genetic construct used to transform the plant (cell).

As further described below, the plant (cell) to which the (nucleotide sequence encoding) the AP2 transcription factor is provided—e.g. in which said factor is expressed in accordance with the method of the invention—may be present in or derived from any naturally occurring plant, including but not limited to any part, tissue or organ thereof. The plant cell may also be present in/derived from a transgenic plant.

For instance, the method of the invention may be applied to any plant—or part, tissue, organ or cell of such a plant—in which the metabolism is to be modulated, and in particular enhanced, e.g. for the (increased) production by the plant (cell) of one or more primary and/or secondary metabolites.

These plants may include, but not limited to, plants or plant cells of agronomically important crops, such as maize, rice, potato, wheat, cotton, soybean, grapevine, tomato, tobacco, canola, pepper, diverse herbs such as oregano, basilicum, mint.

It may also be applied to plants that produce valuable compounds, e.g. useful as for instance pharmaceuticals, as ajmalicine, vinblastine, vincristine, ajmaline, reserpine, rescinnamine camptothecine, ellipticine, quinine, and quinidine, taxol, morphine, scopolamine, atropine, cocaine, sanguinarine, codeine, genistein, daidzein, digoxin, colchicine, or as food additives, such as anthocyanins, vanillin; including but not limited to the (classes of) compounds mentioned above. Examples of such plants include, but not limited to, *Papaver* spp, *Rauvolfia* spp, *Taxus* spp, *Cinchona* spp, *Eschscholtzia californica, Camptotheca acuminata, Hyoscyamus* spp, *Berberis* spp, *Coptis* spp, *Datura* spp, *Atropa* spp, *Thalictrum* spp, *Peganum* spp.

The method of the invention may also be used to provide the plant or any part, tissue or organ thereof—including but not limited to leaves, stalks, stems, roots, petals, flowers, reproductive organs, as well as fruits, tubers, bulbs and/or seeds—with enhanced or otherwise modified taste, flavour, colour, scent or other desirable properties, e.g. due to increased levels of one or more metabolites that caused or otherwise associated with said properties.

Furthermore, as already mentioned, the method of the invention may be used to improve the stress resistance of a plant or plant cell, e.g. against the stress factors mentioned above. In one embodiment of the invention, such increased stress resistance may (at lest in part) be the result of/be caused by increased levels of certain metabolites in the plant (cell). For example, increased levels of proline, certain sugars or other "anti-freeze" components may lead to improved resistance against cold, whereas increased levels of certain other secondary metabolite may lead to increased resistance against UV-radiation, etc.

Also, such increased levels of certain metabolites—and in particular of certain secondary metabolites—may make the plant or any part, tissue, organ or material thereof—including but not limited to leaves, stalks, stems, roots, petals, flowers, reproductive organs, as well as fruits, tubers, bulbs and/or seeds—more resistant against biological pathogens and similar stress factors, including but not limited to bacteria, nematodes, insects and/or other pests, and/or herbivores. As is known, certain secondary metabolites—e.g. toxic or bad tasting metabolites—may defend the plant or plant material against damage or attack by such pathogens, in that they may make the plant or plant material less attractive as a food source. According to the invention, the level(s) of such metabolites may be (further) increased—e.g. compared to the native levels in the plant—to reduce or even prevent attack by such pathogens.

From the above, it will be clear that the method of the invention may more generally be used to enhance or otherwise influence any property of a plant that is caused by, or at least associated with, the levels of one or more secondary metabolites in the plant.

The method of the invention may also be used to provide (increased amounts of) one or more of the enzymes involved in the metabolic pathways in the plant, which may then be isolated from the plant and then put to further use(s).

According to the invention, the modulation of the metabolism—and thereby the enhanced production of the metabolites—may occur throughout the entire plant, or only in one or more specific parts, tissues, organs and or cells of the plant, including but not limited to leaves, stalks, stems, roots, petals, flowers, reproductive organs, as well as fruits, tubers, bulbs and/or seeds. The modulation of the metabolism may also occur during a specific phase of the plant life and/or plant development.

For this purpose, the transcription factor(s) of the invention may also be expressed in the plant cell under the control of a tissue specific promoter, e.g. specific for expression in leaves, stalks, stems, roots, petals, flowers, reproductive organs, fruits, tubers, bulbs and seeds; or under the control of a promoter that is specific for a certain phase of the development of the plant. The transcription factor(s) of the invention may also be expressed in the plant cell under the control of promoters that are activated by environmental signals, including but not limited to stress-related signals, light, exogenously added chemicals, pathogens or pathogenic signals. Examples of such promoters will be clear to the skilled person.

Thus, according to the invention, the cell to which the AP2 transcription factor is provided may be in the form of—i.e. may be present in—a cell culture (e.g. in vitro); or may be present in a plant in vivo, including but not limited to any tissue, part or organ of such a plant, such as the leaves, stalks, stems, roots, petals, flowers, reproductive organs, as well as fruits, tubers, bulbs and/or seeds.

In one specific embodiment, the one or more enzymatic conversion that are modulated by the expression of the AP2 transcription factors in accordance with the invention are enzymatic conversions that form part of the metabolic pathway(s) which in nature—e.g. in that plant (cell) as it natively occurs—are modulated or influenced by external stress.

In particular, such enzymatic conversion(s) may form part of the metabolic pathway(s) which in nature are modulated or influenced by the (extracellular) presence of one or more of the signalling molecules, including but not limited to jasmonic acid/jasmonate, ethylene, salicylic acid/salicylate, abscisic acid, gibberelic acids, nitrogen oxide, hydrogen peroxide, reactive oxygen species, gamma-amino-butyric-acid, fluctuations in intracellular calcium or other ion concentrations, phospholipids, etc.

More in particular, such enzymatic conversion(s) may form part of the metabolic pathway(s) which in nature are modulated or influenced by the (extracellular) presence of jasmonates, e.g. Again, these may be metabolic pathways leading to the formation of primary and/or to the formation of secondary metabolites.

Usually, in order to regulate one or more of the stress-related or stress factor-mediated enzymatic conversions/metabolic pathways, an AP2 transcription factor will be used that contains a single AP2 domain.

In particular, for this purpose, an AP2 transcription factor may be used that contains an AP2 domain of an AP2 transcription factor that in nature is regulated by external stress or the (extracellular) presence of one of the signalling molecules mentioned above; or that contains a mutant, analog, variant, part or fragment of such an naturally occurring AP2 domain. Such AP2 domains are described above.

More in particular, the AP2 transcription factor may be used that contains an AP2 domain of a transcription factor that is regulated by the (extracellular) presence of one or more jasmonates; or that contains a mutant, analog, variant, part or fragment of such an naturally occurring AP2 domain. Again, such AP2 domains are described above.

Thus, in another aspect, the invention relates to a method of modulating in a cell the expression of one or more genes involved in the biosynthesis of a metabolite or a precursor herefor, the method comprising inserting into the cell a nucleotide sequence coding for a transcription factor other than a transcription factor having a bHLH-type or a MYB-type DNA-binding domain, the nucleotide sequence is operably linked to at least one expression regulating sequence, and/or modifying the expression of a nucleotide sequence coding for such a transcription factor already present in the cell, the transcription factor is capable of regulating the expression of at least one gene coding for a gene product involved in the biosynthesis of said metabolite or precursor, and subjecting the cell to conditions where the inserted nucleotide sequence coding for a transcription factor is expressed or the expression of the nucleotide sequence already present in the cell is modulated.

In yet another aspect, the invention relates to a method of modulating the stress resistance of a cell, the method comprising inserting into the cell a nucleotide sequence coding for a transcription factor, the nucleotide sequence is operably linked to at least one expression regulating sequence, and/or modifying the expression of a nucleotide sequence coding for such a transcription factor already present in the cell, the transcription factor is capable of regulating the expression of at least one gene coding for a gene product involved in the biosynthesis of said metabolite or precursor, and subjecting the cell to conditions where the inserted nucleotide sequence coding for a transcription factor is expressed or the expression of the nucleotide sequence already present in the cell is modulated, the expression of said nucleotide sequence resulting in a modified responsiveness of the cell towards exogenous stress conditions.

In a further aspect, the invention relates to a recombinant cell having, relative to its parent cell, enhanced or reduced biosynthesis of a metabolite or a precursor therefor, and/or enhanced or reduced expression of a gene product involved in metabolite production, the cell comprising a nucleotide sequence coding for a transcription factor other than a transcription factor having a bHLH-type or a MYB-type DNA-binding domain, said transcription factor is capable of regulating the expression of at least one gene coding for a gene product involved in the metabolite production, said sequence is inserted into the cell and/or its expression is modified by operably linking it to a regulating sequence with which it is not natively associated.

According to the above aspects of the invention, the cell is preferably a plant cell, more preferably of a dicotyledonous species. In particular, the cell may be of a species selected from the group consisting of the Gentianales order and the Cornales order and/or of a species selected from an indole alkaloid producing species. Some non-limiting preferred examples thereof include species selected from the group consisting of species belonging to the Apocynaceae, Alangiaceae, Loganiaceae, Icacinaceae, Cornaceae and Rubiaceae families, and the genus *Catharanthus*, which is particularly preferred. Most preferred is a *Catharanthus roseus* cell.

The plant cell may be in the form of a cell culture (e.g. in vitro); or may be present in a plant tissue and/or in any part or organ of the plant (e.g. in vivo), including but not limited to the leaves, stalks, stems, roots, petals, flowers, reproductive organs, fruits, tubers, bulbs and seeds.

The nucleotide sequence coding for the transcription factor is preferably derived from a plant cell, more preferably from a cell derived from a dicotyledonous species.

In particular, the nucleotide sequence coding for the transcription factor may be derived from a cell of a species selected from the group consisting of the Gentianales order and the Cornales order and/or of a species selected from an indole alkaloid producing species. Some non-limiting preferred examples thereof include species selected from the group consisting of species belonging to the Apocynaceae, Alangiaceae, Loganiaceae, Icacinaceae, Cornaceae and Rubiaceae families, and the genus *Catharanthus*, which is particularly preferred. Most preferred is a *Catharanthus roseus* cell.

Preferably, the nucleotide sequence is a sequence coding for a transcription factor comprising at least one AP2 domain, including at least two AP2 domains and at least three AP2 domains.

For instance, the nucleotide sequence may be a sequence comprising at least one sequence coding for an AP2 domain selected from the group consisting of AP2 domains of SEQ ID NO:4, SEQ ID NO:5 and SEQ ID NO:6; and/or a sequence coding for an amino acid sequence selected from the group consisting of SEQ ID NO:4, SEQ ID NO:5 and SEQ ID NO:6.

Also, the nucleotide sequence may be a sequence coding for an amino acid sequence comprising an at least one AP2 domain having at least 40% homology, at least 50%, at least 60%, at least 70%, at least 80% or at least 90% homology to any of the at least one AP2 domains of SEQ ID NO:4, SEQ ID NO:5 and SEQ ID NO:6.

Alternatively, the nucleotide sequence may comprise at least one sequence coding for an AP2 domain of a sequence selected from the group consisting of SEQ ID NO:1, SEQ ID NO:2 and SEQ ID NO:3. The nucleotide sequence coding for the at least one AP2 domain may also be a mutant, allele or variant of a nucleotide sequence coding for an AP2 domain of a sequence selected from the group consisting of SEQ ID NO:1, SEQ ID NO:2, and SEQ ID NO:3.

The nucleotide sequence coding for a transcription factor may be a homologous nucleotide sequence or a heterologous nucleotide sequence, e.g. to the plant (cell) to which it is provided.

Preferably, the nucleotide sequence is operably linked to a regulating nucleotide sequence with which it is not natively associated, as further described below.

The metabolite is preferably a plant metabolite. As such it may be a primary plant metabolite, including but not limited to a primary plant metabolite selected from the group consisting of tryptophan or precursors therefor; terpenoid(s) including but not limited to geraniol; and precursors therefor.

The plant metabolite may also be a secondary plant metabolite. For instance, such a secondary metabolite may be selected from the group consisting of alkaloid compounds, phenolic compounds and terpenoid compounds, and in particular derived from a compound selected from the group consisting of tryptophan, tryptamine, tyrosine, lysine, ornithine, nicotinic acid, anthranilic acid and acetate, although the invention in its broadest sense is not limited thereto.

The secondary metabolite may also be an indole alkaloid such as a terpenoid indole alkaloid, including but not limited to pharmacologically active terpenoid indole alkaloids such ajmalicine, vinblastine, vincristine, ajmaline, reserpine, rescinnamine, camptothecine, ellipticine, quinine, and quinidine; and/or a precursor therefor, such as strictosidine.

The gene product involved in metabolite production may be a protein including but not limited to an enzyme, such as an enzyme involved in an alkaloid biosynthetic pathway. For instance, the enzyme may be selected from the group consisting of Anthranilate synthase (ASA); D-1 deoxyxylulose 5-phosphate synthase (DXS); Geraniol 10-hydroxylase (G10H); NADPH:cytochrome P450 reductase (CPR); Tryptophan decarboxylase (TDC); Strictosidine synthase (STR); Strictosidine β-D-glucosidase (SGD); Desacetoxyvindoline 4-hydroxylase (D4H); Acetyl-CoA:deacetylvindoline 4-O-acetyltransferase (DAT).

Preferably, the expression in the cell of one or more genes involved in the biosynthesis of a metabolite or a precursor herefor is enhanced or reduced relative to a cell into which a nucleotide sequence coding for a transcription factor is not inserted or which is without modified expression of the already present nucleotide sequence coding for a transcription factor.

For instance, in one embodiment, the expression in the cell of one or more genes involved in the biosynthesis of a metabolite or a precursor herefor may be enhanced by at least 10%, at least 25% or at least 100%, relative to a cell into which a nucleotide sequence coding for a transcription factor is not inserted or which is without modified expression of the already present nucleotide sequence coding for a transcription factor.

In another embodiment, the expression in the cell of one or more genes involved in the biosynthesis of a metabolite or a precursor herefor may be reduced by at least 10%, at least 25% or at least 50%, or at least 95%, relative to a cell into which a nucleotide sequence coding for a transcription factor is not inserted or which is without modified expression of the already present nucleotide sequence coding for a transcription factor.

In yet another aspect, the invention relates to a method of producing a metabolite including a plant secondary metabolite, the method comprising providing a recombinant cell as described above, cultivating said cell under conditions where the nucleotide sequence coding for the transcription factor regulating the expression of at least one gene coding for a gene product involved in the metabolite production is expressed, and recovering the metabolite.

In said method, the cell is preferably cultivated under conditions where at least one precursor for the metabolite is added in a form which can be assimilated by said cell.

However, this method also encludes cultivating and/or maintaining a plant that contains at least one recombinant cell as described above, and then recovering the metabolite from the plant, e.g. by harvesting the plant or at least a part, tissue or organ thereof and then recovering the metabolite from the plant material thus obtained.

The invention also relates to a method of constructing a recombinant cell as described hereinabove, said method comprising the steps of (i) identifying in a source cell a nucleotide sequence coding for a transcription factor other than a transcription factor having a bHLH-type or a MYB-type DNA-binding domain, said transcription factor is capable of regulating in the source cell the expression of at least one gene coding for a gene product involved in biosynthesis of a metabolite or a precursor therefor, (ii) isolating said nucleotide sequence; and (iii) inserting said isolated nucleotide sequence into a host cell comprising a gene coding for a gene product involved in biosynthesis of a metabolite or a precursor therefor, the insertion of said nucleotide sequence resulting in that the expression of the gene of the host cell is modulated relative to the expression level in a host cell not comprising the inserted nucleotide sequence.

In one embodiment of this method, at least two isolated nucleotide sequences are inserted into the host cell.

Another aspect of the invention relates to a polypeptide which includes an amino acid sequence having at least 40% homology including at least 50%, such as at least 60%, at least 70%, at least 80% and at least 90% to an amino acid sequence selected from the group consisting of SEQ ID NO:4, SEQ ID NO:5 and SEQ ID NO:6; and/or to a polypeptide having the amino acid sequence shown in SEQ ID NO:4, SEQ ID NO:5 or SEQ ID NO:6.

The invention also relates to an isolated nucleic acid molecule comprising a nucleotide sequence coding for an amino acid sequence selected from the group consisting of SEQ ID NO:4, SEQ ID NO:5 and SEQ ID NO:6; and/or to an isolated nucleic acid comprising a nucleotide sequence which is selected from the group consisting of SEQ ID NO: 1, SEQ ID NO:2 and SEQ ID NO:3 and a mutant, allele or variant hereof.

The invention also relates to a vector comprising a such nucleic acid molecule. Such a vector may further comprise at least one further sequence coding for a transcription factor.

Also, the invention relates to a host cell comprising a such a vector. Such a host cell may for instance be selected from the group consisting of a bacterium, a fungal cell, a yeast cell, an animal cell, a unicellular eukaryotic cell, an algae cell and a plant cell. Such a host cell may also be a cell suitable for transformation of another cell, such as an *Agrobacterium* cell.

The invention also relates to a plant comprising such a cell, e.g. in at least one part, organ or tissue.

In yet another aspect, the invention relates to a method of isolating a nucleotide sequence coding for a transcription factor not having a bHLH-type or a MYB-type DNA-binding domain, said transcription factor is capable of regulating in a cell the expression of at least one gene coding for a gene product involved in biosynthesis of a metabolite or a precursor therefor, the method comprising the steps of
(i) probing a cDNA or genomic library with a probe comprising at least a fragment of a nucleic acid as described above;
(ii) identifying a DNA clone that hybridises with said at least a fragment of a nucleic acid; and
(iii) isolating the DNA clone identified in step (ii) wherein the nucleic acid sequence is coding for all or a part of said transcription factor.

Furthermore, the invention relates to a method of isolating a nucleotide sequence coding for a transcription factor not having a bHLH-type or a MYB-type DNA-binding domain, said transcription factor is capable of regulating in a cell the expression of at least one gene coding for a gene product involved in biosynthesis of a metabolite or a precursor therefor, the method comprising the steps of
(i) synthesising an oligonucleotide primer set corresponding to at least a fragment of a sequence selected from the group consisting of SEQ ID NO:1, 2 and 3; and
(ii) amplifying cDNA or genomic DNA using said primer set in a polymerase chain reaction;

wherein the amplified nucleic acid fragment is coding for all or a part of said transcription factor to obtain a nucleotide sequence coding for a transcription factor not having a bHLH-type or a MYB-type DNA-binding domain.

According to one specific embodiment, the invention relates to an isolated nucleic acid which is a nucleotide sequence as shown in SEQ ID NO: 7 and a mutant, allele or variant hereof; and to the use of such an isolated nucleic acid sequence according to of SEQ ID NO:7 or a mutant, allele or variant thereof, for isolating a nucleotide sequence coding for a transcription factor not having a bHLH-type or a MYB-type DNA-binding domain, said transcription factor is capable of regulating in a cell the expression of at least one gene coding for a gene product involved in biosynthesis of a metabolite or a precursor therefor, the method comprising the steps as essentially described in Example 2 hereinbelow.

Also, in yet another aspect, the invention relates to a plant, plant cell or plant material that has been transformed with a genetic construct comprising at least one nucleotide sequence encoding at least one transcription factor, operably linked to an expression regulating sequence, in which the plant (cell), genetic construct, transcription factor and expression regulating sequence may be as defined above.

Preferably, the expression regulating sequence is heterologous to the plant (cell) and/or is an expression regulating sequence with which the at least one nucleotide sequence that encodes said at least one transcription factor is not natively associated.

Preferably, in such a transformed plant cell or transformed plant (e.g. in at least one part, organ, tissue or cell thereof),
the intracellular level(s) of one or more metabolites are enhanced, the intracellular levels of one or more (other) metabolites are reduced; or a combination thereof, e.g. as described above and/or by the amounts indicated above; and/or
the expression of one or more genes involved in the biosynthesis of a metabolite or a precursor herefor are enhanced; the expression in the cell of one or more genes involved in the biosynthesis of a metabolite or a precursor herefor are reduced; or a combination thereof, e.g. as described above and/or by the amounts indicated above.

The invention also relates to cultivating material for and/or of such a transformed plant, including but not limited to seed, tubers, fruits, roots, bulbs and/or seedlings.

The invention also relates to descendants of such a transformed plant, which may for instance be obtained by sexual or asexual reproduction, including but not limited to standard cultivation techniques, starting from a plant transformed according to the method of the invention. Preferably, in (at least one cell, part, tissue or organ of) such a descendant,
the intracellular level(s) of one or more metabolites are enhanced, the intracellular levels of one or more (other) metabolites are reduced; or a combination thereof, e.g. as described above and/or by the amounts indicated above; and/or
the expression of one or more genes involved in the biosynthesis of a metabolite or a precursor herefor are enhanced; the expression in the cell of one or more genes involved in the biosynthesis of a metabolite or a precursor herefor are reduced; or a combination thereof, e.g. as described above and/or by the amounts indicated above;

compared to the corresponding native (e.g. non-transformed) plant.

Also, the invention relates to a method for providing a transformed plant or a descendant of such a transformed plant, in which, compared to the corresponding native (e.g. non-transformed) plant,
the intracellular level(s) of one or more metabolites are enhanced, the intracellular levels of one or more (other) metabolites are reduced; or a combination thereof, e.g. as described above and/or by the amounts indicated above; and/or
the expression of one or more genes involved in the biosynthesis of a metabolite or a precursor herefor are enhanced; the expression in the cell of one or more genes involved in the biosynthesis of a metabolite or a precursor herefor are reduced; or a combination thereof, e.g. as described above and/or by the amounts indicated above;

said method comprising the steps of:
(a) transforming a plant, plant cell or plant material with a genetic construct comprising at least one nucleotide sequence encoding at least one transcription factor, operably linked to an expression regulating sequence (b) optionally cultivating the plant, plant cell or plant material into a mature plant; and/or (c) optionally providing one or more further generation of the transformed plant of step (a) and/or step (b) by sexual or asexual reproduction, including but not limited to standard plant cultivation and/or plant breeding techniques;

in which the plant (cell), genetic construct, transcription factor and expression regulating sequence may be as defined above In yet another aspect, the invention relates to plant material of and/or obtained from a plant as described above.

Also, the invention relates to a metabolite, in particular a primary or secondary plant metabolite (e.g. as described above), obtained via the method described above and/or from a plant, plant cell and/or plant material as described above; or from a descendant of such a plant.

Other aspect, embodiments, advantages and possible applications of the invention will become clear from the description hereinbelow.

DETAILED DISCLOSURE OF THE INVENTION

A major objective of the present invention is to provide a method of modulating in a cell the expression of one or more genes involved in the biosynthesis of a metabolite or a precursor for the metabolite. As mentioned above, the method comprises that a nucleotide sequence coding for a transcription factor other than a transcription factor having a bHLH-type or a MYB-type DNA-binding domain is inserted into the cell such that the nucleotide sequence is operably linked to at least one expression regulating sequence, and/or that the expression of a nucleotide sequence coding for such a transcription factor already present in the cell is modified.

In the present context, the term "modulating" with respect to (the expression of) a gene refers to any change in the level of expression of a gene involved in the biosynthesis of a metabolite or a precursor for the metabolite relative to the level of expression in a corresponding cell type not having a modulated expression of the same gene or genes, i.e. in the wild type state. It will be appreciated that "modulating" may imply both reduced and enhanced levels of expression relative to that found in the wild type cell, e.g. as outlined above.

With respect to metabolites—including but not limited to primary metabolites, secondary metabolites and/or precursors therefor, as well as intermediates of metabolic routes leading to such metabolites—"modulating" refers to any change in the level of said metabolite or a precursor for the metabolite relative to the level thereof in a corresponding cell in the wild type state. It will be appreciated that "modulating" may imply both reduced and enhanced levels of said metabolites relative to those found in the wild type cell, e.g. as outlined above.

As used herein the term "cell" encompasses any eukaryotic or prokaryotic cell. Thus, cells include bacterial cells, fungal cells including yeast cells, animal cells, dictyostelium cells, algae cells, and plant cells. The cell may be in the form of a single, isolated cell or it may in the form of multicellular tissues including an animal or a plant organ, plant callus tissues and an entire animal or plant.

The expression "nucleotide sequence coding for a transcription factor" is used herein encompasses any nucleotide sequence coding for a transcription factor which does not comprise a bHLH-type or a MYB-type DNA-binding domain. It will be appreciated that such a coding sequence may consist solely of coding DNA (ORFs) or, when it is derived from a eukaryotic cell, it may include introns.

In this context, the expression "transcription factor" refers to a protein that in a sequence-specific manner binds to DNA by recognising specific elements located in the promoter and/or enhancer regions of the corresponding genes. The binding of such transcription factors to the specific DNA elements modulates the activity of other components of the transcription machinery including basal transcription factors and RNA polymerase, and thereby positively or negatively modulates the initiation of mRNA synthesis. Transcription factors have in common that they comprise DNA binding domains capable of binding to specific elements of their target genes.

Transcription factors are classified in families based on conserved features of their DNA-binding domain. Within each family, DNA-binding domains are similar, but not identical. Small differences in amino acid sequences can cause significant differences in the DNA sequence requirement for binding. As a result of these differences within a family, it is impossible to reliably predict whether a certain DNA sequence will bind a certain transcription factor family member with high affinity, and conversely, based on the amino acid sequence of a certain transcription factor family member it is impossible to reliably predict which sequence it will bind with high affinity.

Transcription factors have a modular structure, consisting of domains with specialised functions, such as sequence-specific DNA binding, transcriptional activation, interaction with themselves or other proteins. These domains are in many cases functional even when fused to heterologous proteins. ORCA proteins contain the AP2-type DNA-binding domain. Since they activate transcription, it can be concluded that they contain an activation domain. It is conceivable that in e.g. *Catharanthus* cells the activity of AP2 domain class transcription factors is modulated via post-translational modifications (phosphorylation, myristoylation etc.) via interaction with other proteins, or combinations thereof. The activity of AP2 domain class transcription factors can be modulated using recombinant DNA techniques. The objectives could be to make the activity of the transcription factors independent from post-translational modifications, to enhance their activity, or to make the activity dependent on convenient inducing conditions. These objectives can be accomplished via single amino acid modifications, deletions of several amino acids, fusions with other proteins or protein domains, or combinations thereof. AP2 domain-containing transcription factors may be constitutively targeted to the nucleus by addition of a nuclear localisation signal. Strong activation domains could be fused to the transcription factors in addition to or as a replacement for existing activation domains. Such activation domains include the Herpes simplex virus VP16 domain, the GAL4 activation domain, or synthetic activation domains known to be active in plants. Inducibility of transcription factor activity can be achieved via fusion with mammalian steroid hormone receptor domains. The resulting chimera can be activated by steroid hormone addition.

In accordance with the above method of the invention, the nucleotide sequence coding for the transcription factor is operably linked to at least one expression regulating sequence. In the present context, the term "operably linked" refers in general to a situation where a first nucleic acid sequence is linked with a second nucleic acid sequence and the first nucleic acid sequence is placed in a functional relationship with the second nucleic acid sequence. For instance, a promoter is operably linked to a coding sequence if the promoter affects the transcription or expression of the coding sequence (i.e. that the coding sequence is under the transcriptional control of the promotor). Generally, operably linked nucleic acid sequences are contiguous and, where necessary to join two protein coding regions, in reading frame. However, operably linked nucleic acid sequences may also be in a functional relationship without being contiguous. Typical examples of "expression regulating sequences" include promoter sequences, enhancer sequences, translation leader sequences, sequences coding for anti sense RNA and 3' non-coding sequences.

It will be understood that the term "promoter" includes both constitutive promoters and regulatable promoters. In respect of the latter type of promoters, the regulation is typically conferred by exogenous (extrinsic) or endogenous (intrinsic) factors including physical factors such as the temperature or light, chemical factors including the pH, the presence of inducer substances, absence/presence of nutrient compounds in the cell environment. Most preferably, a promoter should be "operable" in the cell to which it is provided, by which is meant that the promoter should be capable of causing and/or regulating in said cell the expression of one or more nucleotide sequences (e.g. genes) that are operably linked (as defined above) to said promoter. Such nucleotide sequences should be understood as being "under the control of" said promoter.

In one presently preferred embodiment, the cell in which the expression of one or more genes involved in the biosynthesis of a metabolite or a precursor herefor is a plant cell.

The term "plant cell" as used herein include protoplasts, fused cells, gamete producing cells, undifferentiated and differentiated cells, and cells which regenerate into whole plants. Accordingly, a seed comprising multiple plant cells capable of regenerating into a whole plant, is included in the definition of "plant cell". In useful embodiments, the plant cell is in the form of a cell culture.

As used herein, the term "plant" refers to any organism of the kingdom Plantae, including Bryophytes, Pteridophytes, Spermatophytes (Gymnosperms and Angiosperms, including monocotyledonous and dicotyledonous), thallophytes (including algae such as Chrysophyta, Pyrrophyta, Euglenophyta, Rhodophyta, Phaeophyta and Clorophyta), a whole plant, any plant part or propagule thereof, seed or hybrid progeny and descendants, a plant cell, a multiplicity of plant cells such as e.g. plant tissues, and plant cells in the form of a cell culture. Plantlets are also included within the meaning of "plant". In specific embodiments, the method relates to plant cells of a species of the Gentianales order or the Cornales order such as a species selected from an indole alkaloid producing species. Such species include species of the Apocynaceae, Alangiaceae, Loganiaceae, Icacinaceae, Cornaceae and Rubiaceae families. One particularly interesting genus of the Apocynaceae family is the genus *Catharanthus* including the species *C. roseus, C. coriaceus, C. lanceus, C. longifolius, C. ovalis, C pusillus, C. scitulus* and *C. trichophyllus*.

In accordance with the invention, the nucleotide sequence coding for a transcription factor as defined above can be derived from any cell type comprising such a sequence. Particularly useful sources for such sequences are plant cells of any of the above types and forms.

In one interesting embodiment, the nucleotide sequence coding for a transcription factor is a sequence coding for a transcription factor comprising at least one AP2 domain. Transcription factors comprising such a DNA-binding domain are generally referred to as AP2/EREBP transcription factors which constitute a class of transcription factors that at present have only been found in plants. They posses two features that are typical for transcription factors, namely sequence-specific DNA binding capability and ability to activate (or repress) transcription. (Riechmann and Meyerowitz, 1998).

Sequence similarity among the AP2/EREBP proteins is mostly limited to the AP2 DNA-binding domain (APETALA2 domain) itself (approximately 68 aa), which is the only region conserved among all proteins of the family. The distinguishing characteristic of proteins of the AP2/EREBP family is that they contain either one or two AP2 domains. Thus this family can be divided into two subfamilies based on whether the proteins contain one or two AP2 domains, the EREBP subfamily and the AP2 subfamily, respectively. The AP2 domains in the AP2 subfamily are more related among members of this subfamily than to the AP2 domains of proteins of the EREBP subfamily and vice versa. However, many characteristics are common to the AP2 domains from both subfamilies. Two conserved segments are found within each AP2 domain, which have been referred to as the YRG element, and the RAYD element. The amino terminal part of the AP2 domains (the YRG element) is basic and hydrophilic. The carboxy terminal RAYD element contains a central region that, in almost all AP2 domains, is predicted to adopt the configuration of an alpha-helix of amphipathic character. Solution structure determination of one particular *Arabidopsis* AP2 domain protein revealed that the YRG element and the next 20 to 30 amino acids form three anti-parallel β-sheets that contact the DNA, whereas the RAYD element indeed adopts an α-helical structure as predicted.

As used herein an AP2 DNA-binding domain is defined as an amino acid sequence having at least 35% amino acid residue identity such as at least 45%, at least 55%, at least 65%, at least 75%, at least 85%, at least 95% or at least 98% residue identity to any of the AP2 domains described in Riechmann and Meyerowitz (1998). However, in the present context, any amino acid sequence having similarity to any of the two conserved segments, the YRG element and the RAYD element as defined by Riechmann and Meyerowitz (1998) are encompassed by the invention and considered as having an AP2 DNA-binding domain.

In another embodiment, the transcription factor as used herein includes at least two AP2 domains such as at least three AP2 domains.

In specific embodiments, the method is based on the use of a transcription factor coding sequence comprising at least one sequence coding for an AP2 domain selected from AP2 domains of SEQ ID NO:4, SEQ ID NO:5 or SEQ ID NO:5 or a sequence coding for an amino acid sequence selected from SEQ ID NO:4, SEQ ID NO:5 or SEQ ID NO:6.

It will be appreciated that in accordance with the invention, a functional AP2 domain class transcription factor can be derived from a source cell naturally containing such a factor. However, it is contemplated that a transcription factor that is functional in accordance with the invention can be constructed either by isolating one or more AP2 domains from a naturally occurring transcription factor and combining it with an amino acid sequence with which it is not naturally associated. Alternatively, an AP2 domain may be constructed synthetically and combined with further amino acids to provide a transcription factor active polypeptide.

In accordance with the method of the invention, the nucleotide sequence may be a sequence coding for an amino acid sequence comprising an at least one AP2 domain having at least 40% homology, at least 50%, at least 60%, at least 70%, at least 80% or at least 90% homology to any of the at least one AP2 domains of SEQ ID NO:4, SEQ ID NO:5 and SEQ ID NO:6.

As used herein, the term "homology" refers to homology at the amino acid level both in terms of amino acid identity and similarity. Similarity allows for "conservative variation", i.e. substitution of one hydrophobic residue such as isoleucine, valine, leucine or methionine with another hydrophobic residue, or the substitution of one polar residue with another polar residue, such as arginine with lysine, glutamic acid with aspartic acid, or glutamine with asparagine. In the present context, similarity is defined and determined using the present version of the BLAST program (Altschul et al, 1997).

In other specific embodiments, the nucleotide sequence coding for the transcription factor comprises at least one AP2 domain-coding sequence selected from SEQ ID NO:1, SEQ ID NO:2 and SEQ ID NO:3 or the nucleotide sequence coding for the at least one AP2 domain is a mutant, allele, derivative or variant of a nucleotide sequence coding for an AP2 domain of a sequence selected SEQ ID NO:1, SEQ ID NO:2 and, SEQ ID NO:3.

In the present context, the terms "mutant", "allele", "derivative" or "variant" may be by one or more of addition, insertion, deletion or substitution of one or more nucleotides in the nucleotide sequence, leading to the addition, insertion, deletion or substitution of one or more amino acids in the encoded polypeptide while substantially maintaining biological activity of the encoded polypeptide. Also included are changes in the nucleotide sequences which make no difference to the encoded amino acid sequence.

Variant, allelic, mutant or derivatised nucleotide sequences can e.g. be produced by standard DNA mutagenesis techniques or by chemically synthesising the variant DNA molecule. Such variants, alleles, mutants or derivatives do not change the reading frame of the protein-coding region of the nucleotide sequence and encode a protein having no or only minor changes in its biological function.

In accordance with the method of the invention, the nucleotide sequence coding for a transcription factor, the expression of which is modulated, is either a homologous nucleotide sequence or a heterologous nucleotide sequence. As used herein, the term "homologous" refers generally to a nucleotide sequence present or originating in the same species and the term "heterologous" refers correspondingly to a sequence originating from a different species.

It will be appreciated that when the sequence is a homologous sequence, the expression of the sequence may be modulated while it is in its natural location in the cell, but it is also contemplated that a homologous coding nucleotide sequence may be translocated within the cell of origin. Whether homologous or heterologous, the transcription factor-encoding nucleotide sequence may be operably linked to a regulating nucleotide sequence with which it is not natively associated.

In one step of the above method, a nucleotide sequence coding for a transcription factor is inserted into the cell. The insertion can be carried out using any conventional methods of inserting nucleic acid into cells. Such transformation methods include as examples microprojectile bombardment, microinjection, electroporation, liposome mediated uptake and transformation by means of a disarmed Ti-plasmid vector carried by *Agrobacterium*. Numerous plant transformation vectors are available for plant transformation, and genes encoding transcription factors according to the invention can be used in conjunction with any such vectors. The selection of vectors for use will depend upon the preferred transformation technique and the target species for transformation. For certain target species, different antibiotic or herbicide selection markers may be preferred. Selection markers used routinely in transformation include the nptll gene which confers resistance to kanamycin and related antibiotics the bar gene which confers resistance to the herbicide phosphinothricin, the hph gene which confers resistance to the antibiotic hygromycin, the dhfr gene which confers resistance to methotrexate and the Tdc gene, which confers resistance to 4-methyltryptophan.

Also many vectors are available for plant transformation using *Agrobacterium tumefaciens*. These typically carry at least one T-DNA border sequence and include vectors such as pBIN19, pCAMBIA, pMOG402 and pMOG22. Typical vectors contain DNA borders for *Agrobacterium*-mediated transformation, the RK2-derived tra function for mobilisation between *E. coli* and other hosts, and the OriT and OriV functions that are also from RK2. They usually contain a polylinker that is suitable for the cloning of plant expression cassettes containing their own regulatory signals.

Transformation without the use of *Agrobacterium tumefaciens* can also be performed which circumvents the requirement for T-DNA sequences in the chosen transformation vector, and consequently vectors lacking these sequences can be utilised in addition. The choice of vector depends largely on the preferred selection for the species being transformed.

In accordance with the invention, gene sequences intended for expression in transgenic plants can be assembled in expression cassettes behind a suitable promoter and upstream of a suitable transcription terminator. These plant expression cassettes can then by use of standard methods be transferred to the plant transformation vectors described above.

The selection of a promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and this selection will reflect the desired location of expression of the transgene. Alternatively, the selected promoter may drive expression of the gene under a light-induced or other temporally regulated promoter. A further alternative is that the selected promoter be chemically and/or physically regulated. This provides the possibility of inducing expression of the transgene only when desired and caused by treatment with a chemical and/or physical inducer.

A variety of transcriptional terminators are available for use in expression cassettes. They are responsible for the termination of transcription beyond the transgene and its correct polyadenylation. Appropriate transcriptional terminators are those which are known to function in plants and include the CAMV 35S terminator, the tml terminator, the nopaline synthase terminator, and the pea rbcs E9 and 3C terminators. They can be used in both monocotyledons and dicotyledons.

It is a further objective of the present invention to provide the means of enhancing biosynthesis of metabolites in a cell as defined above. Although it is contemplated that the discoveries on which the present invention is based is applicable to any of these cell types and to any metabolite synthesised in such cells by genes the expression of which are regulated by transcription factors as defined herein, the method of the invention is presently preferred for the optimisation of biosynthesis of plant metabolites, in particular secondary metabolites including those mentioned above. However, It is also contemplated that the method of the invention can be used for the biosynthesis of novel and presently unknown metabolites, including novel plant secondary metabolites.

Thus, the secondary metabolites the biosynthesis of which can be enhanced using the method of the invention include but are not limited to alkaloid compounds including indole alkaloids such as terpenoid indole alkaloids (TIAs), phenolic compounds and terpenoid compounds. A review of secondary plant metabolites is included in e.g. Phytochemical Dictionary, A Handbook of Bioactive Compounds from Plants, edited by Harborne and Baxter, Taylor & Francis, London and Washington, D.C. In useful embodiments, the secondary metabolites are alkaloids derived from compounds such as tryptophan (indole alkaloids including vincristine and vinblastine), tyrosine (isoquinoline alkaloids including berberine, berbamine and stephamine), lysine (quinolizidine alkaloids including lupamine and sparteine), ornithine (tropane alkaloids including scopolamine and atropine), nicotinic acid, anthranilic acid and acetate.

Primary metabolites the biosynthesis of which can be enhanced using the method of the invention include but are not limited to tryptophan and precursors thereof as well as terpenoids and precursors thereof.

In accordance with the invention the transcription factor as used in the above method is capable of regulating the expression of at least one gene coding for a gene product involved in metabolite biosynthesis. Typically, such a gene product is a protein such as an enzyme. In a useful embodiments the enzyme is involved in an alkaloid biosynthetic and precursor pathways including an enzyme that is selected from the group consisting of Anthranilate synthase (ASA); D-1 deoxyxylulose 5-phosphate synthase (DXS); Geraniol 10-hydroxylase (G10H); NADPH:cytochrome P450 reductase (CPR); Tryptophan decarboxylase (TDC); Strictosidine synthase (STR); Strictosidine β-D-glucosidase (SGD); Desacetoxyvindoline 4-hydroxylase (D4H); Acetyl-CoA:deacetylvindoline 4-O-acetyltransferase (DAT).

As mentioned above, the present invention has made it possible to modulate in a cell the expression of one or more genes involved in the biosynthesis of a metabolite or a precursor for the metabolite. Although in presently preferred embodiments the expression of the gene or genes is enhanced with the objective of improving the yield of a desired metabolite, it is also contemplated that it may, under certain conditions, be advantageous to be able to reduce the expression of one or more biosynthetic genes. The enhancement, or alternatively, the reduction of the gene expression, relative to a cell into which a nucleotide sequence coding for a transcription factor is not inserted or which is without modified expression of the already present nucleotide sequence coding for a transcription factor, is obtained by modifying the expression level of the nucleotide sequence coding for the transcription factor as defined herein.

In a specific embodiment, the expression in the cell of one or more genes involved in the biosynthesis of a metabolite or a precursor herefor is enhanced by at least 10%, at least 25%, at least 50%, at least 75% or at least 100%, relative to a cell into which a nucleotide sequence coding for a transcription factor is not inserted or which is without modified expression of the already present nucleotide sequence coding for a transcription factor. It will be understood that "enhancement of gene expression" is related to the increase in biosynthesis of the metabolite. It is also contemplated that the enhancement of gene expression can be higher such as by a factor of at least 1.5 including at least 2, at least 5 or at least 10.

The enhancement of the expression of one or more genes involved in the biosynthesis of a metabolite or a precursor herefor can, in accordance with the invention, be achieved in either of two ways. One way is by inserting into the cell a nucleotide sequence coding for a transcription factor as defined herein and operably linking it to at least one expression regulating sequence, the cell comprising at least one target biosynthetic gene for the inserted transcription factor. An alternative way is by modifying the expression of a nucleotide sequence coding for such a transcription factor already present in the cell. In either of such ways, the modification results in that the transcription factor is produced in higher amounts than in a cell of a corresponding type that is not modified by insertion of a transcription factor-encoding sequence or by modifying the expression of such a sequence already present in the cell. It is evident that the expression of the biosynthetic gene is enhanced in a cell type not previously containing the transcription factor provided the cell contains a biosynthetic gene comprising a target sequence for the transcription factor. However, the expression level of an inserted transcription factor-encoding nucleotide sequence can also be enhanced by in vivo or in vitro modifications.

In accordance with the invention, enhancement of the expression of a transcription factor encoding sequence ("up-regulation") can be obtained by any known technique leading to enhanced gene expression. As an example, the coding sequence can be linked to a stronger promoter or the native promoter of the sequence can be structurally modified so as to improve its promoter strength. The expression may also be enhanced by modifying any other regulating sequence operably linked to the coding sequence e.g. by mutation. An alternative approach is to modify the nucleotide sequence of the transcription factor-encoding sequence.

A number of different sequences have been found to enhance gene expression from within the transcriptional unit and these sequences can thus be used in conjunction with the transcription factor-encoding nucleotide sequences according to the invention to increase their expression in transgenic plants. Various intron sequences have been shown to enhance expression, particularly in monocotyledonous cells. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus, Maize Chlorotic Mottle Virus and Alfalfa Mosaic Virus have been shown to be effective in enhancing expression.

Where the expression of the at least one gene involved in the metabolite biosynthesis is reduced ("down-regulated"), the reduction is typically by at least 10%, at least 25% or at least 50%, or at least 95%, relative to a cell into which a nucleotide sequence coding for a transcription factor is not inserted or which is without modified expression of the already present nucleotide sequence coding for a transcription factor. It is also contemplated that the reduction of gene expression can be higher such as by a factor of at least 1.5 including at least 2, at least 5 or at least 10.

Down-regulation of the expression of the transcription factor-encoding sequence can be obtained in several ways. Thus, as an example the expression is reduced by using anti-sense technology or "sense regulation" ("co-suppression"). In using anti-sense genes or partial gene sequences to down-regulate gene expression, a nucleotide sequence is placed under the control of a promoter in "reverse orientation" such that transcription yields RNA which is complementary to normal mRNA transcribed from the sense strand of the target gene. An alternative approach is to use a copy of all or part of the target gene inserted in sense, that is the same, orientation as the target gene, to achieve reduction in expression of the target gene by co-suppression.

In another aspect of the invention there is provided a method of modulating the stress resistance of a cell, the method comprising inserting into the cell a nucleotide sequence coding for a transcription factor, the nucleotide sequence is operably linked to at least one expression regulating sequence, and/or modifying the expression of a nucleotide sequence coding for such a transcription factor already present in the cell, the transcription factor is capable of regulating the expression of at least one gene coding for a gene product involved in the biosynthesis of said metabolite or precursor, and subjecting the cell to conditions where the inserted nucleotide sequence coding for a transcription factor is expressed or the expression of the nucleotide sequence already present in the cell is modulated, the expression of said nucleotide sequence resulting in a modified responsiveness of the cell towards exogenous stress conditions.

In the present context, the expression "exogenous stress conditions" should be understood as meaning any condition that results in that the growth and function of the cell is impaired relative to optimum conditions for growth and function. In relation to a plant, such stress conditions include attack of the plant by a pathogen, abiotic adverse environmental conditions like cold or heat and drought (osmotic stress), insufficient or excess supply of nutrient compounds, insufficient or excess levels of plant hormones, UV light, low light levels and suboptimal pH conditions.

In accordance with the invention the cell having modulated stress resistance may be any of the cell types as mentioned above in which at least one gene involved in the biosynthesis of a metabolite or a precursor for the metabolite is modulated as described above and to which there is referred. In particularly useful embodiments the cells having modulated stress resistance are plant cells of the above types and species including whole transgenic plants.

In accordance with the present method of modulating stress resistance, the expression of at least one biosynthetic gene is modulated by modifying the expression of any type of transcription factors that has a target sequence in the cell. Thus, in one embodiment, the nucleotide sequence coding for a transcription factor is a sequence coding for a transcription factor comprising at least one AP2 domain, including at least two AP2 domains or at least three AP2 domains of any of the above types and having any of the above sequences including such sequences that are operably linked to a regulating nucleotide sequence with which it is not natively associated.

In accordance with the invention the plant cell which is modified to have enhanced stress resistance may be modulated in its expression of any of the above metabolites or gene products involved in metabolite biosynthesis.

Similar to what is described above in the context of the method of modulating in a cell the expression of one or more genes involved in the biosynthesis of a metabolite or precursor herefor, the present method includes that the expression in the cell of one or more genes involved in the biosynthesis of a metabolite or a precursor herefor is enhanced or reduced relative to a cell into which a nucleotide sequence coding for a transcription factor is not inserted or which is without modified expression of the already present nucleotide sequence coding for a transcription factor. Such an enhancement or reduction is achieved mutatis mutandis as it is described for the former method.

In a further aspect, the invention provides a recombinant cell having, relative to its parent cell, enhanced or reduced biosynthesis of a metabolite or a precursor therefor, and/or enhanced or reduced expression of a gene product involved in metabolite production, the cell comprising a nucleotide sequence coding for a transcription factor other than a transcription factor having a bHLH-type or a MYB-type DNA-binding domain, said transcription factor is capable of regulating the expression of at least one gene coding for a gene product involved in the metabolite production, said sequence is inserted into the cell and/or its expression is modified by operably linking it to a regulating sequence with which it is not natively associated. In useful embodiments such a cell is a plant cell of any of the types and species as mentioned above and modified as also described above. In other useful embodiments such a cell is a cell wherein at least one pathway leading to the biosynthesis of at least one precursor for the metabolite can be stimulated in the cell in the presence of an inducing agent. Such inducing agents include chemical compounds (e.g. an elicitor, jasmonate and a hormone) and physical factors (e.g. light, temperature, pH and shear stress).

In another aspect, the invention provides a method of producing a metabolite including a plant secondary metabolite, the method comprising providing a recombinant cell as described above, cultivating said cell under conditions where the nucleotide sequence coding for the transcription factor regulating the expression of at least one gene coding for a gene product involved in the metabolite production is expressed, and recovering the metabolite. The cultivation of the recombinant cell of the invention is carried out using any conventional cultivation media and any conventional culturing methods for the particular type of cell. Such conventional culturing methods also includes methods where the cell is cultivated under conditions where at least one precursor for the metabolite is added in a form which can be assimilated by the cell. In useful embodiments such precursors may include compounds such as e.g. tryptophan, tyrosine, lysine, ornithine, nicotinic acid, anthranilic acid and acetate. Also included are culturing methods where the recombinant cell of the invention is further genetically modified in order to stimulate the production of a precursor for the metabolite, and methods wherein a compound which stimulates the production of a precursor for the metabolite is added to the cell in form which can be assimilated by the cell.

In a particular aspect of the invention there is provided a method of constructing a recombinant cell as described above, the method comprising the steps of (i) identifying in a source cell at least one nucleotide sequence coding for a transcription factor other than a transcription factor having a bHLH-type or a MYB-type DNA-binding domain, said transcription factor(s) is/are capable of regulating in the source cell the expression of at least one gene coding for a gene product involved in biosynthesis of a metabolite or a precursor therefor, (ii) isolating said nucleotide sequence and (iii) inserting said isolated nucleotide sequence(s) into a host cell comprising a gene coding for a gene product involved in biosynthesis of a metabolite or a precursor therefor, the insertion of said nucleotide sequence(s) resulting in that the expression of the gene of the host cell is modulated relative to the expression level in a host cell not comprising the inserted nucleotide sequence(s).

In useful embodiments, at least two isolated nucleotide sequences are inserted into the host cell.

A typical non-limiting example of how the method is carried out is described in the below examples.

In further aspects, the invention provides an isolated nucleic acid molecule comprising a nucleotide sequence coding for an amino acid sequence selected from the group consisting of SEQ ID NO:4, SEQ ID NO:5 and SEQ ID NO:6 including such an isolated nucleic acid that comprises a nucleotide sequence which is selected from the group consisting of SEQ ID NO:1, SEQ ID NO:2 and SEQ ID NO:3 and a mutant, allele or variant hereof and a polypeptide which includes an amino acid sequence having at least 40% homology including at least 50%, such as at least 60%, at least 70%, at least 80% and at least 90% to an amino acid sequence selected from the group consisting of SEQ ID NO:4, SEQ ID NO:5 and SEQ ID NO:6.

There is also provided a polypeptide having the amino acid sequence shown in SEQ ID NO:4, SEQ ID NO:5 or SEQ ID NO:6.

The invention also relates to a vector comprising a nucleic acid molecule as defined above including such as a vector that comprises at least one further sequence coding for a transcription factor and to a host cell comprising such a vector. The host cell is selected from the group consisting of a bacterial cell, a fungal cell, a yeast cell, an animal cell, a unicellular eukaryotic cell, an algae cell and a plant cell.

As mentioned above, the invention also provides a method of isolating a nucleotide sequence coding for a transcription factor not having a bHLH-type or a MYB-type DNA-binding domain. A typical example of a probe that is useful in such a method is a fragment of a nucleic acid as shown in SEQ ID NO:1, SEQ ID NO:2 and SEQ ID NO:3 and a mutant, allele or variant hereof.

The invention also provides a method of isolating a nucleotide sequence coding for a transcription factor not having a bHLH-type or a MYB-type DNA-binding domain by using a nucleotide sequence as shown in SEQ ID NO:1, 2 and 3 in a polymerase chain reaction.

In other aspects, there are provided an isolated nucleic acid having the nucleotide sequence as shown in SEQ ID NO:7 and a mutant, allele or variant hereof, and a method using this nucleic acid sequence for isolating a nucleotide sequence coding for a transcription factor not having a bHLH-type or a MYB-type DNA-binding domain.

Figure 2:
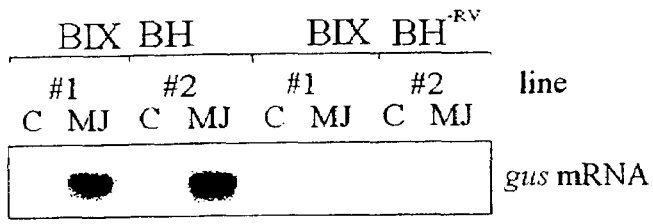
Figure 3:
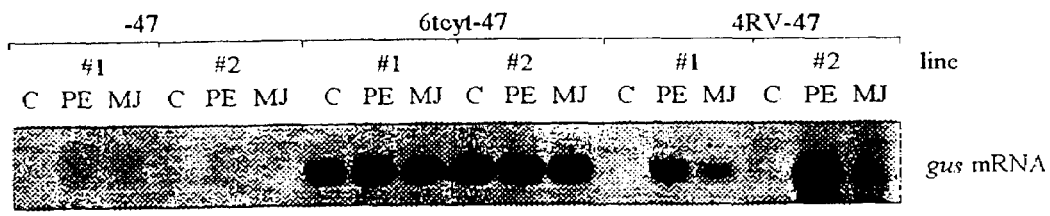
Figure 3:
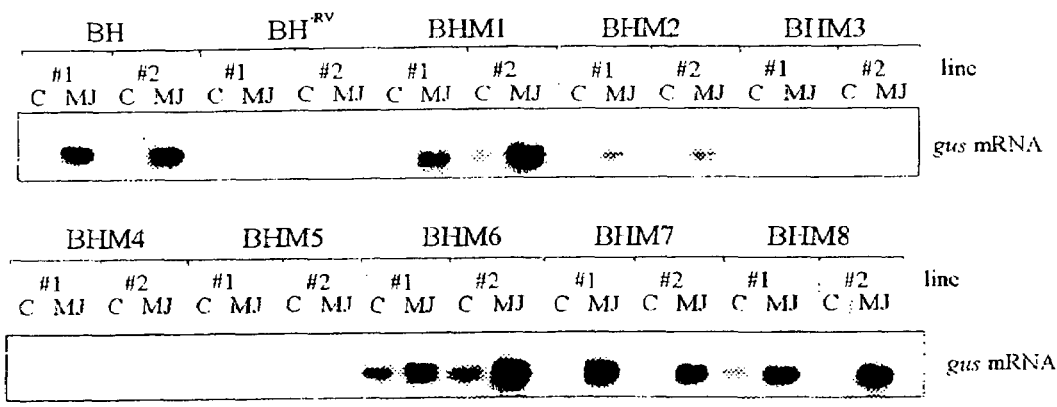
Figure 4:
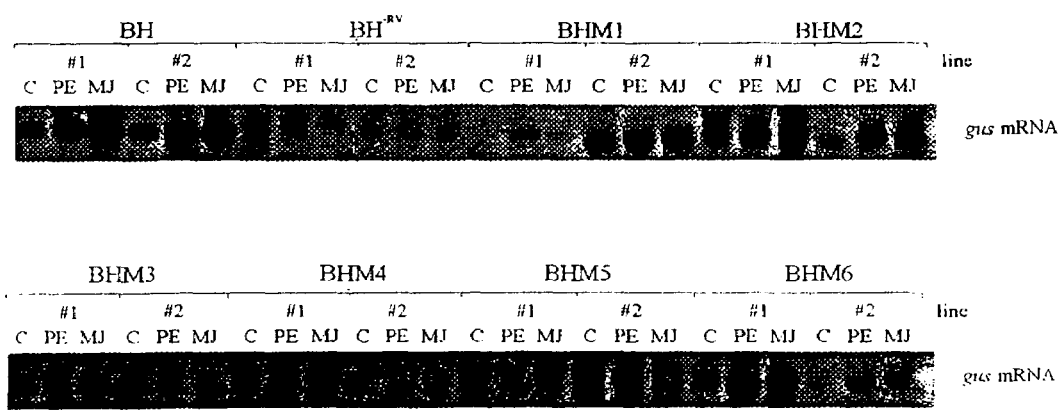
Figure 5A:
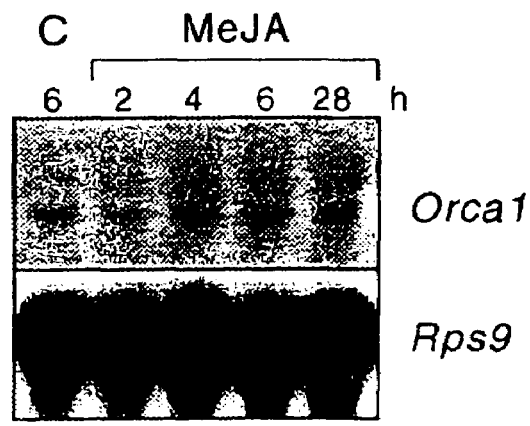

The invention will now be further illustrated by the following non-limiting examples and the drawings wherein:

FIG. 1 shows that the RV region of the Str1 BH promoter is required for elicitor and jasmonate responsiveness. Two transformed cell lines for each construct were subjected to a control treatment (C), or induced with purified elicitor (PE) or methyl-jasmonate (MJ). Constructs were introduced in *C. roseus* cell lines MP183L and BIX via particle bombardment and *Agrobacterium*, respectively;

FIG. 2 illustrates that the RV region of the Str1 promoter is an autonomous elicitor and jasmonate responsive element. Two transformed cell lines for each construct were given a control treatment (C) or induced with purified elicitor (PE), or methyl-jasmonate (MJ). Constructs were introduced in *C. roseus* cell line MP183L via particle bombardment;

FIG. 3 shows that mutations M2, 3, 4, and 5 in the RV region abolish elicitor and jasmonate responsiveness of the Str1 BH promoter. Two transformed cell lines for each construct were given a control treatment (C) or induced with methyl-jasmonate (MJ). Constructs were introduced in *C. roseus* cell line BIX via *Agrobacterium*;

FIG. 4 shows that mutations M3, 4, and 5 in the RV region abolish elicitor and jasmonate responsiveness of the Str1 BH promoter and that mutant M2 weakens the responsiveness. Two transformed cell lines for each construct were subjected to a control treatment (C) or induced with purified elicitor (PE) or methyl-jasmonate (MJ). Constructs were introduced in *C. roseus* cell line MP183L via particle bombardment;

FIG. 5 shows that Orca-2 mRNA, but not Orca-1 mRNA, is rapidly induced by MeJA and elicitor. *C. roseus* cells were exposed to MeJA (10 μM) or partially purified elicitor (PE) for the number of hours (h) indicated at the top of the figure. (A) Orca1 and Rps9 mRNA levels after addition of MeJA. (B) Orca2, Str and Rps9 mRNA levels after addition of MeJA. (C) Orca2, Str and Rps9 mRNA levels after addition of PE. Northern blots were hybridized with Orca1, Orca2, Str and Rps9 cDNAs as indicated. C, control incubation with DMSO.

Figure 6:
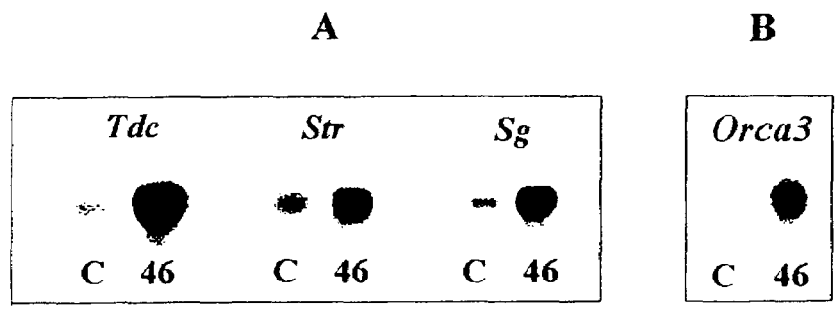
Figure 7:
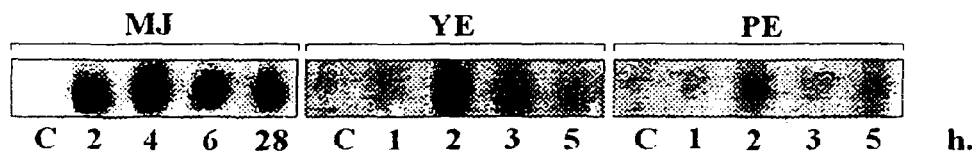
Figure 8:
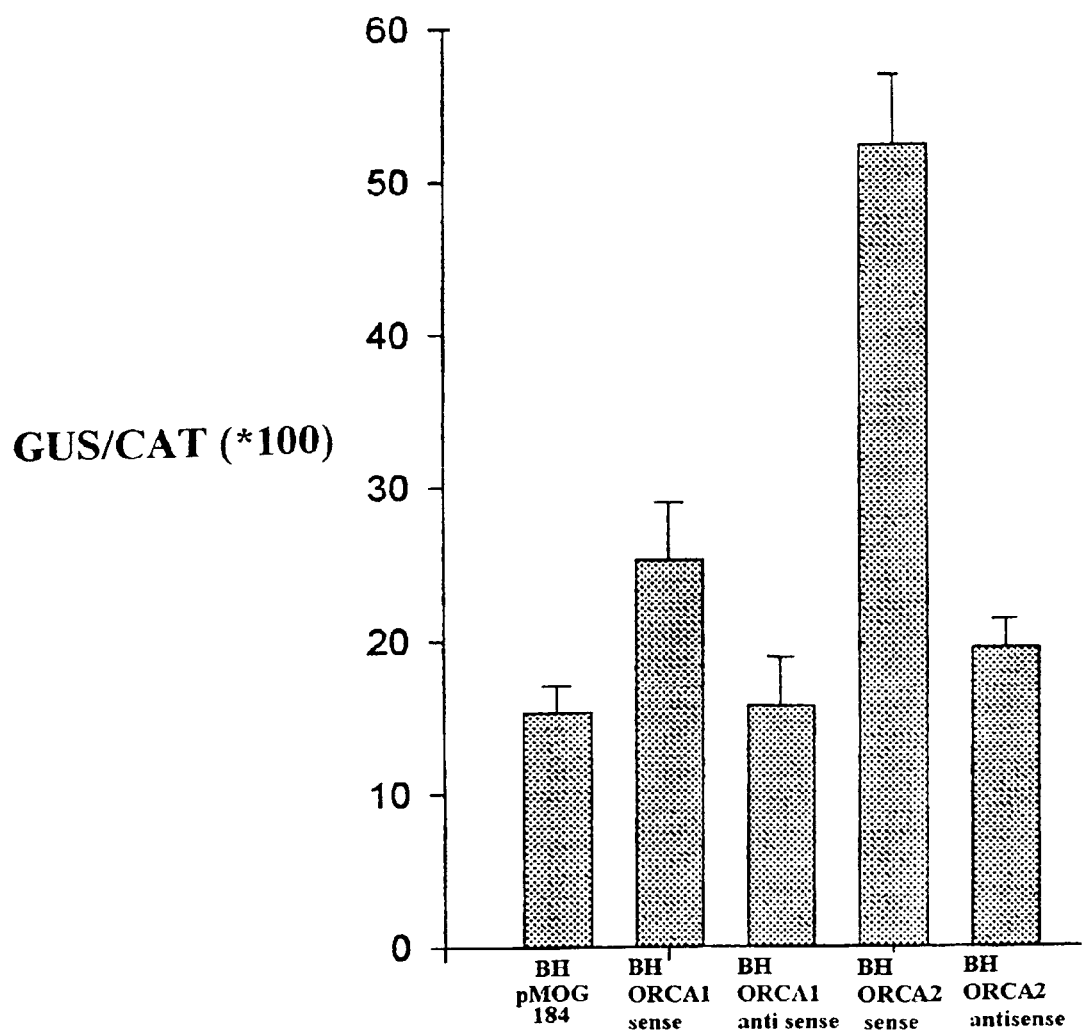
Figure 9:
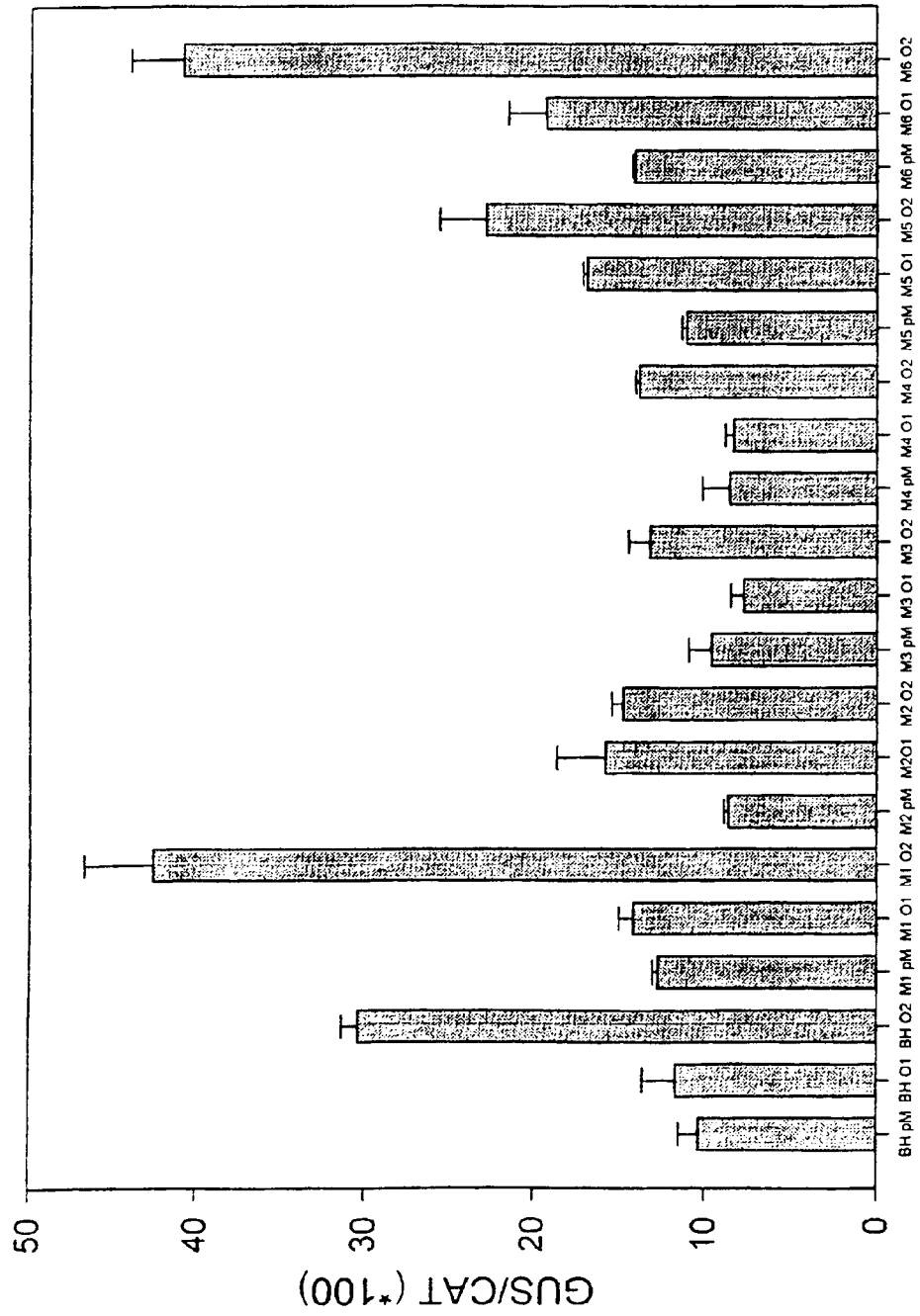
Figure 10:
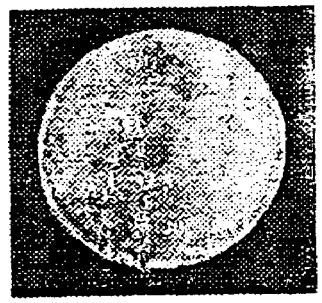
Figure 10:
Figure 11:
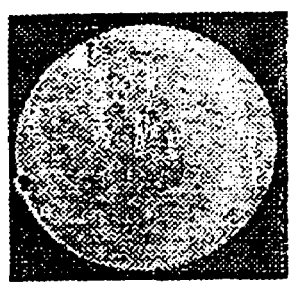
Figure 11:
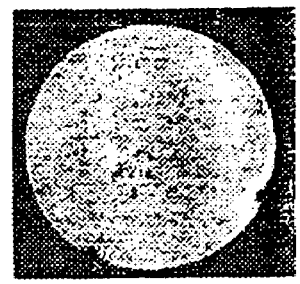
Figure 12:
Figure 12:
Figure 12:
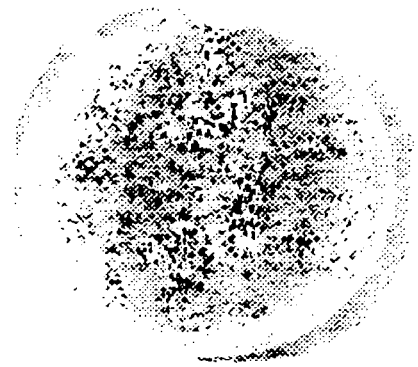
Figure 12:
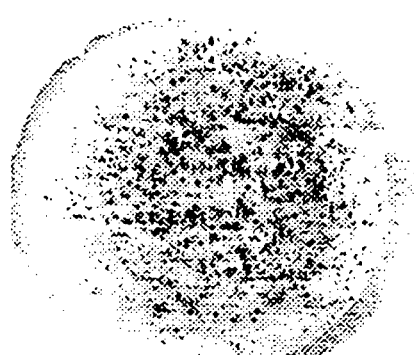

FIG. 6 illustrates that T-DNA activation tagging of the Orca-3 gene activates expression of the TIA biosynthetic genes tryptophan decarboxylase (TDC), strictosidine synthase (STR) and strictosidine glucosidase (SG). Northern blot analysis of RNA extracted from line 46 and a 4-mT-resistant control cell line (C). Blots were probed with Tdc, Str1 and Sg (6A). RNAs in FIG. 6B were hybridised with the rescued flanking plant DNA from line 46, containing the complete Orca-3 open reading frame;

FIG. 7 shows Orca3 expression patterns in elicited *C. roseus* suspension cultures. *C. roseus* cells were treated with 50 μM methyl-jasmonate (MJ), 0.5% crude yeast extract elicitor (YE) or with an equivalent amount of partially purified elicitor (PE). Cells were harvested after the time points indicated in the figure. RNA was extracted and Northern blots were probed with the rescued flanking plant DNA from line 46, containing the complete Orca-3 open reading frame;

FIG. 8 illustrates that ORCA-1 and 2 are transcriptional activators of the Str1-promoter in *C. roseus* cells. GUS/CAT ratios with standard deviation were calculated from duplicate enzyme activity measurements of three bombarded samples arising from one batch of coated particles in a representative bombardment experiment. Tungsten particles were coated with a mixture of plasmids containing BH-GUS, empty pMOG184, or pMOG184 carrying Orca-1 or Orca-2 in sense or anti-sense orientation with respect to the CaMV 35S promoter. To correct for transformation efficiency, a plasmid carrying CaMV35S-CAT was added to all coatings;

FIG. 9 illustrates that ORCA-1 and 2 transcriptionally activate the Str1-promoter in *C. roseus* cells in a sequence-specific manner. GUS/CAT ratios with standard deviation were calculated from duplicate enzyme activity measurements of three bombarded samples arising from one batch of coated particles in a representative bombardment experiment. Tungsten particles were coated with a mixture of GUS plasmids and pMOG184 derivatives. The GUS gene was driven by the Sir BH promoter or BH mutant derivatives M1 through M6. pMOG184 plasmids were either empty (pM), or carried Orca-1 (O1) or Orca-2 (O2) in sense orientation with respect to the CaMV 35S promoter. To correct for transformation efficiency, a plasmid carrying CaMV35S-CAT was added to all coatings;

FIG. 10 shows that ORCA-3 activates expression of the Str1NH promoter (–202 to –1 with respect to ATG start codon). *C. roseus* cells were bombarded with tungsten particles coated with a mixture of plasmids containing Str1 NH-GUS, empty pMOG184, or pMOG184 carrying Orca-3 in sense orientation with respect to the CaMV 35S promoter, and stained for GUS enzyme activity by addition of the substrate X-Gluc;

FIG. 11 shows that ORCA-3 activates expression of the Tdc –219 promoter (–219 to +86 with respect to ATG start codon). *C. roseus* cells were bombarded with tungsten particles coated with a mixture of plasmids containing Tdc –219-GUS, empty pMOG184, or pMOG184 carrying ORCA-3 in sense orientation with respect to the CaMV 35S promoter, and stained for GUS enzyme activity by addition of the substrate X-Gluc; and FIG. 12 shows that ORCA-1, -2 and -3 activate expression of the jasmonate-responsive RV element from the Str I-promoter. *C. roseus* cells were bombarded with tungsten particles coated with a mixture of plasmids containing 4RV-GUS, empty pMOG184, or pMOG184 carrying Orca-1, -2 or -3 in sense orientation with respect to the CaMV 35S promoter, and stained for GUS enzyme activity by addition of the substrate X-Gluc.

FIG. 13 shows that ORCA3 contains different domains affecting the transcriptional activation potential. (A) Schematic representation of ORCA3 and the different deletion derivatives. Numbers indicate amino acid positions. The AP2-domain is indicated as a black box, the acidic domain as a hatched box, and the serine-rich region as a dotted box. VP16 indicates the heterologous Herpes simplex VP16 activation domain. NLS shows the position of a putative bipartite nuclear localization signal. (B) Trans-activation potential of the ORCA3 deletion derivatives shown in (A). *C. roseus* cells were co-bombarded with the gusA reporter gene fused to the Str promoter, the reference reporter gene cat fused to the CaMV 35S promoter, and an overexpression plasmid carrying the ORCA3 deletions as indicated fused to the CaMV 35S promoter. GUS/CAT ratios are expressed as percentage of empty vector controls. Bars represent Mean ±SE (n=8 for empty vector, ORCA3 and Δ5ORCA3; n=6 for Δ3ORCA3 and Δ3Δ5ORCA3; n=3 for VP16-Δ5ORCA3). Different letters above the bars indicate statistically significant differences (P<0.05).

Figures 14A, 14B, 14C:
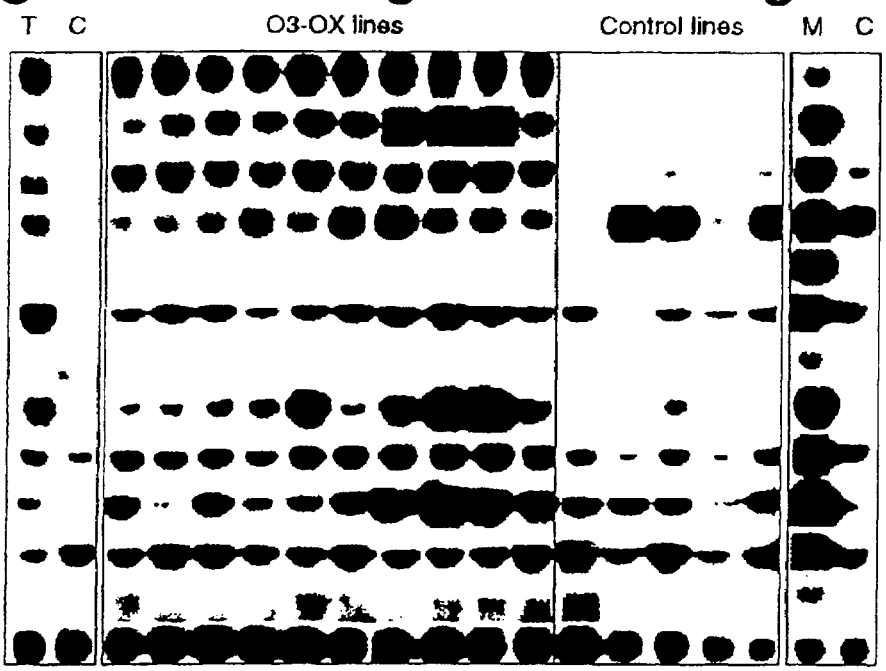
Figure 14D:
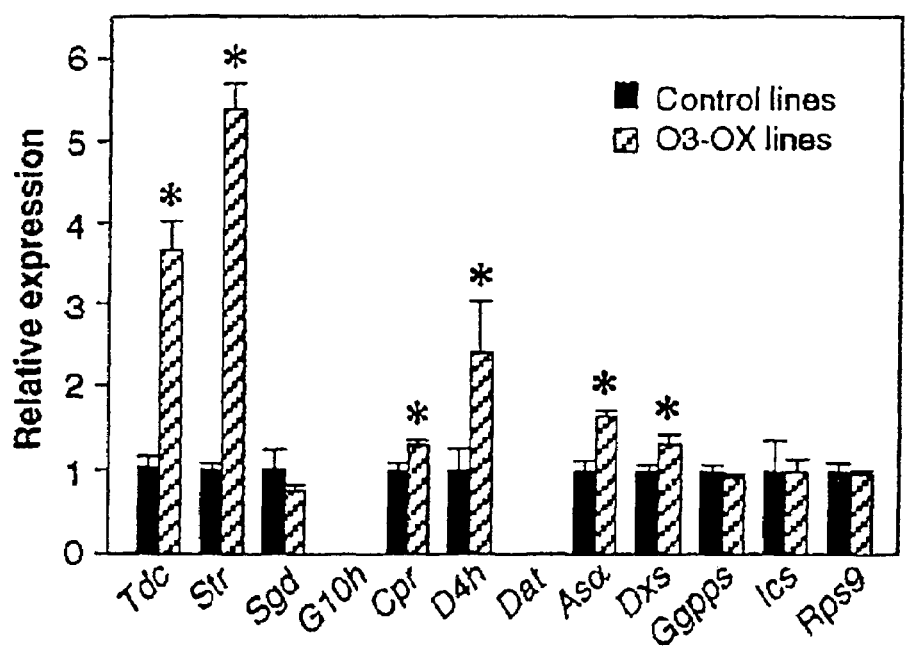

FIG. 14 shows that ORCA3 overexpression increases the expression of primary and secondary metabolite biosynthetic genes. Northern blot analysis was performed on RNA extracted from (A) tagged cell line 46 (T) and a representative control line 38 (C) in *C. roseus* genetic background BIX, (B) 10 O3-OX lines and 5 control cell lines in genetic background MP183L, and (C) from untransformed MP183L cells exposed for 6 h to 50 μM methyl jasmonate (M) or DMSO (C). (D) RNA expression levels were quantified and averaged. Mean expression of the control lines is set at 1. Bars indicate Mean ±SE. Asterisks above the bars indicate statistically significant differences, as judged from the non-parametrical Wilcoxon-Mann-Whitney test (P<0.05).

Figure 15:
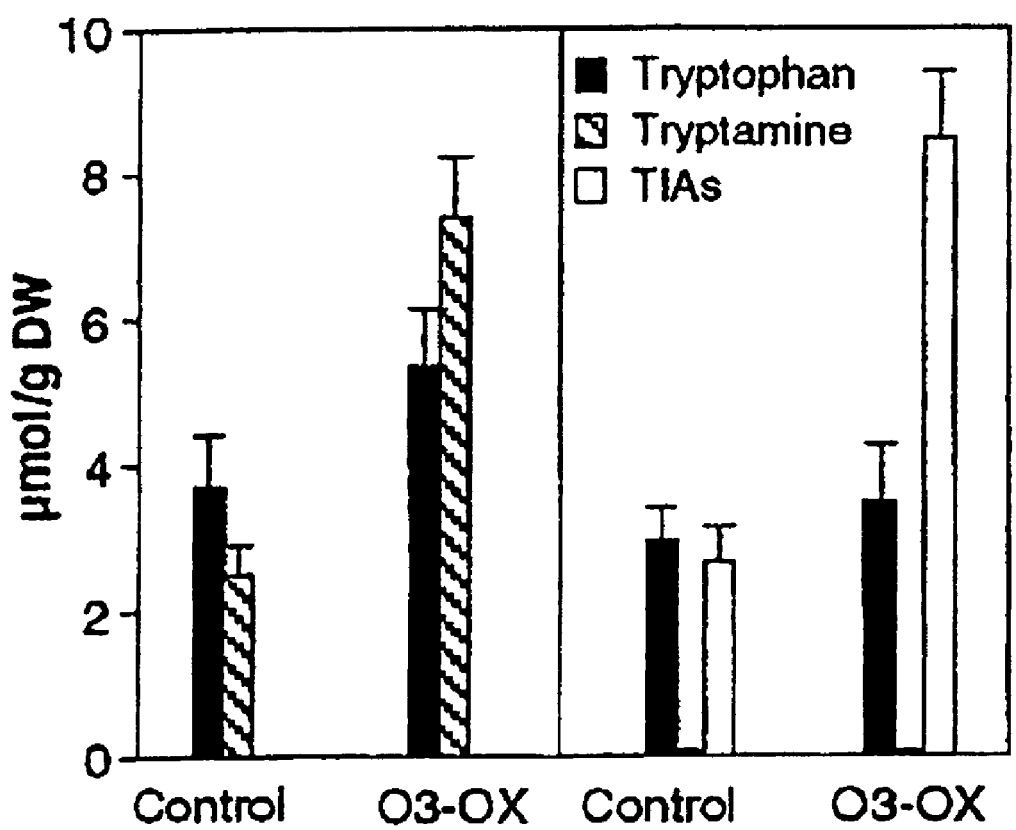

FIG. 15 shows that ORCA3 overexpression increases accumulation of tryptophan, tryptamine, and TIAs. Eight days after subculture, tryptophan, tryptamine and TIAs were extracted from 5 O3-OX and 5 control lines, without loganin supply (left panel), or 24 hours after addition of 1 mM loganin to the culture medium (right panel).

Figure 16A:
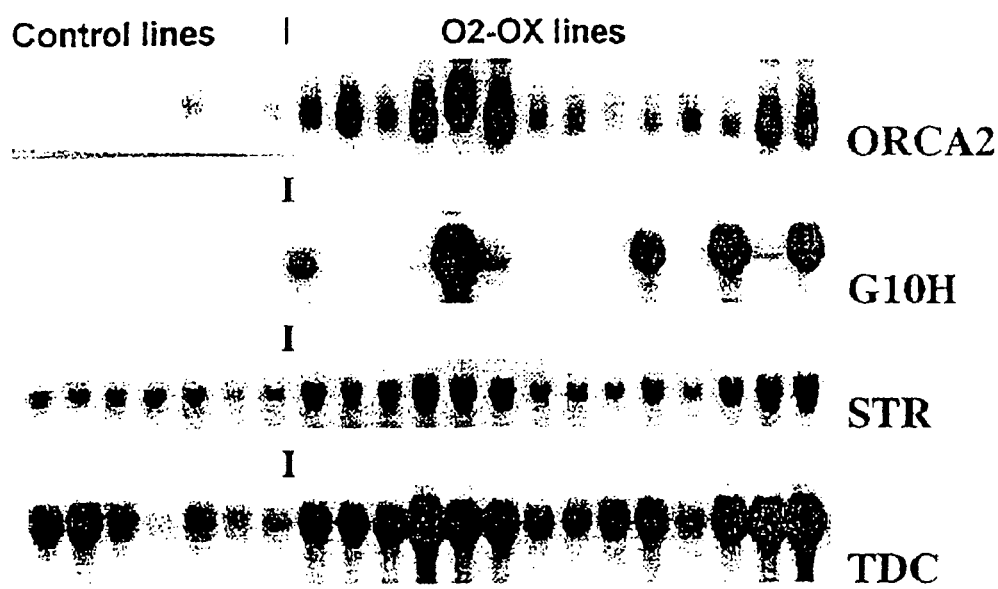
Figure 16B:
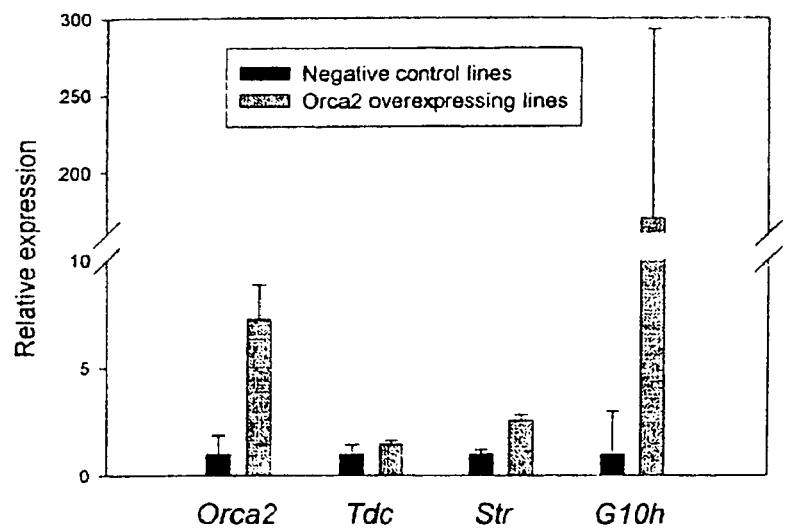

FIG. 16 shows that ORCA2 overexpression induces the expression of TIA biosynthetic genes. Upper panel: Northern blot analysis was performed on RNA extracted from 14 O2-OX lines and 7 control cell lines. Lower panel: RNA expression levels of 6 strong Orca2 expressors and 5 control cell lines were quantified and averaged. Bars indicate Mean ±SE. Mean expression of the control lines is set at 1.

Figure 17:
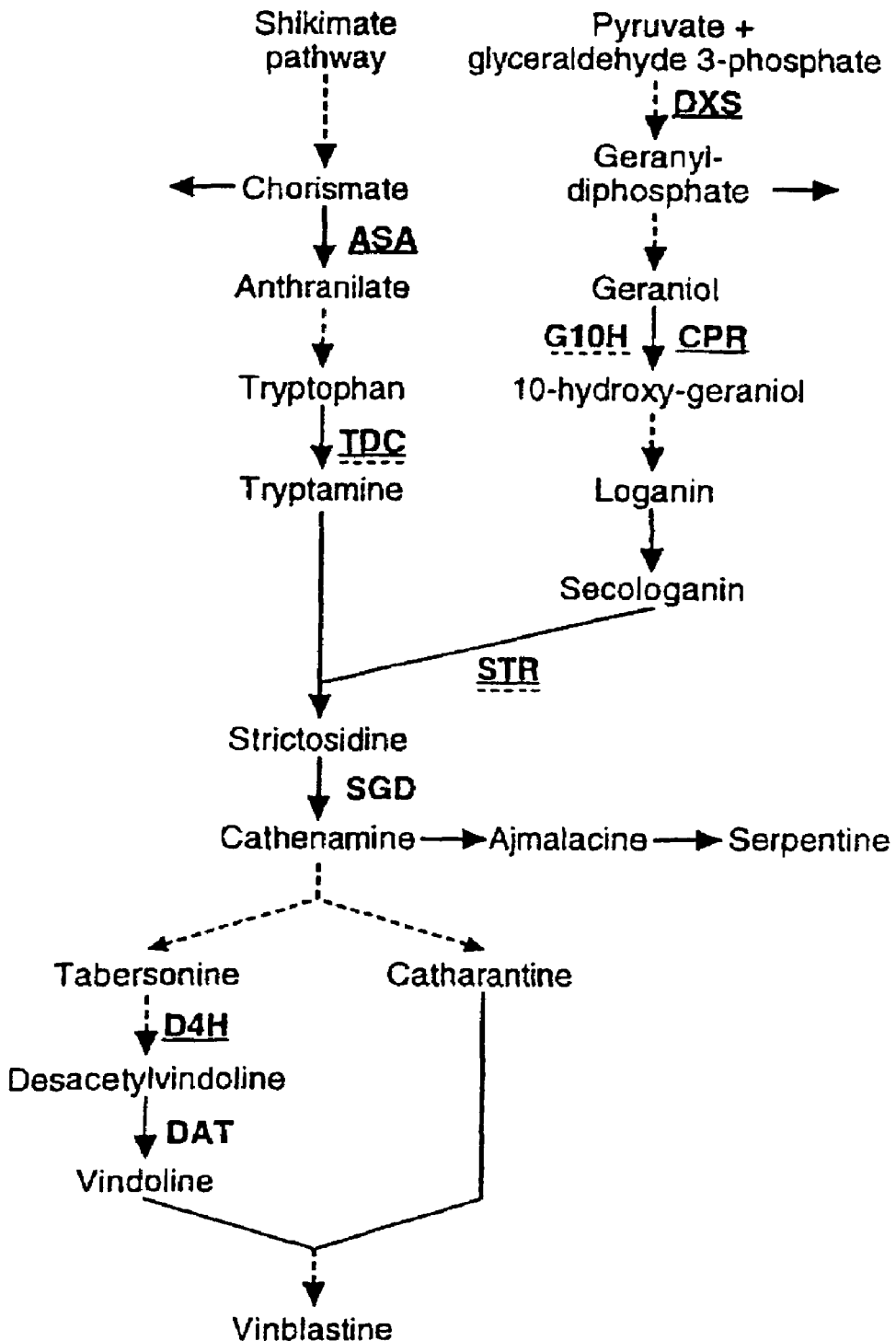

FIG. 17 schematically shows the biosynthesis of TIAs in *C. roseus*. Solid arrows indicate single enzymatic conversions, whereas dashed arrows indicate multiple enzymatic conversions. Genes regulated by ORCA3 or ORCA2 are underlined with solid or dotted lines, respectively.

The abbreviations used to indicate the TIA biosynthetic enzymes are as follows: enzymes indicated in the Figure are as follows: Anthranilate synthase (ASA); D-1 deoxyxylulose 5-phosphate synthase (DXS); Geraniol 10-hydroxylase (G10H); NADPH:cytochrome P450 reductase (CPR); Tryptophan decarboxylase (TDC); Strictosidine synthase (STR); Strictosidine β-D-glucosidase (SGD); Desacetoxyvindoline 4-hydroxylase (D4H); Acetyl-CoA:deacetylvindoline 4-O-acetyltransferase (DAT).

EXPERIMENTAL PART

Terpenoid indole alkaloids (TIAs) form a large group of natural products with ~3000 known compounds, many of which are pharmacologically active, including well known drugs such as ajmalicine, vinblastine, vincristine, ajmaline, reserpine, rescinnamine, camptothecine, ellipticine, quinine, and quinidine. The leaves of Madagascar periwinkle or *Catharanthus roseus* synthesize the very costly anti-tumor drugs vinblastine and vincristine, while the roots synthesize ajmalicine, an alkaloid that improves cerebral blood circulation. In the past years, extensive studies of secondary metabolism in this plant species and cell cultures thereof have been carried out. The TIA pathway has been mapped, although several important steps are not yet elucidated.

The central intermediate in TIA biosynthesis is the glucoalkaloid strictosidine. This compound is formed from the intermediates tryptamine and secologanin, a reaction catalyzed by the enzyme strictosidine synthase (STR; FIG. 17). Tryptophan decarboxylase (TDC) catalyzes the formation of tryptamine. Tryptophan is derived from chorismate via multiple steps, the first of which is catalyzed by anthranilate synthase (ASA). Secologanin is formed via multiple steps from geraniol. Geraniol is first 10-hydroxylated by a cytochrome P450 enzyme (geraniol 10-hydroxylase, G10H), which depends on NADPH-cytochrome P450 reductase (CPR) for its activity. Geraniol has recently been shown to arise from the non-mevalonate terpenoid pathway (MEP pathway), of which the first step is catalyzed by D-1 deoxyxylulose 5-phosphate synthase (DXS).

After strictosidine, the first step is hydrolysis of the glucoside (strictosidine β-D-glucosidase, SGD), resulting in a reactive dialdehyde. The pathway then diverges to the various types of alkaloids. No enzymes have yet been found that catalyze the formation of the different alkaloid skeletons. Several enzymes further down the pathway leading to the dimeric alkaloids (vinblastine and vincristine) have been characterized (D4H and DAT; FIG. 17). From the TIA and precursor pathways in C roseus, the genes encoding DXS (accession number AJ011840), ASA (accession number AJ250008), G10H (accession number AJ251269), CPR (accession number X69791), TDC (accession number X67662), STR (accession number X61932), and SGD (accession number AF112888), have been cloned. D4h (accession number U71604) and Dat (accession number AF053307) genes acting further downstream in the pathway have also been cloned.

For Tdc and Str the genomic sequences including elicitor-responsive promoter regions have been cloned. All cloned structural genes active in the TIA biosynthetic pathway are coordinately induced by jasmonic acid (FIG. 14C). Based on the coordinate regulation, it was hypothesized that common regulatory proteins control the expression. Recently, two jasmonate-responsive transcription factors (called ORCA2 and ORCA3; for Octadecanoid-Responsive *Catharanthus* AP2) that regulate several structural genes were cloned. Both proteins belong to the AP2-domain class of transcription factors, which is exclusively found in plants. The AP2-domain is responsible for DNA binding. The expression of the Orca2 and 3 genes is rapidly induced by jasmonate with faster kinetics than the structural genes Tdc and Str. Both ORCA2 and 3 proteins bind to the Tdc and Str promoters, and can activate the promoters in *C. roseus* cells in a transient assay. Elimination of their binding site from the Str promoter abolished jasmonate responsiveness.

The (preliminary) data, illustrated by the examples below, indicate that ORCA2 and 3 are master regulators of TIA biosynthetic gene expression, and control different subsets of TIA structural genes. In addition, ORCA3 regulates genes acting early in TIA metabolism, as well as a gene acting later in the pathway. Furthermore, ORCA3 also regulates genes in primary metabolism leading to TIA precursors. The data strongly suggest that together, ORCA2 and 3 may regulate additional and perhaps all genes in the pathway.

The biosynthesis of many classes of secondary metabolites is stimulated by jasmonates and several of its precursors. For a few pathways, for which enzymes and genes are known, this biosynthetic stimulation was shown to be preceded by induction of genes and corresponding enzyme activities that are active in these biosynthetic pathways. A non-exhaustive list of metabolite classes induced by jasmonates includes: taxoids, pheynlpropanoids, flavonoids, anthocyanins, guaianolides, anthraquinones, sesquiterpenoids, various types of alkaloids (benzophenanthridine alkaloids, terpenoid indole alkaloids).

Genes induced by jasmonates include those encoding tyrosine/DOPA decarboxylase, berberine bridge enzyme, allene oxide synthase, 4-coumarate-coA ligase, phenylalanine-ammonia lyase, chalcone synthase, bergaptol methyltransferase, lypoxygenase.

In addition, many genes in primary metabolite biosynthetic pathways were shown to be induced by jasmonates, and include those encoding anthranilate synthase, isochorismate synthase, deoxyxylulose-phosphate synthase, cytochrome P450 reductase, hydroxy-methylglutaryl-coenzymeA reductase. In all these cases, ORCA-like AP2-domain proteins may be strongly suspected to mediate these jasmonate responses, and manipulation of the expression levels of such ORCA-like proteins may modulate the levels of these various metabolites.

The techniques applied in the below examples are all standard recombinant DNA and molecular cloning techniques well known in the art and are e.g. described by Sambrook et al. (1989) Molecular cloning: A laboratory manual, second edition, Cold Spring Harbor Laboratory Press and Ausubel et al. (1987) Current protocols in molecular biology, Greene Publishing Associates and Wiley Interscience, New York.

EXAMPLE 1

1.1 Identification of an Elicitor- and Jasmonate-Responsive Element in the Str1 Promoter The RV region of the promoter of the str1 gene (DDBJ/EMBL/GenBank database accession number Y11082) of *Catharanthus roseus* (Madagascar periwinkle) coding for strictosidine synthase was, as described below, via promoter analysis including detailed scanning mutagenesis, identified as an elicitor- and jasmonate-responsive element.

The BglII/HincII fragment (BH) of the Str1 promoter and a BH fragment in which the RsaI/AvaII fragment (RV) was deleted (BH$^{-RV}$) were introduced as BglII/SalI fragments into the GusSH vector consisting of pBluescript SK+ carrying the β-glucuronidase reporter gene. These Str1 promoter derivatives fused to the gusA gene were introduced into two different *C. roseus* cell lines. Cell line MP183L was transformed via particle bombardment, whereas cell line BIX was transformed via an improved *Agrobacterium* strain (see example 4.1). For *Agrobacterium*-mediated transformation, the GusSH derivatives were introduced into the binary vector pMOG22lambdaCAT, a derivative of pMOGlambdaCAT containing the hygromycin resistance gene instead of the kanamycin resistance gene as a plant selectable marker. Northern blot analysis was performed for two independently transformed cell lines for each construct, each estimated to consist of a population of at least 100 to 1000 independent transformants. The BH fragment of the Str1 promoter conferred low basal level expression onto the gusA gene in the control (0.05% dimethylsulfoxide (DMSO)) treated cells (FIG. 1). Incubation of MP183L cells transformed with BHGusSH with partially purified yeast extract elicitor (PE; Menke et al., Plant Physiology, April 1999, Vol. 119, pp. 1289-1296) and methyl-jasmonate (MJ) for 6 h induced the expression of the gusA gene several fold (FIG. 1 upper panel). These conditions similarly induced the endogenous Str1 gene as described previously (Menke et al., 1999). The BH-RV fragment did not confer elicitor- and MJ-responsive gene expression onto the gusA reporter gene in cell line MP183L (FIG. 1 upper panel). Similar results were obtained with BIX cell lines transformed with these Str1-promoter derivatives fused to gusA. BIX cells carrying the BH-gusA fusion had low basal gusA mRNA levels, but incubation for 6 h with MJ induced high gusA gene expression (FIG. 1 lower panel). BIX cells carrying BH-RV fused to gusA did not have detectable basal expression levels and could not be induced by MJ (FIG. 1 lower panel). This loss of function experiment shows that the RV region of the Str1 promoter is required for elicitor- and jasmonate-responsive gene expression.

In a gain of function experiment it was tested whether the RV fragment of the Str1 promoter was able to confer elicitor- and JA-responsive gene expression onto a minimal promoter-gusA fusion. To this end tetramers of the RV region were constructed and fused to a Cauliflower Mosaic Virus 35S promoter truncated to −47 and fused to gusA in the vector GusSH-47. The RV region was cloned as a RsaI/AvaII fragment into the SmaI/EcoRV sites of pIC20H, and tetramerized using the enzymes BamHI/BglII. The tetramer was cloned as a BamHI/BglII fragment into the BamHI site of GusSH-47. *C. roseus* cell line MP183L was transformed with this construct via particle bombardment. Control cell lines were generated by introducing GusSH-47 or 6Tcyt-GusSH-47 in two independently transformed cell lines for each construct. The 6Tcyt construct contains 6 head-to-tail copies of the cyt-1 cis-acting element from the T-DNA T-CYT gene which is not elicitor- or jasmonate-responsive. Northern blot analysis was performed for two independently transformed cell lines, each estimated to consist of a population of at least 100 to 1000 independent transformants. Incubation of the 4RV-47 cell lines with PE or MJ for 6 h resulted in induction of gusA gene expression as compared to the expression of the control (0.05% DMSO) incubated cells (FIG. 2). The same treatment of cell lines carrying the −47 construct did not result in measurable gusA mRNA levels in the control or induced samples (FIG. 2). In the cell lines carrying the 6Tcyt-GusSH-47 construct, high basal levels of gusA mRNA were found (FIG. 2). Treatment of these cell lines with PE or MJ for 6 h did not induce expression (FIG. 2). These results show that the RV region is sufficient to confer elicitor- and jasmonate-responsive gene expression onto an otherwise inactive minimal promoter-gusA construct. The results with the 6Tcyt lines show that the RV region does not potentiate a silent elicitor-responsive element within the CaMV −47 region or elsewhere on the construct.

Detailed block scanning mutagenesis of the RV region in the context of the BH fragment of the Str1 promoter was performed to pinpoint the exact location of the elicitor- and jasmonate-responsive-sequence within the RV fragment. Mutations were introduced by PCR with primers having a 6 bp mismatch combined with M13-reverse primer using the XhoI/HincII fragment of the Str1 promoter cloned in pIC20H as a template. The primers RVM1-RVM8 are disclosed in the below Table 1.1 (SEQ ID NOs 8-15)

TABLE 1.1

Primers used in detailed block scanning mutagenesis of the RV region

| | |
|---|---|
| RVM1 | 5'-CCACGTGGTTGTAGTCTCTTAGACC-3' |
| RVM2 | 5'-GGTACATCAGAGAATGACCGCCTTC-3' |
| RVM3 | 5'-CACTCTTACTGGCGCTTCTTTGAAAG-3' |
| RVM4 | 5'-AGACCGCGAAGAATGAAAGTG-3' |
| RVM5 | 5'-AGACCGCCTTCTTACTTTCTGATTTCCCC-3' |
| RVM6 | 5'-TTGAAAGACTAAACCCTTGGAC-3' |
| RVM7 | 5'-GAAAGTGATTTGGGAACGACCTTG-3' |
| RVM8 | 5'-CCCTTGCTGGAAGTTTGGTGAG-3' |

PCR fragments obtained were used as primers in PCR reactions together with M13-forward primer on the XhoI/HincII fragment of the Str1 promoter cloned in pIC20H. PCR fragments obtained were reamplified using M 13-reverse and M113-forward primers. Amplified PCR products were digested with BglII/SalI and cloned into GusSH digested with BamHI/SalI. In total 8 mutated versions of the RV fragment were made, covering the entire fragment from the RsaI site to the AvaII site. In each mutant 6 adjacent nucleotides (nt) were changed into their complementary nt, i.e. changing A to T and G to C. The 8 mutated versions of the BH fragment fused to gusA were introduced into C. roseus cell lines MP183L and BIX as described above. Northern blot analysis was performed for two independently transformed cell lines for each mutant construct, that were incubated for 6 h with DMSO or MJ for C. roseus BIX cell lines (FIG. 3) and with DMSO, PE or MJ for C. roseus MP183L cell lines (FIG. 4). By comparing basal and MJ-induced gusA gene expression for all the mutant BIX lines to the expression conferred by wildtype BH fragment it is clear that mutations 1, 6, 7 and 8 conferred a wildtype gene expression pattern (FIG. 3). In mutant 2 the expression was only minimally inducible. In mutants 3, 4 and 5 expression was uninducible, and similar to the expression conferred by the BH-RV fragment (FIG. 3). The experiment with the MP183L lines carrying the mutated BH fragment gave similar results (FIG. 4). Mutants 1, 2 and 6 showed expression patterns similar to the wildtype BH fragment. Mutants 3, 4 and 5 are not consistently inducible by PE or MJ and gave similar expression patterns to the BH-RV fragment.

In another experimental series, the effect of the block mutations was studied in constructs consisting of tetramers of RV derivatives fused to GusSH-47. Tetramers of RV mutants M2, M3, M4, M5 and M6 were constructed as described above for RV wildtype fragment, and fused to a Cauliflower Mosaic Virus 35S promoter truncated to −47 fused to gusA in the vector GusSH-47. The constructs were introduced in C. roseus cell line MP183L via particle bombardment. Two independent transformed cell lines were generated for each construct. Incubation of the cell lines carrying RV wildtype or mutant M6 tetramer constructs with PE or MJ for 6 hours resulted in induction of gusA gene expression as compared to the expression of the control (0.05% DMSO) incubated cells (results not shown). The same treatment of cell lines carrying the mutant M2, M3, M4 or M5 tetramer constructs did not result in measurable gusA mRNA levels in the control or induced samples (results not shown).

These results show that the elicitor- and MJ-responsive element is contained within the 24 bp sequence that is covered by mutations 2 to 5, with mutations 3, 4 and 5 having the most dramatic negative effect on the inducibility of the BH or the RV fragment of the Str1 promoter.

EXAMPLE 2

Cloning of ORCA-1 and 2

The RV region was, as described in Example 1, identified as an elicitor- and jasmonate-responsive element in the Str1 promoter. Use of the RV element as bait in a one-hybrid transcription factor screening resulted in the isolation of 17 cDNA clones that corresponded to two different mRNA species, encoding proteins belonging to the APETALA2 domain class of transcription factors. They were named ORCA-1 and 2 (for Octadecanoid-Responsive Catharanthus AP2).

The RV region of the Str1 promoter (DDBJ/EMBL/GenBank database accession number Y10182) was cloned as a RsaI/AvaII fragment into the SmaI/EcoRV sites of pIC20H and tetramerized using the enzymes BamHI/BglII. The tetramer was cloned as a BamHI/BglII fragment into the BamHI site of pHIS3NX. The tetramer-HIS3 gene fusion was transferred as a NotI/XbaI fragment to the yeast integration plasmid pINT1.

The resulting plasmid was linearized with NcoI and introduced into yeast strain Y187. Recombinants were selected on YPD medium containing 150 μg/ml G418, and the occurrence of a single recombination event between the pINT1 derivative and the chromosomal PDC6 locus was verified via Southern blotting. Yeast strain Y187-4RV was then used in a one-hybrid screen for DNA-binding proteins with a cDNA library of Catharanthus roseus cloned in the plasmid pACTII. To construct the library, cDNA was synthesised with a Stratagene kit on 2 different poly(A) RNA preparations mixed in a 1:1 ratio isolated from cell suspensions that were elicited with 0.05% yeast extract for 1 and 4 h, respectively. The cDNA was cloned in the EcoRI/XhoI sites of lambdaACTII. The amplified lambda library, consisting of $3.5 \times 10^6$ independent primary transformants was converted to a pACTII plasmid library via Cre-lox-mediated in vivo excision in Cre-expressing in E. coli strain BNN132. Four million Y187-4RV transformants were screened in a one-hybrid screening. Plasmids isolated from 364 colonies obtained on SD medium without histidine and leucine were retransformed to Y187-4RV, and two Y187 derivatives carrying tetramers of RV mutant fragments RVM4 and RVM5 fused to the HIS3 gene. Seventeen plasmids showed strongly reduced growth in Y187-4RVM4 compared to Y187-4RV and Y187-4RVM5, whereas all other plasmids did not give rise to significant differences in growth between the three yeast strains. Partial sequencing of these plasmids revealed that they belonged to one of only two classes. The ORCA-1 class consisted of 3 plasmids carrying cDNA sequences with identity to the sequences in SEQ ID NO 1. SEQ ID No:1 is derived from plasmid RV124. Both sequences are identical throughout the main open reading frame, but diverge at their 3' ends. Obviously, they are derived from the same gene, and the differences could have arisen by alternative splicing of the primary transcript. They contain the complete coding region, since SEQ ID No. 1 contains an in frame stop codon preceding the first start codon. The ORCA-2 class consists of 14 plasmids carrying cDNA sequences with identity to the sequence in SEQ ID No:2. All ORCA-2 cDNA sequences appeared to be partial. The missing portion was isolated via PCR with the primers 4TH (5'-CCCCACCAAACCCAAAAAAAG-3'; SEQ ID NO:16) and RV117 (5'-CCATATCCTCGATC-CTTTTCTC-3'; SEQ ID NO:17) using the pACTII cDNA library as a template. A prominent 0.6 kbp PCR band was digested with EcoRI and BamHI, and cloned in pBluescript II SK+. A complete clone was constructed in pBluescript II SK+ by fusion of the PCR fragment with the cDNA fragment from plasmid RV210 using the unique BamHI site.

EXAMPLE 3

Expression of ORCA-1 and -2

Figure 5B:
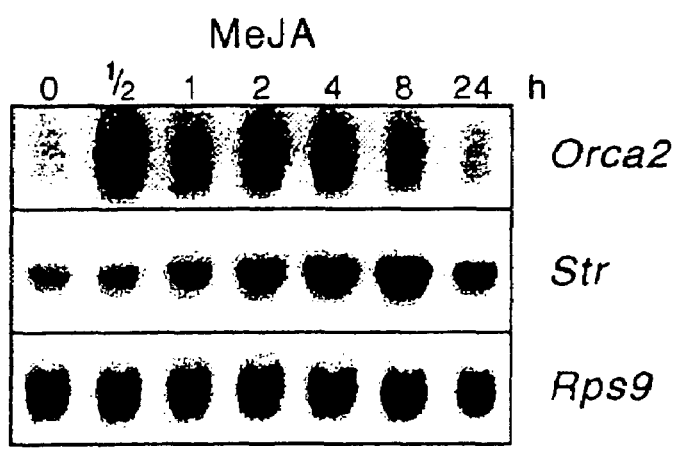
Figure 5C:
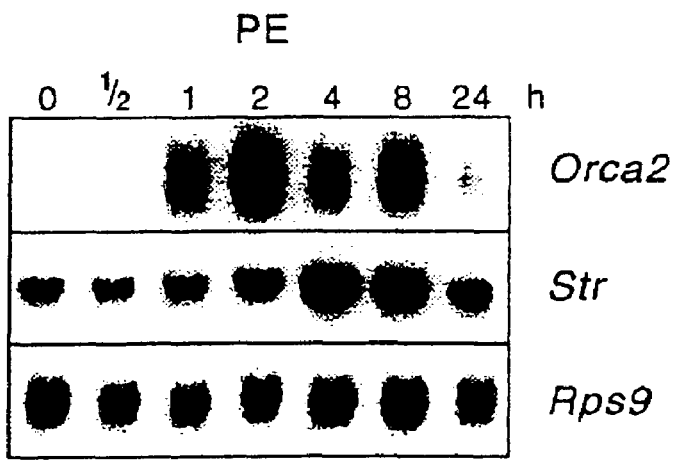

To analyse the expression of the Orca-1 and Orca-2 genes suspension-cultured C. roseus cells were incubated with MJ (10 µM) or PE (0.05% YE equivalent). After incubation periods ranging from 1 to 24 h the cells were harvested and immediately frozen in liquid nitrogen. Total RNA was isolated and Northern blots were probed with the full-length sequence from SEQ ID NO:1, specific for Orca1, and a 450 bp EcoRI/KpnI fragment from SEQ ID NO:2, specific for Orca-2. Orca1 gene expression was not modulated by MJ (FIG. 5A), or PE (data not shown). MJ-induced gene expression was clear for Orca-2 with high levels of expression starting at 0.5 hours and remaining high to up to 8 hours after MJ addition as compared to the control (FIG. 5B). Orca-2 was also rapidly induced by PE, with an increase of mRNA levels within 1 h and a high level to up to 8 hours after PE addition (FIG. 5C). These results show that Orca-2 is inducible by MJ and PE, whereas Orca1 expression is not affected.

EXAMPLE 4

Cloning of ORCA-3

T-DNA activation tagging has been used as a reverse genetic method to isolate genes involved in plant growth and development. Genes involved in responses to ABA and cytokinin have been identified using this technique. A T-DNA carrying a strong transcriptional enhancer is integrated into the plant genome by *Agrobacterium tumefaciens*-mediated transformation. Expression of genes adjacent to the integration site will become deregulated, which can result in a dominant mutation.

To isolate dominant mutants with increased expression of TIA (terpenoid indole alkaloid) biosynthetic genes, the Tdc gene was used as selectable marker. TDC is involved in the conversion of L-tryptophan into tryptamine, one of the first steps in TIA biosynthesis. TDC is able to use substrates other than L-tryptophan, like 4-methyltryptophan (4-mT). This compound is toxic to plant cells, and is converted by TDC in to the non-toxic 4-methyltryptamine. We used 4-mT to select for C. roseus cell lines in which the activation tag causes an increase in Tdc expression. The selection for cell lines with increased Tdc expression is described below.

4.1 Plasmids and *Agrobacterium tumefaciens* Strain

Plant cell transformations were done by applying the ternary vector system (van der Fits et al., manuscript in preparation). A KpnI fragment carrying a constitutive virG mutant gene was cloned onto plasmid pBBR1MCS and this plasmid was used as ternary vector.

A brief outline of the cloning of the binary vector Tag-2B4A1 follows: The 35S promoter derivative 2B4A1, containing multiple copies of the B and A1 enhancers from the CaMV 35S promoter, was cloned on a pUC21 plasmid containing the Hpt gene driven by a deletion derivative of the FMV 34S promoter (34S-Hpt) and the gusA reporter gene. This complete plasmid (including pUC21 sequences) was digested at a unique BglII site and cloned into the binary vector pSDM14 cut with BamHI. The 35S promoter is now reading towards the right border sequence.

Both plasmids (binary and ternary vectors) were introduced into *Agrobacterium tumefaciens* strain LBA4404 via triparental mating using pRK2013 as a helper strain.

4.2 Transformation of *Catharanthus roseus* Suspension Cultured Cells

*Agrobacterium tumefaciens* strains were grown for 3 days at 28° C. on solid AB medium containing 20 µg/ml rifampicin, 100 µg/ml kanamycin and 75 µg/ml chloramphenicol. From these bacteria a liquid overnight culture was grown in the same medium. Cells were harvested by centrifugation and resuspended at a $OD_{600}$ of 1 in LS medium of pH 5.2 supplemented with 2 mg/l NAA, 0.2 mg/l kinetin, 3% sucrose, 1% glucose and 100 µM acetosyringone (hereafter called cocultivation medium).

C. roseus cells (cell line BIX) are grown in LS medium supplemented with 3% sucrose, 0.2 mg/l kinetin and 2 mg/l NAA (hereafter called LS13) at 25° C. (16/8 h light/dark cycle) and subcultured every 7 days by transferring 7.5 ml of cells in 50 ml medium. For transformation 7 days old cells were used. The culture medium was replaced by cocultivation medium and the cell density was adjusted to 50% sedimentation volume. On a petridish (diam. 80 mm) containing 25 ml of cocultivation medium solidified with 0.7% plant tissue culture agar, 7.5 ml of this C. roseus suspension was mixed with 750 µl *Agrobacterium tumefaciens* culture. Dishes were taped using leucopor tape and put at 25° C. in the dark for 3 days. After the cocultivation the cells were washed and plated on a paper filter disc (diam. 75 mm, Whatmann, No. 4). These filters were placed in petridishes containing 25 ml LS13 with 50 µg/ml hygromycin-B, 400 µg/ml cefotaxim, 100 µg/ml vancomycin and 0.4 mM 4-methyl-tryptophan. Filters were transferred onto fresh medium weekly.

4.3 Isolation of a 4-mT Resistant C. roseus Line with Increased TIA Biosynthetic Gene Expression An estimated number of 400.000 to 500.000 stable, independent C. roseus transformants were generated by *Agrobacterium tumefaciens*-mediated transformation with the tagging construct Tag-2B4A1. Transformants were placed on selective medium containing 50 µg/ml hygromycin-B, 400 µg/ml cefotaxim, 100 µg/ml vancomycin and 0.4 mM 4-mT. After several weeks of selection 281 independent 4-mT-resistant calli were obtained. These calli were transferred into liquid medium containing 50 µg/ml hygromycin-B and 0.2 mM 4-mT. From these suspension cultures RNA was extracted. Northern blot analysis showed that several mutants had an increased Tdc mRNA level (data not shown), which in all likelihood is causing the 4-mT resistance. One these mutants (line 46) is described in more detail below.

For line 46 Northern blot analysis was performed using other genes from the TIA biosynthetic pathway. RNA extraction and Northern blot analysis were performed. Ten µg RNA samples were loaded onto the gels. As 32P-labeled probes, cDNAs encoding TDC, STR and SGD were used.

Besides Tdc, also Str1 and Sg mRNA levels were increased significantly in the tagged cell line 46, when compared to a 4-mT resistant control cell line (number 38) (FIG. 6A). Thus in line 46, the T-DNA tag appears to have activated a central regulator of TIA biosynthetic gene expression, thereby inducing the expression of at least three genes, and possibly the complete TIA biosynthetic pathway. Chromosomal DNA was extracted from 50 gram fresh weight of cells from suspension line 46 and isolated by CsCl-Ethidiumbromide ultracentrifigation. Southern blots were made and the gusA gene was used as 32P-labeled probe isolated from GusSH. Southern blot analysis of line 46 showed that only one T-DNA copy was integrated into the plant genome (data not shown).

For plasmid rescue, 10 μg genomic DNA of line 46 was digested with XbaI (a unique site in tagging construct Tag-2B4A1), ligated and transformed to electrocompetent cells of *E. coli* strain NM554.

Plasmid analysis of the obtained *E. coli* transformants identified the rescued plasmid 46×8, which carried 1.6 kb of plant DNA immediately flanking the right border of the tagging construct. Using the rescued sequence as a probe on a Northern blot of RNA isolated from line 46 and control line 38, one hybridising mRNA species was observed (FIG. 6B). This transcript was absent in control cell line 38, whereas it was present at a high level in line 46.

Sequence analysis of plasmid 46×8 revealed an open reading frame (ORF), located at approximately 600 bp downstream of the start of the rescued plant sequence. Homology searches in databases revealed one AP2 domain present in the predicted amino acid sequence of this ORF.

AP2 domain containing proteins are a class of transcription factors exclusively found in plants. The encoded protein was called ORCA-3 (for octadecanoid-responsive *Catharanthus* AP2 domain). Several AP2 domain transcription factors, all containing one conserved AP2 domain, have been shown to participate in stress signalling (Pti, EREBP, CBF1, DREB). CBF1 has been demonstrated to act as central regulator of cold-induced gene expression in *Arabidopsis thaliana*. In analogy, the tagged gene described here, appears to encode a central regulator of TIA biosynthetic gene expression.

The sequence rescued on plasmid 46×8 is of genomic origin, and may be interrupted by intron sequences. To isolate a cDNA copy of the mRNA transcribed from the tagged gene, a PCR approach was followed. Primer sequences were based on DNA sequence information from the rescued plasmid. Primer OR1 (5'-GAATTCATATGGCGGAAAGCTGTCAG-GAGGATTC: SEQ ID NO:18) was combined with the vector T3 primer and OR4 (5'-CGACGTCGTAGAAGGCTCCG-CAGGG; SEQ ID NO:19) with the vector M13-40 primer in PCR reactions using lambda DNA prepared from a *C. roseus* root cDNA library as a template to isolate the 3' respectively 5' parts of the ORCA3 cDNA. Based on DNA sequence data from these partial cDNA clones, primers OR5 (5' AGATCT-CATAGTTCCGAAGAAATC-ATTTCCGTCTCAG; SEQ ID NO:20) and OR6 (5' AGACTCGTGAACTTTTTTG-GATATAAAATTTTGTAC-ATTCC; SEQ ID NO:21) were developed, which were used in a PCR on the rescued 46×8 plasmid to obtain the complete ORCA-3 open reading frame. The cDNA and amino acid sequences are provided in SEQ ID NO:3 and SEQ ID NO:6, respectively. Homology with other AP2 domain proteins, including the Catharanthus proteins ORCA-1 and ORCA-2 described above, is restricted to the AP2 domain. Sequences outside this domain are not conserved.

EXAMPLE 5

The Tagged ORCA-3 Gene is Induced by Elicitor and Methyl-Jasmonate

Previous research showed that the octadecanoid pathway, leading to the synthesis of jasmonate, is involved in elicitor-induced expression of TIA biosynthetic genes (Menke et al., 1999). Treatment of *C. roseus* cells with methyl-jasmonate (MJ) thus resulted in a transient increase of both Tdc and Str1 mRNA levels.

The T-DNA tagging experiment in Example 4.3 showed that the Tdc, Str1 and Sg genes are regulated by ORCA-3. Based on the fact that one other *Catharanthus* AP2 domain protein, ORCA2, is involved in the elicitor- and jasmonate-responsive expression of the Str1 gene (Example 2), it was speculated that ORCA-3 may be a second elicitor- and jasmonate-responsive transcription factor.

Northern blots were loaded with RNA from *C. roseus* cells treated for various time points with MJ, crude yeast extract elicitor (YE) and with a partly purified elicitor from yeast extract (PE). Subsequently, blots were probed with plasmid 46×8, containing the tagged gene. Treatment of cells with MJ resulted in a rapid increase in expression of the tagged gene (FIG. 7). This increase was already observed within 2 h after addition of MJ and sustained for at least 28 h. The induction of Tdc and Str1 expression was slower (maximal at 4 h after treatment) and was also maintained for at least 28 h (Menke et al., 1999). Because of the induction by a product from the octadecanoid pathway, the tagged gene was named Orca-3 (Octadecanoid Responsive *Catharanthus* AP2-domain protein). Incubation of cells with crude (YE) and partly purified (PE) elicitor (FIG. 7) resulted in a rapid and transient increase of Orca-3 mRNA levels, although the expression level is low relative to MJ-induced levels. The maximal induction of gene expression is at approximately 2 h after addition of the elicitor. The maximal induction of Tdc and Str1 expression by the elicitors occurs later (maximal induction after 6-8 h; Menke et al., 1999).

The Northern blot analysis shows that Orca-3 expression is elicitor- and jasmonate-responsive and precedes the induction of the TIA biosynthetic genes, indicating that ORCA-3 is an elicitor- and jasmonate-responsive transcription factor that coordinately controls TIA biosynthetic gene expression.

EXAMPLE 6

Binding Site of ORCA-1 and 2 within the RV Region of Str Promoter

To identify the ORCA binding site within the RV region, Y187 yeast derivatives that contained tetramers of the RV wildtype fragment and mutants M1 through M6 (see below and Table 1.1 for mutations) fused to the HIS3 gene were constructed via single cross-over in the PDC6 locus as described above.

The sequence of the RV region (SEQ ID NO:7) of the Str1 promoter is shown below. Mutated blocks are underlined or indicated in bold face. Nucleotides within each block were changed into their complementary nucleotides.

```
        M2          M4        M6
GTACATCACTCTTAGACCGCCTTCTTTGAAAGTGATTTCCCTTGGACC
        M1          M3        M5        M7
```

The yeast strains were then separately transformed with pACTII derivatives RV124 (encoding ORCA-1 fused to the GAL4 activation domain) and RV210 (encoding part of ORCA-2 including the AP2 domain fused to the GAL4 activation domain). Transformants were plated on SD minimal medium without leucine but containing histidine. Colonies obtained after 5 days were streaked on SD plates without histidine and leucine and growth was recorded after 5 days (Table 6.1). Growth indicates that ORCA proteins bound the RV derivative and activated HIS3 gene transcription, whereas lack of growth indicates that ORCA proteins failed to bind the RV derivative. The results indicate that ORCA-1 and 2 failed to confer growth in yeast containing mutants M3 and M4 fused to the HIS3 gene. In these mutants, blocks of 6 nucleotides are changed in their complementary nucleotides within the sequence GACCGCCTTCTT. This sequence is similar to the binding site identified for tobacco EREBP proteins (Ohme-Takagi and Shinshi, Plant Cell 7:173-182, 1995) and tomato Pti proteins (Zhou et al., EMBO J. 16, 3207-3218, 1997) within PR gene promoters and for *Arabidopsis* CBF and DREB proteins within COR gene promoters (Stockinger et al., Proc. Acad. Sci. USA, 94:1035-1040, 1997).

In addition, ORCA-2 failed to confer growth in yeast containing mutant M2 fused to the HIS3 gene.

TABLE 6.1

Growth of yeast Y187 derivatives containing different RV mutants fused to the HIS3 gene transformed with ORCA-1 or ORCA-2 expressing pACTII plasmids.

| RV derivative | ORCA-1 (RV124) | ORCA-2 (RV210) |
|---|---|---|
| RV | + | + |
| M2 | + | − |
| M3 | − | − |
| M4 | − | − |
| M5 | + | + |
| M6 | + | + |

EXAMPLE 7

ORCA-1 and 2 are Transcriptional Activators of the Str1-Promoter in *C. roseus* cells To investigate whether ORCA-1 and 2 can act as transcriptional activators interacting with the Str1-promoter, *C. roseus* cells were transiently cotransformed with a Str1-promoter-gusA fusion (BH-GusSH) construct, an overexpression vector (pMOG184) carrying Orca1 or Orca2 cDNAs fused in sense or antisense orientation to the CaMV 35S promoter and a overexpression vector carrying the chloramphenical acetyl transferase gene (cat). As a control, cotransformation of BH-GusSH with an empty overexpression vector was done. The CaMV 35S-cat construct served as an internal control for transformation efficiency. Cells were transformed through particle bombardment as described before, using the three constructs in a ratio of 1:1:3 (gus:cat:orca). Twenty four hours after transformation, cells were harvested and frozen in liquid nitrogen. GUS and CAT activity assays were performed and the Gus reporter gene expression was expressed as a GUS/CAT ratio to correct for transformation efficiency. Expression of Orca-1 in sense orientation resulted in a higher GUS activity (gus/cat ratio, 1.6 fold induction) as compared to the control (BHGusSH+pMOG184) (FIG. 8). Expression of Orca-1 in antisense orientation did not alter the GUS activity level (FIG. 8). Expression of Orca-2 in sense orientation resulted in a 3.3 fold induction of GUS activity, whereas expression of Orca-2 in antisense orientation had little or no effect on GUS activity as compared to the control transformed cells (BHGusSH+pMOG184) (FIG. 8). These results show that transient overexpression of either ORCA-1 or 2 (in sense orientation) enhances the expression of the gusA reporter gene driven by the Str-promoter fragment BH.

To show that ORCA-1 and 2 enhance the expression driven by the Str1-promoter in a sequence-specific manner, co-transformations were done using wild-type and mutant versions of the Str1-promoter (fused to gusA). ORCA-1 enhanced the expression of the gus reporter gene to some degree through interaction with wild-type and mutant versions 1, 2, 5 and 6 of the BH fragment of the Str1-promoter, as compared to the control pMOG184) (FIG. 9). ORCA-1 did not enhance the expression of reporter constructs driven by mutant versions 3 and 4 of the Str1-promoter fragment BH (FIG. 9). ORCA-2 strongly enhanced the expression of gus reporter gene through interaction with wild type and mutant version 1, and 6 of the BH fragment of the Str1-promoter (FIG. 9), as compared to the control (pMOG184). ORCA-2 enhanced gus gene expression weakly for mutants 2 and 5 (FIG. 9). ORCA-2 did not enhance the expression of reporter constructs driven by mutant versions 3 and 4 of the Str-promoter fragment BH (FIG. 9). These results show that the activation of gene expression by ORCA-1 and 2 is sequence-specific and occurs through direct interaction with the Str1-promoter fragment RV. The sequence requirement for ORCA activation in plant cells is slightly different from that in yeast cells (see example 6). In yeast, mutations M2, M3 and M4 affect the ability of ORCA-2 to activate gene expression, whereas in plant cells mutations M5 additionally affects gene expression to some degree. These differences may reflect differences in binding in the two cell types, for instance due to interaction with different endogenous proteins. On the other hand, the transient co-bombardment data closely correlate with the results of the stable transformation (Example 1), indicating that indeed lack of ORCA binding is the reason for lack of expression of mutants M2, 3, 4 and 5 in stably transformed lines.

EXAMPLE 8

ORCA-3 is a Transcriptional Activator of the Tdc and Str1 Promoters in *C. roseus* Cells To investigate whether ORCA-3 activates expression from the Tdc- and Str1-promoters, a particle bombardment assay was performed. C roseus cells were co-bombarded with the gusA-reporter gene with or without an overexpression vector containing the Orca-3 cDNA in the sense orientation. The gusA-reporter gene was driven by a fragment of the Tdc-promoter (−219 to +86 as referred to the translational start site) or the Str1-promoter (−202 to −1 as referred to the translational start site).

24 h after bombardment the cells were stained for GUS activity. A clear increase in the number and intensity of blue spots was observed when the gusA-reporter gene was co-bombarded with 35S-Orca3, when compared to a negative control in which the cells were co-bombarded with the empty overexpression vector. This enhancement was observed both with the Tdc-promoter fragment (FIG. 11) as well as with the Str1-promoter fragment (FIG. 10) driving reporter gene expression. As a control, GUS activity from an unrelated promoter (6Tcyt) was not increased after co-bombardment with Orca-3 (data not shown). Thus in this transient transformation assay, Orca-3 activates gene expression from the Tdc- and Str1-promoter in a sequence-specific manner.

EXAMPLE 9

ORCA-1, -2 and -3 Activate Expression of the Jasmonate-Responsive RV Element from the Str1-Promoter The transient co-bombardment assay, as described above, was used to investigate whether the ORCA proteins activate gene expression of the jasmonate-responsive RV element from the Str1-promoter. *C. roseus* cells were bombarded with a gusA-reporter gene driven by a tetramer of the RV element (4RV) in combination with the empty overexpression plasmid, 35S-Orca1, 35S-Orca2 or 35S-Orca3. The number and intensity of blue spots was increased clearly upon co-bombardment with one of the three Orca genes, when compared to control cells, which were co-bombarded with the empty vector (FIG. 12). The strongest activation of gusA expression was observed when Orca-2 or Orca-3 were used. However, to make statements about the relative strengths of activation of the 3 different ORCAs, quantitative analysis is necessary, thereby correcting for differences in particle coating and bombardment efficiencies. In addition, the differences in activation may be due to differences in expression levels of the three ORCA proteins, instead of differences in activation strength.

EXAMPLE 10

ORCA-3 Does not Activate Gene Expression of RV Mutants M2 and M3, and Weakly for Mutants M4 and M5

35S-Orca3 was co-bombarded with the 4RV mutant series (described in Example 1) to determine which sequences in the RV element were important for the activation by Orca3. After co-bombardment cells were stained for GUS activity and blue staining was quantified visually by estimating the number and intensity of blue spots. The results are shown in the below Table 10.1.

TABLE 10.1

Relative GUS activities as determined visually

| Cells bombarded with | Relative GUS staining | | |
|---|---|---|---|
| 4RV + pMOG | 2 | 2 | 2 |
| 4RV + 35S-Orca3 | 4 | 4 | 4 |
| 4M2 + pMOG | 1 | 1 | 1 |
| 4M2 + 35S-Orca3 | 1.5 | 1 | 1 |
| 4M3 + pMOG | 0.5 | 0.5 | 0.5 |
| 4M3 + 35S-Orca3 | 0.5 | 0.5 | 1 |
| 4M4 + pMOG | 0.5 | 0.5 | 0.5 |
| 4M4 + 35S-Orca3 | 1 | 1 | 1 |
| 4M5 + pMOG | 0.5 | 0.5 | 0.5 |
| 4M5 + 35S-Orca3 | 1.5 | 1.5 | 2 |
| 4M6 + pMOG | 3 | 2.5 | 2.5 |
| 4M6 + 35S-Orca3 | 4 | 4 | 4 |

The above Table 10.11 shows the relative GUS activities as determined visually. The *C. roseus* cells were co-bombarded in triplicate with the gusA reporter gene driven by 4RV or a mutant of this element together with an overexpression plasmid carrying the Orca3 cDNA (35S-Orca3) or the empty vector (pMOG). Cells were stained for GUS activity. The numbers in Table 10.1 are an estimation of the intensity and number of blue spots. Values range from 0 (no blue spots) until 4 (many intense blue spots).

No activation of GUS activity was observed when the gusA reporter gene was driven by a tetramer of RV mutant M2 or M3. For mutants M4 and M5, the basal GUS activity was lower, when compared to the wild-type. However, ORCA-3 was able to activate gene expression of these mutants. Expression of mutant M6 resembled the wild-type, both in basal GUS activity levels, as well in inducibility by ORCA-3. Thus ORCA-3 is able to activate gene expression from the RV element and sequences that are disrupted in mutants 2 and 3 are important for this sequence specific activation. Again, quantitative analysis is necessary to make conclusive statements about the exact sequence requirements for activation of gene expression. The preliminary results indicate that the sequence requirements for activation of gene expression in plant cells by ORCA-3 are the same as for ORCA 2.

EXAMPLE 11

Figure 13A:
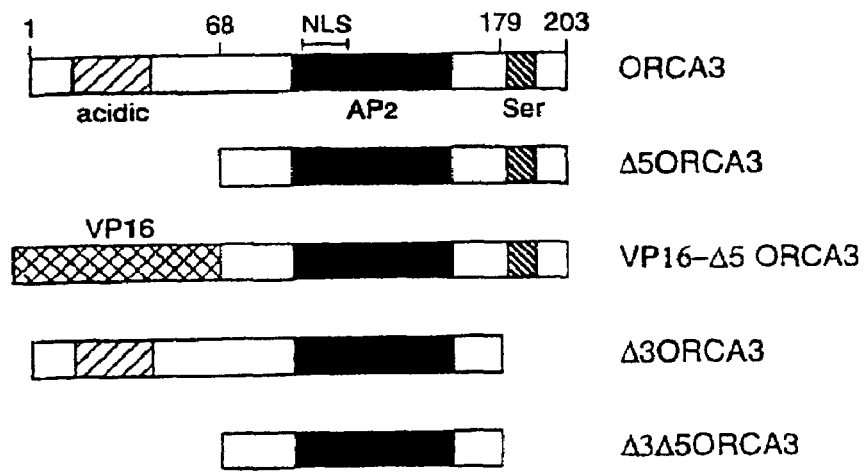
Figure 13B:
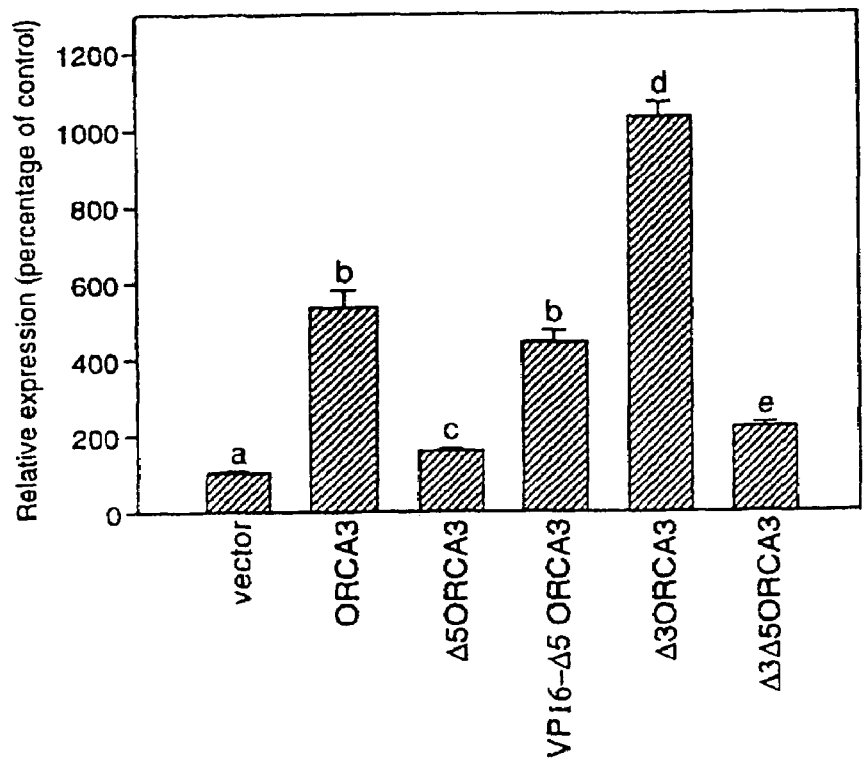

ORCA3 Protein Contains an Acidic Region that has an Activating Function, and a Serine-Rich Region that has a Negative Regulatory Function in Transcription ORCA3 contains an acidic region preceding the AP2-domain. Acidic domains often function in transcriptional activation. In addition, ORCA3 contains a serine-rich region C-terminal of the AP2-domain (FIG. 13A). The in vivo function of these regions was assayed by testing the activation potential of different ORCA3 derivatives on Str promoter activity (FIG. 13B). The Str1-promoter (−202 to −1 respective to the translation start site) fused to the gusA gene was cobombarded with different ORCA3 derivatives (shown in FIG. 13A), cloned in sense orientation in the plant expression vectors pRT101 or pRT104 (containing the CaMV 35S promoter). Full-length ORCA3 protein activated the Str1 promoter about 5-fold (FIG. 13B). Deletion of the acidic region of ORCA3 (resulting in construct Δ5ORCA3) abolished most of the activation. This reduction was not caused by decreased promoter binding in vivo nor to impaired nuclear localization of Δ5ORCA3 protein, since activation was restored by fusion of a heterologous acidic activation domain from Herpes simplex viral protein VP16 (amino acids 413-487) to Δ5ORCA3. Deletion of the serine-rich region (construct Δ3ORCA3) resulted in higher activation. This indicates that the acidic region has an activating effect on transcription, whereas the serine-rich region has a repressing effect.

EXAMPLE 12

Overexpression of ORCA3 Up-Regulates Multiple Genes in Primary as Well as Secondary Metabolism In line 46, the Orca3 gene was activated by insertion of a T-DNA activation tag. Gene expression in the tagged cell line 46 overexpressing Orca3 was analysed by Northern blotting and hybridization with different cDNA clones. This showed that the TIA biosynthetic genes Tdc, Str, Sgd, and D4h were expressed at high levels, while the expression of G10h and Dat was not affected (FIG. 14A). In addition, genes encoding the alpha subunit of AS (Asa) and DXS, enzymes involved in primary metabolism producing precursors of the indole and terpenoid moiety of TIAs, respectively, were induced by Orca3 overexpression, whereas two other primary metabolic genes, that are not involved in production of TIA precursors (geranylgeranyl pyrophosphate synthase, Ggpps; and isochorismate synthase, Ics) were not regulated by ORCA3 (FIG. 14A).

The rescued Orca3 gene fused to the 2B4A1 plant promoter was introduced in *C. roseus* cells by particle bombardment to generate stably transformed cell lines that overexpressed the Orca3 gene (O3-OX cell lines). The O3-OX lines had higher expression levels of the endogenous Tdc, Str, Cpr and D4h genes (FIGS. 14B and D). Due to the variable expression of Sgd in the different lines, no statistically significant effect of Orca3 overexpression was observed in the O3-OX lines (FIGS. 14B and D). The G10h gene was not activated by ORCA3 overexpression (FIGS. 3B and D). In addition to the genes mentioned, also anthranilate synthase (Asa) and D-1-deoxyxylulose-5-phosphate synthase (Dxs) were expressed at higher levels in the O3-OX lines (FIGS.

49

14B and D). This indicates that ORCA3 not only regulates multiple genes in the TIA pathway, but in addition genes in primary metabolism that are involved in production of TIA precursors. Although it has been shown that genes (D4h and Dat) in the later part of the pathway leading to vindoline and dimeric alkaloids have a different cell-type-specific regulation compared to genes (Tdc and Str) in the earlier part of the TIA pathway, the D4h gene also shows increased expression in O3-OX lines compared to control lines (FIGS. 14B and D).

EXAMPLE 13

Overexpression of ORCA3 Results in Elevated Tryptophan, Tryptamine and TIA Production Metabolite levels were measured in five representative O3-OX lines and in 5 control lines. The O3-OX lines contained increased levels of tryptophan and tryptamine (FIG. 15, left panel). The O3-OX cell lines did not accumulate alkaloids in standard LS-13 growth medium (FIG. 15, left panel), probably because the G10h gene was not activated by

50

ORCA3 overexpression. Upon feeding of a secologanin precursor (loganin), increased amounts of strictosidine (8.11±0.87 µmoles/g DW), ajmalicine (0.25±0.10 µmoles/g DW; collectively termed TIAs in FIG. 15, right panel) and an unidentified lochnericin-like TIA (1.21±0.66 area units/g DW) accumulated compared to control lines.

EXAMPLE 14

Overexpression of ORCA2 Up-Regulates Tdc, Str1 and G10h Gene Expression

The Orca2 gene, fused to the CaMV 35S promoter in vector pMOG184, was introduced in *C. roseus* cells by particle bombardment to generate stable transgenic lines that overexpress the Orca2 gene (O2-OX lines). RNA analysis showed that the genes Tdc and Str showed increased expression (FIG. 16), although the effect on Tdc was marginal. Surprisingly, the G10h gene, which was not expressed in O3-OX lines (FIGS. 14B and D), was highly expressed in O2-OX lines (FIG. 16).

The invention claimed is:

1. An isolated nucleic acid molecule comprising SEQ ID NO: 3.

2. A method of increasing in a *Catharanthus* plant cell the expression of one or more genes involved in the biosynthesis of tryptophane or tryptamine, said method comprising the steps of:
   a) transforming the cell with a genetic construct comprising a nucleotide sequence encoding an AP2-domain transcription factor, operably linked to an expression regulating sequence that is operable in said cell; and,
   b) cultivating said cell under conditions such that the nucleotide sequence is expressed in said cell;
   wherein said nucleotide sequence encodes an AP2-domain transcription factor selected from:
   i) a transcription factor having the amino acid sequence of SEQ ID NO: 6; and
   ii) a transcription factor having an amino acid sequence that comprises at least amino acids 68-179 of SEQ ID NO: 6,
   wherein the transcription factor enhances the biosynthesis in *Catharanthus roseus* cells of at least one of tryptophane or tryptamine, when stably expressed in said *C. roseus* cells from a genetic construct comprising a sequence coding for the transcription factor operably linked to a plant promoter in a sense orientation.

3. An isolated nucleic acid molecule comprising a nucleotide sequence selected from the group consisting of:
   a) SEQ ID NO: 3; and
   b) a nucleotide sequence encoding an AP2-domain transcription factor selected from the group consisting of
   i) SEQ ID NO: 6;
   ii) a transcription factor comprising amino acids 68-203 of SEQ ID NO: 6; and
   iii) a transcription factor comprising amino acids 1-179 of SEQ ID NO: 6.

4. A method of increasing in a *Catharanthus* plant cell the level(s) of expression of tryptamine or tryptophane, said method comprising the steps of:
   a) transforming the cell with a genetic construct comprising a nucleotide sequence encoding an AP2-domain transcription factor, operably linked to an expression regulating sequence that is operable in said cell; and,
   b) cultivating said cell under conditions such that the level of AP2-domain transcription factor is expressed in said cell;
   wherein said nucleotide sequence encodes an AP2-domain transcription factor selected from:
   i) a transcription factor having the amino acid sequence of SEQ ID NO: 6;
   ii) a transcription factor comprising amino acids 68-203 of SEQ ID NO: 6; and
   iii) a transcription factor comprising amino acids 1-179 of SEQ ID NO: 6,
   wherein the transcription factor enhances the biosynthesis of at least one of tryptophane or tryptamine, when stably expressed in said cells from a genetic construct comprising a sequence coding for the transcription factor operably linked to a plant promoter in a sense orientation.

5. The method according to claim 4, wherein the plant cell is *Catharanthus roseus*.

6. The method according to claim 2, wherein the plant cell is *Catharanthus roseus*.

7. The method according to claim 2, wherein the nucleotide sequence that encodes an AP-2 domain transcription factor encodes a transcription factor having an amino acid sequence of SEQ ID NO:6.

8. The method according to claim 2, wherein the nucleotide sequence that encodes an AP-2 domain transcription factor has an amino acid sequence that comprises at least amino acids 68-179 of SEQ ID NO: 6.

9. The isolated nucleic acid molecule according to claim 3, wherein the nucleotide sequence is a nucleotide sequence encoding an AP-2 domain transcription factor comprising SEQ ID NO: 6.

10. The isolated nucleic acid molecule according to claim 3, wherein the nucleotide sequence is a nucleotide sequence encoding an AP-2 domain transcription factor comprising amino acids 68-203 of SEQ ID NO: 6.

11. The isolated nucleic acid molecule according to claim 3, wherein the nucleotide sequence is a nucleotide sequence encoding an AP-2 domain transcription factor comprising amino acids 1-179 of SEQ ID NO: 6.

12. The method according to claim 4, wherein the nucleotide sequence encodes an AP-2 domain transcription factor having the amino acid sequence of SEQ ID NO:6.

13. The method according to claim 4, wherein the nucleotide sequences encodes an AP-2 domain transcription factor comprising amino acids 68-203 of SEQ ID NO: 6.

14. The method according to claim 4, wherein the nucleotide sequence encodes an AP-2 domain transcription factor comprising amino acids 1-179 of SEQ ID NO: 6.

* * * * *

```
                            SEQUENCE LISTING

<160> NUMBER OF SEQ ID NOS: 21

<210> SEQ ID NO 1
<211> LENGTH: 1754
<212> TYPE: DNA
<213> ORGANISM: Catharanthus roseus

<400> SEQUENCE: 1
tgtaaatcaa atttcacaca gttttagaac tctacgacct atttgttact gaaaattact      60
ggaattacta aaatcggaag aagaaatcaa cgcgacgaaa gagaaaaaga acaaaagggt     120
ttcgtttttg taaagtttga ttcttggcgg agattttcga caaaggagtg ggcaatttgt     180
gcaatacttc tgagaaaatt gaaagagata caaggatggc tcttcttgat caggcatcca     240
atttgagtcc catgcctttt gatttcacta gaaagaggaa gtcgaggagg agggatggta     300
ctaagaacgt agcggagaca cttgcaaagt ggaaagagta taatgagaaa cttgatgctt     360
tagatggagg gaaaccagct cggaaggttc ctgccaaagg atcaaaaaag ggatgtatga     420
aaggtaaagg aggccctgag aattctcact gcaaatacag aggagttagg cagaggacat     480
ggggtaaatg ggtggccgaa attcgggaac caaacagggg tagcaggctt tggttgggta     540
cattcagaaa cgcgatagaa gctgcacttg cttatgatga agcagcgagg gcgatgtatg     600
ggccttgtgc taggcttaat cttccgaact atagggcttc agaagaatct tcttccttgc     660
caacaacatc aggatcagat acgactactg cttctggcat ctcagaggtc tctgtctatg     720
aagacaaaaa gttcacacca gttgtttccg gattgaaaca agatgacaag ggtgaatcat     780
tagagtcagc tgatagtaaa cctcaactcc tggtcgatgc tggcactccc atgagtgcag     840
tgaaggaaga accaaaagaa tatcaggtta tggattccca gtctgaaggg caattcggag     900
acgaggaacc gcctagcaag cttgtttgta aagaagtcga ctttgggcag gatcaagctg     960
ttgttcctgc tgttaaaaat gctgaggaga tgggtggaga gatgggtgga gatatactga    1020
aaggctgttc tttgtctgag atgtttgatg tggacgagtt gttgagcgtt ttagattcta    1080 caccctcca tgcctcagat tttcagcatg gcatgggaaa tggtaatgta aaggcagagg    1140
ctgcttacaa ctatgctcct tcatgggact cggccttcca gttgcagaat caagatccta    1200
```

-continued

```
agctaggaag tcagcagcac atggcgcaga caccccccaga aattaattcc gggcttgatt   1260
ttttgcagcc aggaagacaa gaggactcct attttacttt gggtgatcta gactttcttg   1320
atttgggtgc tgaattggga ttgtaaatcc gaagttgttg aagctaaaag cggcgactat   1380
gaaactggaa ttttggaacg gcttattgtt cctggtgttt gtcttagttc tagtctgttt   1440
atgtactaga acttgacata taggaggctt ttgaaagctg aacaaacgaa gtgtgaatta   1500
ttttcttttt ttgttttttct gcagcgatgt atactaacat ctctactact aaaattacgt   1560
ctcttcgtct tcactaacag tagggtggag ctgattctct tttaagtttt tcagaagggg   1620
aattcagcta tgagtttaga ggcagggtag tgtagttcag tgagcagatt ctttctgtag   1680
atatctctag tcttttggtt tcttggaatg ttttttctgg tggaataaag atggcatagg   1740
tggaggttgt atct                                                      1754
```

<210> SEQ ID NO 2
<211> LENGTH: 885
<212> TYPE: DNA
<213> ORGANISM: Catharanthus roseus

<400> SEQUENCE: 2

```
caacaataat gtatcaatca aatgcccata attccgatca tctaaccttc ttaccacctt     60
tagtagatta tcaattcctc aacaacgatt ttgattttc agaaatattt acagatttca     120
attacgctaa ttataattat aatacttcta cctcagataa tttctctggt tttcaattca    180
atgaaaattg cgaagaaatt atttcaccaa attatgcttc ggaagattta tcggatatta    240 tttttaacaga tattttcaag gatcaggata attacgaaga cgaagtcgtt gcgggagaac   300
aagaagaaga attaattacg acacctacct ctcgcggcgg cggcggcggc ggatgtgagc    360
agagatcgaa tgaggaatgg attaggtacc gtggcgttag acggcggcca tggggggaaat  420 tcgctgcgga aatcagggat cccaagagaa aaggatcgag gatatggttg gaacttacg    480 agacggcgga agatgcggca ttagcttcg atcaagcggc gtttcaactc cgtggttcta    540
gagctaggtt aaattttccc aatcttattg gttctgctaa tgctccggtt agagtaagtc    600
ctagacgccg atcttcatcg tgtcatcttc gtcctcaata atcctatcca cagttccatg    660
gggatagtaa atttttctt tgagtttttt agaagttata ttatctattg aaaaaataca     720
aaacattgca aatattttt tagtacgtct ctatacttct ttttagtaat attcggatca     780
tgagcatggg gaaggtgata ttatccattg tcataaatta atagatacag tatcataaat    840
taatatgtac gaattacaag taaaatatag taagtgttaa tattg                    885
```

<210> SEQ ID NO 3
<211> LENGTH: 792
<212> TYPE: DNA
<213> ORGANISM: Catharanthus roseus

<400> SEQUENCE: 3

```
ttctaaaaaa gaagaaaaat gtccgaagaa atcatttccg tctcagatcg atttcttctt    60
tccttaatcg aagaacatct tctcagcgat aattctgatg attccagctc ggaattgact   120
tctacagagg aaaattggga agaaattttt gcagattttc taaattggtc gggatccgaa   180
atacagaaac gcgtagcccc gagttccgaa agctgtcaat cgaattcaat ggcggaaagc   240
tgtcaggagg attctgttgt gggaaccccg ccagaagcgg cggccggagg aggttgttcg   300
aaggattgga accggtataa gggcgttaga cggcggccgt gggggaagtt cgcggcggag   360
ataagggatc cgaaaaagaa aggatccagg atttggttgg gtacatacga gacacctgag   420
```

-continued

```
gatgcagcat tggcttatga tgcagccgcg tttaatatgc gtggagctaa agctaggctt      480
aattttcctc atttgattgg ttcgaatatt tccggacccg ttagagtaaa cccgagaaaa      540
cgtttccctg cggagccttc tacgacgtcg tcgtcttctt cttcttcttc gtctgaaaat      600
agtggaggaa ggaagaagag acgatattaa ttaattatta aaagtggagg attaaaaaaa      660
ttctgtgaaa tgagagatta ttacgtggtt tttgttaagc ccgataatcc ctcattgtaa      720
aattattaac ttcatcgatg ttctttttta aatctttgga atgtacaaaa ttttatatcc      780
aaaaaagttc ac                                                          792
```

```
<210> SEQ ID NO 4
<211> LENGTH: 376
<212> TYPE: PRT
<213> ORGANISM: Catharanthus roseus

<400> SEQUENCE: 4
```

| Met | Ala | Leu | Leu | Asp | Gln | Ala | Ser | Asn | Leu | Ser | Pro | Met | Pro | Phe | Asp |
|---|---|---|---|---|---|---|---|---|---|---|---|---|---|---|---|
| 1 | | | | 5 | | | | | 10 | | | | | 15 | |

Phe Thr Arg Lys Arg Lys Ser Arg Arg Arg Asp Gly Thr Lys Asn Val
                20                  25                  30

Ala Glu Thr Leu Ala Lys Trp Lys Glu Tyr Asn Glu Lys Leu Asp Ala
            35                  40                  45

Leu Asp Gly Gly Lys Pro Ala Arg Lys Val Pro Ala Lys Gly Ser Lys
        50                  55                  60

Lys Gly Cys Met Lys Gly Lys Gly Pro Glu Asn Ser His Cys Lys
 65                  70                  75                  80

Tyr Arg Gly Val Arg Gln Arg Thr Trp Gly Lys Trp Val Ala Glu Ile
                 85                  90                  95

Arg Glu Pro Asn Arg Gly Ser Arg Leu Trp Leu Gly Thr Phe Arg Asn
            100                 105                 110

Ala Ile Glu Ala Ala Leu Ala Tyr Asp Glu Ala Ala Arg Ala Met Tyr
        115                 120                 125

Gly Pro Cys Ala Arg Leu Asn Leu Pro Asn Tyr Arg Ala Ser Glu Glu
    130                 135                 140

Ser Ser Ser Leu Pro Thr Thr Ser Gly Ser Asp Thr Thr Thr Ala Ser
145                 150                 155                 160

Gly Ile Ser Glu Val Ser Val Tyr Glu Asp Lys Lys Phe Thr Pro Val
                165                 170                 175

Val Ser Gly Leu Lys Gln Asp Asp Lys Gly Glu Ser Leu Glu Ser Ala
            180                 185                 190

Asp Ser Lys Pro Gln Leu Leu Val Asp Ala Gly Thr Pro Met Ser Ala
        195                 200                 205

Val Lys Glu Glu Pro Lys Glu Tyr Gln Val Met Asp Ser Gln Ser Glu
    210                 215                 220

Gly Gln Phe Gly Asp Glu Pro Ser Lys Leu Val Cys Lys Glu
225                 230                 235                 240

Val Asp Phe Gly Gln Asp Gln Ala Val Val Pro Ala Val Lys Asn Ala
                245                 250                 255

Glu Glu Met Gly Gly Glu Met Gly Gly Asp Ile Leu Lys Gly Cys Ser
            260                 265                 270

Leu Ser Glu Met Phe Asp Val Asp Glu Leu Leu Ser Val Leu Asp Ser
        275                 280                 285

Thr Pro Leu His Ala Ser Asp Phe Gln His Gly Met Gly Asn Gly Asn
    290                 295                 300

```
Val Lys Ala Glu Ala Ala Tyr Asn Tyr Ala Pro Ser Trp Asp Ser Ala
305                 310                 315                 320

Phe Gln Leu Gln Asn Gln Asp Pro Lys Leu Gly Ser Gln Gln His Met
            325                 330                 335

Ala Gln Thr Pro Pro Glu Ile Asn Ser Gly Leu Asp Phe Leu Gln Pro
            340                 345                 350

Gly Arg Gln Glu Asp Ser Tyr Phe Thr Leu Gly Asp Leu Asp Phe Leu
            355                 360                 365

Asp Leu Gly Ala Glu Leu Gly Leu
    370                 375

<210> SEQ ID NO 5
<211> LENGTH: 210
<212> TYPE: PRT
<213> ORGANISM: Catharanthus roseus

<400> SEQUENCE: 5

Met Tyr Gln Ser Asn Ala His Asn Ser Asp His Leu Thr Phe Leu Pro
1               5                   10                  15

Pro Leu Val Asp Tyr Gln Phe Leu Asn Asn Asp Phe Asp Phe Ser Glu
            20                  25                  30

Ile Phe Thr Asp Phe Asn Tyr Ala Asn Tyr Asn Tyr Asn Thr Ser Thr
            35                  40                  45

Ser Asp Asn Phe Ser Gly Phe Gln Phe Asn Glu Asn Cys Glu Glu Ile
    50                  55                  60

Ile Ser Pro Asn Tyr Ala Ser Glu Asp Leu Ser Asp Ile Ile Leu Thr
65                  70                  75                  80

Asp Ile Phe Lys Asp Gln Asp Asn Tyr Glu Asp Glu Val Val Ala Gly
                85                  90                  95

Glu Gln Glu Glu Glu Leu Ile Thr Thr Pro Thr Ser Arg Gly Gly Gly
            100                 105                 110

Gly Gly Gly Cys Glu Gln Arg Ser Asn Glu Glu Trp Ile Arg Tyr Arg
        115                 120                 125

Gly Val Arg Arg Arg Pro Trp Gly Lys Phe Ala Ala Glu Ile Arg Asp
    130                 135                 140

Pro Lys Arg Lys Gly Ser Arg Ile Trp Leu Gly Thr Tyr Glu Thr Ala
145                 150                 155                 160

Glu Asp Ala Ala Leu Ala Phe Asp Gln Ala Ala Phe Gln Leu Arg Gly
                165                 170                 175

Ser Arg Ala Arg Leu Asn Phe Pro Asn Leu Ile Gly Ser Ala Asn Ala
            180                 185                 190

Pro Val Arg Val Ser Pro Arg Arg Ser Ser Ser Cys His Leu Arg
        195                 200                 205

Pro Gln
    210

<210> SEQ ID NO 6
<211> LENGTH: 203
<212> TYPE: PRT
<213> ORGANISM: Catharanthus roseus

<400> SEQUENCE: 6

Met Ser Glu Glu Ile Ile Ser Val Ser Asp Arg Phe Leu Leu Ser Leu
1               5                   10                  15

Ile Glu Glu His Leu Leu Ser Asp Asn Ser Asp Asp Ser Ser Ser Glu
            20                  25                  30
```

-continued

```
Leu Thr Ser Thr Glu Glu Asn Trp Glu Glu Ile Phe Ala Asp Phe Leu
            35                  40                  45

Asn Trp Ser Gly Ser Glu Ile Gln Lys Arg Gly Ser Pro Ser Ser Glu
 50                  55                  60

Ser Cys Gln Ser Asn Ser Met Ala Glu Ser Cys Gln Glu Asp Ser Val
 65                  70                  75                  80

Val Gly Thr Pro Pro Glu Ala Ala Ala Gly Gly Cys Ser Lys Asp
                 85                  90                  95

Trp Asn Arg Tyr Lys Gly Val Arg Arg Pro Trp Gly Lys Phe Ala
             100                 105                 110

Ala Glu Ile Arg Asp Pro Lys Lys Lys Gly Ser Arg Ile Trp Leu Gly
             115                 120                 125

Thr Tyr Glu Thr Pro Glu Asp Ala Ala Leu Ala Tyr Asp Ala Ala Ala
             130                 135                 140

Phe Asn Met Arg Gly Ala Lys Ala Arg Leu Asn Phe Pro His Leu Ile
145                 150                 155                 160

Gly Ser Asn Ile Ser Gly Pro Val Arg Val Asn Pro Arg Lys Arg Phe
                165                 170                 175

Pro Ala Glu Pro Ser Thr Thr Ser Ser Ser Ser Ser Ser Ser Ser
             180                 185                 190

Glu Asn Ser Gly Gly Arg Lys Lys Arg Arg Tyr
             195                 200

<210> SEQ ID NO 7
<211> LENGTH: 48
<212> TYPE: DNA
<213> ORGANISM: Catharanthus roseus

<400> SEQUENCE: 7
gtacatcact cttagaccgc cttctttgaa agtgatttcc cttggacc                  48

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 8
ccacgtggtt gtagtctctt agacc                                           25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 9
ggtacatcag agaatgaccg ccttc                                           25

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 10
cactcttact ggcgcttctt tgaaag                                          26
```

```
<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 11
agaccgcgaa gaatgaaagt g                                              21

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 12
agaccgcctt cttactttct gatttcccc                                      29

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 13
ttgaaagact aaaccctcgg ac                                             22

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 14
gaaagtgatt tgggaacgac cttg                                           24

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 15
cccttgctgg aagtttggtg ag                                             22

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 16
ccccaccaaa cccaaaaaaa g                                              21

<210> SEQ ID NO 17
<211> LENGTH: 22
<212> TYPE: DNA
<213> ORGANISM: Artificial Sequence
<220> FEATURE:
```

-continued

```
<223> OTHER INFORMATION: Description of Artificial Sequence: primer

<400> SEQUENCE: 17
ccatatcctc gatccttttc tc                                                  22

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 18
gaattcatat ggcggaaagc tgtcaggagg attc                                     34

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 19
cgacgtcgta gaaggctccg caggg                                               25

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 20
agatctcata gttccgaaga aatcatttcc gtctcag                                  37

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 21
agactcgtga actttttggg atataaaatt ttgtacattc c                             41
```